United States Patent [19]
Bell et al.

[11] Patent Number: 6,096,513
[45] Date of Patent: Aug. 1, 2000

[54] POLYNUCLEOTIDES ENCODING KAPPA OPIOD RECEPTORS

[75] Inventors: Graeme I. Bell, Chicago, Ill.; Terry Reisine, Philadelphia, Pa.; Kazuki Yasuda, Tokyo, Japan

[73] Assignee: Arch Development Corporation, Chicago, Ill.

[21] Appl. No.: 08/147,592

[22] Filed: Nov. 5, 1993

Related U.S. Application Data

[63] Continuation-in-part of application No. 08/100,694, Jul. 30, 1993, abandoned, which is a continuation-in-part of application No. 08/066,296, May 20, 1993, abandoned.

[51] Int. Cl.$^7$ .......................... C12N 15/12; C07K 14/705
[52] U.S. Cl. .................... 435/69.1; 536/23.5; 536/24.31; 435/252.3; 435/254.11; 435/254.2; 435/358; 435/365; 435/325
[58] Field of Search .................................. 536/23.1, 23.5, 536/24.31; 435/69.1, 240.1, 320.1, 325, 358, 365, 254.11, 252.3, 254.2

[56] References Cited

FOREIGN PATENT DOCUMENTS

| | | |
|---|---|---|
| 2064114 | 9/1992 | Canada . |
| 508221 | 10/1992 | European Pat. Off. . |
| WO 94/11500 | 5/1994 | WIPO . |

OTHER PUBLICATIONS

Dohlman et al., "Model Systems for the Study of Seven–Transmembrane–Segment Receptors," *Annu. Rev. Biochem.*, 60:653–688, 1991.

Dohlman et al., "A Family of Receptors Coupled to Guanine Nucleotide Regulatory Proteins," *Biochemistry*, 26:2657–2664, 1987.

Frielle et al., "Structural Basis of β–adrenergic Receptor Subtype Specificity Studied with Chimeric β1/β2–adrenergic Receptors," *Proc. Natl. Acad. Sci. USA*, 85:9494–9498, 1988.

Gioannini, T.L. et al., "Evidence for the Presence of Disulfide Bridges in Opioid Receptors Essential for Ligand Binding. Possible Role in Receptor Activation," *J. Mol. Recogn.*, 2:44–48, 1989.

Kieffer et al., "The δ–opioid Receptor: Isolation of a cDNA by Expression Cloning and Pharmacological Characterization," *Proc. Natl. Acad. Sci. USA*, 89:12048–12052, 1992.

Lutz et al., "Opioid Receptors and Their Pharmacological Profiles," *J. Receptor Res.*, 12:267–286, 1992.

Mansour et al., "Anatomy of CNS Opioid Receptors," *Trends in Neurosci.*, 7:2445–2453, 1987.

Nock et al., "Autoradiography of [3H]U–69593 Binding Sites in Rat Brain: Evidence for K Opioid Receptor Subtypes," *Eur. J. Pharmacol.*, 154:27–34, 1988.

Simon, "Opioid Receptors and Endogenous Opioid Peptides," *Medicinal Res. Rev.*, 11:357–374, 1991.

Unterwald et al., "Neuroanatomical Localization of K1 and K2 Opiod Receptors in Rat and Guinea Pig Brain," *Brain Res.*, 562:57–65, 1991.

Yamada et al., "Cloning and Functional Characterization of a Family of Human and Mouse Somatostatin Receptors Expressed in Brain, Gastrointestinal Tract, and Kidney," *Proc. Natl. Acad. Sci. USA*, 89:251–255, 1992.

Yasuda et al., "Cloning of a Novel Somatostatin Receptor, SSTR3, Coupled to Adenylylcyclase," *J. Biol. Chem.*, 267:20422–20428, 1992.

Probst et al., "Sequence Alignment of the G–Protein Coupled Receptor Superfamily," *DNA and Cell Biology*, 11:1–20, 1992.

Kong, et al., "A Single Residue, Aspartic Acid 95, in the δ Opioid Receptor Specifies Selective High Affinity Agonist Binding," *J. Biol. Chem.*, 268(31):23055–23058 (1993).

Raynor, et al., "Molecular Mechanisms of Agonist–Induced Desensitization of the Cloned Mouse Kappa Opioid Receptor," *J. Pharmacol. Exp. Ther.*, 270(3):1381–1386 (1994).

Blake, et al., "Differential Agonist Regulation of the Human κ–Opioid Receptor," *J. Neurochem.*, 68(5):001–007 (1997).

Evans et al., Science, V. 258, p. 1952, 1992.

Goldstein et al., PNAS, V. 85, p. 7375, 1988.

Loh et al., Annu. Rev. Pharmacol. Toxicol, V. 30, p. 123, 1990.

Sambrook et al., Mol. Cloning, A Lab Manual, V. 3, p. 16.2, 1989, Cold Spring Harbor Press.

Schofield et al., EMBO, V. 8, p. 489, 1989.

Sims et al, Science, V. 241, p. 586, 1988.

Xie et al., PNAS, V. 89, p. 4124, 1992.

Lin et al., Science, vol. 254, pp. 1022, 1991.

Evans et al., Society for Neuroscience Abstracts, vol. 18, Part 1, 22$^{nd}$ Annual Meeting, Oct. 25–30, 1992.

*Primary Examiner*—Sally P. Teng
*Attorney, Agent, or Firm*—Arnold White & Durkee

[57] ABSTRACT

The invention relates generally to compositions of and methods for using polynucleotides encoding kappa opioid receptors. In addition to such polynucleotides themselves, the invention relates to expression vectors comprising polynucleotides encoding kappa opioid receptors, recombinant host cells comprising such polynucleotides, and processes for preparing kappa opioid receptor polypeptides.

31 Claims, 19 Drawing Sheets

```
                                                              TM1
mORK1  MESPIQIFRGDPGPTCSPSPSACLLPNSSSW:::::FPNWAESDSNGSVGSEDQQLESAHISPAIPVIITAVY    66
         **                    ***    |**       **    **         *    *|   ***|*
mORD1  ME:::::::::::::LVPSARAELQSSPLVNLSDAFPSAGANASGSPGARSASSL:::ALAIAITALY         56
                                                              TM2 mORK1  SVVFVVGLVGNSLVMFVIIRYTKMKTATNIYIFNLALADALVTTTMPFQSAVYLMNSWPFGDVLCKIVISID    138
       * *  *| ****   *|*|******************* *|*|****  *  |**** *|***
mORD1  SAVCAVGLLGNVLVMFGIVRYTKLKTATNIYIFNLALADALATSTLPFQSAKYLMETWPFGELLCKAVLSID    128
                TM3                                               TM 4 mORK1  YYNMFTSIFTLTMMSVDRYIAVCHPVKALDFRTPLKAKIINICIWLLASSVGISAIVLGGTKVREDVDVIEC    210
       ********************************* * ***** * *        * **
mORD1  YYNMFTSIFTLTMMSVDRYIAVCHPVKALDFRTPAKAKLINICIWLASGVGVPIMMAVTQPRDGAVV::C      198
                                                      TM 5 mORK1  SLQFPDDEYSWWDLFMKICVFVFAFVIPVLIIIVCYTLMILRLKSVRLLSGSREKDRNLRRITKLVLVVVAV    282
       **    |  |   ****|**|*|*   |********|  **||****
mORD1  MLQFPSPSW:YWDTVTKICVFLFAFVVPILIITVCYGLMLLRLRSVRLLSGSKEKDRSLRRITRMLVVVGA    269
                TM 6                                       TM 7 mORK1  FIICWTPIHIFILVEALGSTSHSTAALSSYY:FCIALGYTNSSLNPVLYAFLDENFKRCFRDFCFPIKMRME    353
       *|| ***||*  *          |       ****  **************   *    * *
mORD1  FVVCWAPIHIFVIWTLVDINRRDPLVVAALHLCIALGYANSSLNPVLYAFLDENFKRCFRQLCRTPCGRQE    341 mORK1  RQSTNRVRNTVQDP:::::ASMRDVGGMNKPV  380       (SEQ ID NO:2)
          *  *  *       |     *   *
mORD1  PGSLRRPRQATTRERVTACTPSDGPGGGAAA  372       (SEQ ID NO:4)
```

FIG. 1

```
  1  AAGAAGCAAAATCAGTAATCCAAAGGCTATCACAAACACATTCACCTTATGGGGTTTGAC
                                                TyrThrLysMetLysThrAla
 61  TTGAAAATGGAGGGAAATGCTATTGTTCTTTTCTTTTAGATACACAAAGATGAAGACAG
     ThrAsnIleTyrIlePheAsnLeuAlaLeuAlaAspAlaAlaLeuValThrThrThrMetPro
121  CAACCAACATTTACATATATTTAACCTGGCTTTGGCAGATGCTTTAGTTACTACAACCATGC
     PheGlnSerThrValTyrLeuMetAsnSerTrpProPheGlyAspValLeuCysLysIle
181  CCTTTCAGAGTACGGTCTACTTGATGAATTCCTGGCCTTTTGGGGATGTGCTGTGCAAGA
     ValIleSerIleAspTyrTyrAsnMetPheThrSerIlePheThrLeuThrMetMetSer
241  TAGTAATTTCCATTGATTACTACAACATGTTCACCAGCATCTTCACCTTGACCATGATGA
     ValAspArgTyrIleAlaValCysHisProValLysAlaLeuAspPheArgThrProLeu
301  GCGTGGACCGCTACATTGCCGTGTGCCACCCCGTGAAGGCTTTGGACTTCCGCACACCCT
     LysAlaLysIleIleAsnIleIleCysIleTrpLeuLeuSerSerSerValGlyIleSerAla
361  TGAAGGCAAAGATCATCAATATCTGCATCTGGCTGCTGTCGTCATCTGTTGGCATCTCTG
```

FIG. 3A

```
     LysAlaLysIleIleAsnIleCysIleTrpLeuLeuSerSerValGlyIleSerAla
361  TGAAGGCAAAGATCATCAATATCTGCATCTGGCTGCTGTCGTCATCTGTTGGCATCTCTG

IleValLeuGlyGlyThrLysValArgGluA
421  CAATAGTCCTTGGAGGCACCAAAGTCAGGGAAGGT::::::::::TTTCTGTGTTGT spValAspValIleGluCysCysLeuGlnPheProAsp
481  GGTTTTTATTGCCCTCCTCCAGACGTGCGATGTCATTGAGTGCTGCTTGCAGTTCCCAGAT

AspAspTyrSerTrpTrpAspLeuPheMetLysIleCysValPheIlePheAlaPheVal
541  GATGACTACTCCTGGTGGGACCTCTTCATGAAGATCTGCGTCTTCATCTTTGCCTTCGTG

IleProValLeuIleIleIleValCysTyrThrLeuMetIleLeuArgLeuLysNNNVal
601  ATCCCTGTCCTCATCATCATCGTCTGTTACACCCTGATGATCCTGCGTCTCAAGANNGTC

ArgLeuLeuSerGlySerArgGluLysAspNNNAsnLeuArgArgIleThrArgLeuVal
661  CGGCTCCTTTCTGGCTCCCGAGAGAAAGATNNCAACCTGCGTAGGATCACCAGACTGGTC
```

FIG. 3B

```
      ArgLeuLeuSerGlySerArgGluLysAspNNNAsnLeuArgArgIleThrArgLeuVal
661   CGGCTCCTTTCTGGCTCCCGAGAGAAAGATNNCAACCTGCGTAGGATCACCAGACTGGTC

LeuValValAlaValPheValValCysTrpThrProIleHisIleIlePheIleLeuVal
721   CTGGTGGTGGTGGCAGTCTTCGTCGTCTGCTGGACTCCCATTCACATATTCATCCTGGTG

GluAlaLeuGlySerThrSerHisSerSerThrAlaAlaLeuSerSerTyrTyrPheCysIle
781   GAGGCTCTGGGGAGCACCTCCCACAGCACAGCTGCTCTCCCAGTATTACTTCTGCATC

AlaLeuGlyTyrThrAsnSerSerLeuAsnProIleLeuTyrAlaPheLeuAspGluAsn
841   GCCTTAGGCTATACCAACAGTAGCCTGAATCCCATTCTCTACGCCTTTCTGATGAAAAC

PheLysArgCysPheArgAspPheCysPheProLeuLysMetNNNMetGluArgNNNSer
901   TTCAAGCGGTGTTTCCGGGACTTCTGCTTTCCACTGAAGATGAGNATGGAGCGCNAGAGC

ThrSerArgValArgAsnThrValGlnAspProAlaTyrLeuArgGluIleAspGlyMet
961   ACTAGCAGAGTCCGAAATACAGTTCAGGATCCTGCTTACCTGAGGGAGATCGATGGGATG

MetAsnLysProValop                            (SEQ ID NO:12)
1021  ATGAATAAACCAGTATGACTAGTCGTGGA                (SEQ ID NO:11)
```

FIG. 3C

Met Glu Ser Pro Ile Gln Ile Phe Arg Gly Asp Pro Gly Pro Thr Cys
1               5                   10                  15

Ser Pro Ser Ala Cys Leu Leu Pro Asn Ser Ser Ser Trp Phe Pro Asn
                20                  25                  30

Trp Ala Glu Ser Asp Ser Asn Gly Ser Val Gly Ser Glu Asp Gln Gln
                35                  40                  45

Leu Glu Ser Ala His Ile Ser Pro Ala Ile Pro Val Ile Ile Thr Ala
                50                  55                  60

Val Tyr Ser Val Val Phe Val Val Gly Leu Val Gly Asn Ser Leu Val
65                  70                  75                  80

Tyr Thr Lys Met Lys Thr Ala Thr Asn Ile
                        85                  90

HUMAN
MOUSE  Met Phe Val Ile Ile Arg Tyr Thr Lys Met Lys Thr Ala Thr Asn Ile
                        85                  90                  95

FIG. 4A-1

| | | | | | | | | | | |
|---|---|---|---|---|---|---|---|---|---|---|
| HUMAN | Tyr | Ile | Phe | Asn | Leu | Ala | Leu | Ala | Asp | Ala | Leu Val Thr Thr Thr Met |
| MOUSE | Tyr | Ile | Phe | Asn | Leu | Ala | Leu | Ala | Asp | Ala | Leu Val Thr Thr Thr Met |
| | | | | 100 | | | | 105 | | | 110 |

HUMAN  Pro Phe Gln Ser Thr Val Tyr Leu Met Asn Ser Trp Pro Phe Gly Asp
MOUSE  Pro Phe Gln Ser Ala Val Tyr Leu Met Asn Ser Trp Pro Phe Gly Asp
                 115                 120                 125

HUMAN  Val Leu Cys Lys Ile Val Ile Ser Ile Asp Tyr Tyr Asn Met Phe Thr
MOUSE  Val Leu Cys Lys Ile Val Ile Ser Ile Asp Tyr Tyr Asn Met Phe Thr
                 130                 135                 140

HUMAN  Ser Ile Phe Thr Leu Thr Met Met Ser Val Asp Arg Tyr Ile Ala Val
MOUSE  Ser Ile Phe Thr Leu Thr Met Met Ser Val Asp Arg Tyr Ile Ala Val
                 145                 150                 155                 160

HUMAN  Cys His Pro Val Lys Ala Leu Asp Phe Arg Thr Pro Leu Lys Ala Lys
MOUSE  Cys His Pro Val Lys Ala Leu Asp Phe Arg Thr Pro Leu Lys Ala Lys
                 165                 170                 175

UMAN   Ile Ile Asn Ile Cys Ile Trp Leu Leu Ser Ser Ser Val Gly Ile Ser
MOUSE  Ile Ile Asn Ile Cys Ile Trp Leu Leu Ser Ala Ser Val Gly Ile Ser
                 180                 185                 190

FIG. 4A-2

| | | | | | | | | | | | | | | |
|---|---|---|---|---|---|---|---|---|---|---|---|---|---|---|
HUMAN | Ala | Ile | Val | Leu | Gly | Gly | Thr | Lys | Val | Arg | Glu | Asp | Val | Ile
MOUSE | Ala | Ile | Val | Leu | Gly | Gly | Thr | Lys | Val | Arg | Glu | Asp | Val | Ile
| | 195 | | | | | | 200 | | | | | 205 | |

HUMAN | Glu | Cys | Cys | Leu | Gln | Phe | Pro | Asp | Asp | Tyr | Ser | Trp | Trp | Asp | Leu
MOUSE | Glu | Cys | Cys | Ser | Leu | Gln | Phe | Pro | Asp | Asp | Tyr | Ser | Trp | Trp | Asp | Leu
| | 210 | | | | | 215 | | | | | 220 | | |

HUMAN | Phe | Met | Lys | Ile | Cys | Val | Phe | Ile | Phe | Ala | Phe | Val | Ile | Pro | Val | Leu
MOUSE | Phe | Met | Lys | Ile | Cys | Val | Phe | Val | Phe | Ala | Phe | Val | Ile | Pro | Val | Leu
| | 225 | | | | 230 | | | | | 235 | | | | 240

HUMAN | Ile | Ile | Ile | Val | Cys | Tyr | Thr | Leu | Met | Ile | Leu | Arg | Leu | Lys | NNN | Val
MOUSE | Ile | Ile | Ile | Val | Cys | Tyr | Thr | Leu | Met | Ile | Leu | Arg | Leu | Lys | Ser | Val
| | | | | 245 | | | | 250 | | | | | 255

HUMAN | Arg | Leu | Leu | Ser | Gly | Ser | Arg | Glu | Lys | Asp | NNN | Asn | Leu | Arg | Arg | Ile
MOUSE | Arg | Leu | Leu | Ser | Gly | Ser | Arg | Glu | Lys | Asp | Arg | Asn | Leu | Arg | Arg | Ile
| | | 260 | | | | | 265 | | | | | 270 |

FIG. 4A-3

| | | | | | | | | | |
|---|---|---|---|---|---|---|---|---|---|
| HUMAN | Thr | Arg | Leu | Val | Leu | Val | Val | Ala | Val | Phe | Val | Val | Cys | Trp | Thr |
| MOUSE | Thr | Lys | Leu | Val | Leu | Val | Val | Ala | Val | Phe | Ile | Ile | Cys | Trp | Thr |

(positions 275, 280, 285)

| | | | | | | | | | |
|---|---|---|---|---|---|---|---|---|---|
| HUMAN | Pro | Ile | His | Ile | Phe | Ile | Leu | Val | Glu | Ala | Leu | Gly | Ser | Thr | Ser | His |
| MOUSE | Pro | Ile | His | Ile | Phe | Ile | Leu | Val | Glu | Ala | Leu | Gly | Ser | Thr | Ser | His |

(positions 290, 295, 300)

| | | | | | | | | | |
|---|---|---|---|---|---|---|---|---|---|
| HUMAN | Ser | Thr | Ala | Ala | Leu | Ser | Ser | Tyr | Tyr | Phe | Cys | Ile | Ala | Leu | Gly | Tyr |
| MOUSE | Ser | Thr | Ala | Ala | Leu | Ser | Ser | Tyr | Tyr | Phe | Cys | Ile | Ala | Leu | Gly | Tyr |

(positions 305, 310, 315, 320)

| | | | | | | | | | |
|---|---|---|---|---|---|---|---|---|---|
| HUMAN | Thr | Asn | Ser | Ser | Leu | Asn | Pro | Ile | Leu | Tyr | Ala | Phe | Leu | Asp | Glu | Asn |
| MOUSE | Thr | Asn | Ser | Ser | Leu | Asn | Pro | Val | Leu | Tyr | Ala | Phe | Leu | Asp | Glu | Asn |

(positions 325, 330, 335)

FIG. 4B-1

```
HUMAN  Phe Lys Arg Cys Phe Arg Asp Phe Cys Phe Pro Leu Lys Met NNN Met
MOUSE  Phe Lys Arg Cys Phe Arg Asp Phe Cys Phe Pro Ile Lys Met Arg Met
                       340                 345                 350

HUMAN  Glu Arg NNN Ser Thr Ser Arg Val Arg Asn Thr Val Gln Asp Pro Ala
MOUSE  Glu Arg Gln Ser Thr Asn Arg Val Arg Asn Thr Val Gln Asp Pro Ala
                       355                 360                 365

HUMAN  Tyr Leu Arg Glu Ile Asp Gly Met Met Asn Lys Pro Val  (SEQ ID NO:12)
MOUSE  Ser Met Arg Asp Val Gly Gly Met Asn Lys Pro Val      (SEQ ID NO:2)
                       370                 375                 380
```

FIG. 4B-2

POLYNUCLEOTIDES ENCODING KAPPA OPIOD RECEPTORS

CROSS-REFERENCE TO RELATED APPLICATION

This application is a Continuation-In-Part of U.S. patent application Ser. No. 08/100,694, filed Jul. 30, 1993, abandoned, which application was a Continuation-In-Part of U.S. patent application Ser. No. 08/066,296, filed May 20, 1993, abandoned, the disclosure of which is incorporated herein by reference.

RELATED OWNERSHIP RIGHTS

The research for the information disclosed herein was supported by the Howard Hughes Medical Institute, American Diabetes Association and United States Public Health Service Grants DK-20595, DK-42086, MH-45533 and MH-48518. These organizations and the United States government may own certain rights to the invention disclosed herein.

FIELD OF THE INVENTION

This invention relates generally to compositions of and methods for obtaining opioid receptors. The invention relates as well to the DNA sequences encoding opioid receptors, the recombinant vectors carrying those sequences, the recombinant host cells including either the sequences or vectors, and recombinant opioid receptor polypeptides. The invention includes as well methods for using the isolated, recombinant receptor polypeptides in assays designed to select and improve among candidate substances such as agonists and antagonists of opioid receptors and polypeptides for use in diagnostic, drug design and therapeutic applications.

BACKGROUND OF THE INVENTION

Opioid drugs have various effects on perception of pain, consciousness, motor control, mood, and autonomic function and can also induce physical dependence (Koob, et al 1992). The endogenous opioid system plays an important role in modulating endocrine, cardiovascular, respiratory, gastrointestinal and immune functions (Olson, et al 1989). Opioids exert their actions by binding to specific membrane-associated receptors located throughout the central and peripheral nervous system (Pert, et al. 1973). The endogenous ligands of these opioid receptors have been identified as a family of more than 20 opioid peptides that derive from the three precursor proteins proopiomelanocortin, proenkephalin, and prodynorphin (Hughes, et al. (1975); Akil, et al. (1984)). Although the opioid peptides belong to a class of molecules distinct from the opioid alkaloids, they share common structural features including a positive charge juxtaposed with an aromatic ring that is required for interaction with the receptor (Bradbury, et al. (1976)).

Pharmacological studies have suggested that there are at least four major classes of opioid receptors, designated δ, κ, μ and σ (Simon 1991; Lutz, et al. 1992). The classes differ in their affinity for various opioid ligands and in their cellular distribution. The different classes of opioid receptors are believed to serve different physiological functions (Olson, et al., 1989, Simon 1991; Lutz & Pfister 1992). However, there is substantial overlap of function as well as of distribution. Biochemical characterization of opioid receptors from many groups reports a molecular mass of ≈60,000 Da for all three subtypes, suggesting that they could be related molecules (Loh, et al. (1990)). Moreover, the similarity between the three receptor subtypes is supported by the isolation of (i) antiidiotypic monoclonal antibodies competing with both μ and δ ligands but not competing with κ ligands (Gramsch, et al. (1988), Coscia, et al. (1991)) and (ii) a monoclonal antibody raised against the purified μ receptor that interacts with both μ and κ receptors (Bero, et al. (1988)).

Opioids are used clinically in the management of pain, but their use is limited by a constellation of undesirable side effects, including respiratory depression, miosis, decreased gastrointestinal motility, sedation, nausea and vomiting (Jaffe et al., 1990). A concern of the use of opioids in the treatment of chronic pain is their potential for dependence and abuse. Studies suggest the clinical effects of opioids are mediated via a variety of receptors and that the therapeutic effects and the undesirable side effects of opioids are mediated by different receptor (sub)types (Jaffe et al., 1990; Pasternack, 1993). Therefore, the therapeutic and side effects of opioids can be separated with the use of more selective agents for receptor subtypes. In the present study, we have characterized the pharmacological properties of the cloned κ, δ, and μ opioid receptors and characterized the receptor selectivity of widely employed opioid ligands The δ receptors bind with the greatest affinity to enkephalins and have a more discrete distribution in the brain than either μ or κ receptors, with high concentrations in the basal ganglia and limbic regions. Although morphine interacts principally with μ receptors, peripheral administration of this opioid induces release of enkephalins (Bertolucci, et al. (1992)). Thus, enkephalins may mediate part of the physiological response to morphine, presumably by interacting with δ receptors. Despite pharmacological and physiological heterogeneity, at least some types of opioid receptors inhibit adenylate cyclase, increase $K^+$ conductance, and inactivate $Ca^{2+}$ channels through a pertussis toxin-sensitive mechanism (Puttfarcken, et al. 1988; Attali, et al. 1989; Hsia, et al., 1984). These results and others suggest that opioid receptors belong to the large family of cell surface receptors that signal through G proteins (Di Chiara, et al. (1992); Loh, et al. (1990)).

Several attempts to clone cDNAs encoding opioid receptors have been reported. A cDNA encoding an opioid-binding protein (OBCAM) with μ selectivity was isolated (Schofield, et al. (1989)), but the predicted protein lacked transmembrane domains, presumed necessary for signal transduction. More recently, the isolation of another cDNA was reported, which was obtained by expression cloning (Xie, et al. (1992)). The deduced protein sequence displays seven putative transmembrane domains and is very similar to the human neuromedin K receptor. However, the affinity of opioid ligands for this receptor expressed in COS cells is two orders of magnitude below the expected value, and no subtype selectivity can be shown.

Many cell surface receptor/transmembrane systems consist of at least three membrane-bound polypeptide components: (a) a cell-surface receptor; (b) an effector, such as an ion channel or the enzyme adenylate cyclase; and (c) a guanine nucleotide-binding regulatory polypeptide or G protein, that is coupled to both the receptor and its effector.

G protein-coupled receptors mediate the actions of extracellular signals as diverse as light, odorants, peptide hormones and neurotransmitters. Such receptors have been identified in organisms as evolutionarily divergent as yeast and man. Nearly all G protein-coupled receptors bear sequence similarities with one another, and it is thought that all share a similar topological motif consisting of seven hydrophobic (and potentially α-helical) segments that span the lipid bilayer (Dohlman et al. 1987; Dohlman et al. 1991).

G proteins consist of three tightly associated subunits, α, β and γ (1:1:1) in order of decreasing mass. Following agonist binding to the receptor, a conformational change is transmitted to the G protein, which causes the Gα-subunit to exchange a bound GDP for GTP and to dissociate from the βγ-subunits. The GTP-bound form of the α-subunit is typically the effector-modulating moiety. Signal amplification results from the ability of a single receptor to activate many G protein molecules, and from the stimulation by Gα-GTP of many catalytic cycles of the effector.

The family of regulatory G proteins comprises a multiplicity of different α-subunits (greater than twenty in man), which associate with a smaller pool of β- and γ-subunits (greater than four each) (Strothman and Simon 1991). Thus, it is anticipated that differences in the α-subunits probably distinguish the various G protein oligomers, although the targeting or function of the various α-subunits might also depend on the β and γ subunits with which they associate (Strothman and Simon 1991).

Improvements in cell culture and in pharmacological methods, and more recently, use of molecular cloning and gene expression techniques, have led to the identification and characterization of many seven-transmembrane segment receptors, including new sub-types and sub-sub-types of previously identified receptors. The $\alpha_1$ and $\alpha_2$-adrenergic receptors, once thought to each consist of single receptor species, are now known to each be encoded by at least three distinct genes (Kobilka et al. 1987; Regan et al. 1988; Cotecchia et al. 1988; Lomasney 1990). In addition to rhodopsin in rod cells, which mediates vision in dim light, three highly similar cone pigments mediating color vision have been cloned (Nathans et al. 1986A; and Nathans et al. 1986B). All of the family of G protein-coupled receptors appear to be similar to other members of the family of G protein-coupled receptors (e.g., dopaminergic, muscarinic, serotonergic, tachykinin, etc.), and each appears to share the characteristic seven-transmembrane segment topography.

When comparing the seven-transmembrane segment receptors with one another, a discernible pattern of amino acid sequence conservation is observed. Transmembrane domains are often the most similar, whereas the amino and carboxyl terminal regions and the cytoplasmic loop connecting transmembrane segments V and VI can be quite divergent (Dohlman et al. 1987).

Interaction with cytoplasmic polypeptides, such as kinases and G proteins, was predicted to involve the hydrophobic loops connecting the transmembrane domains of the receptor. The challenge, however, has been to determine which features are preserved among the seven-transmembrane segment receptors because of conservation of function, and which divergent features represent structural adaptations to new functions. A number of strategies have been used to test these ideas, including the use of recombinant DNA and gene expression techniques for the construction of substitution and deletion mutants, as well as of hybrid or chimeric receptors (Dohlman et al. 1991).

With the growing number of receptor sub-types, G-protein subunits, and effectors, characterization of ligand binding and G protein recognition properties of these receptors is an important area for investigation. It has long been known that multiple receptors can couple to a single G protein and, as in the case of epinephrine binding to $\beta_2$- and $\alpha_2$-adrenergic receptors, a single ligand can bind to multiple, functionally-distinct, receptor sub-types. Moreover, G proteins with similar receptor and effector coupling specificities have also been identified. For example, three species of human $G_i$ have been cloned (Itoh et al. 1988), and alternate mRNA splicing has been shown to result in multiple variants of $G_s$ (Kozasa et al. 1988). Cloning and over production of the muscarinic and $\alpha_2$-adrenergic receptors led to the demonstration that a single receptor sub-type, when expressed at high levels in the cell, will couple to more than one type of G protein.

Opioid receptors are known to be sensitive to reducing agents, and the occurrence of a disulfide bridge has been postulated as essential for ligand binding (Gioannini, et al. 1989). For rhodopsin, muscarinic, and β-adrenergic receptors, two conserved cysteine residues in each of the two first extracellular loops have been shown to be critical for stabilizing the functional protein structure and are presumed to do so by forming a disulfide bridge. Structure/function studies of opioid ligands have shown the importance of a protonated amine group for binding to the receptor with high affinity. The binding site of the receptor might, therefore, possess a critical negatively charged counterpart. Catecholamine receptors display in their sequence a conserved aspartate residue that has been shown necessary for binding the positively charged amine group of their ligands.

Given the complexity and apparent degeneracy of function of various opioid receptors, a question of fundamental importance is how, and under what circumstances, do specific sub-type and sub-sub-type receptors exert their physiological effect in the presence of the appropriate stimulatory ligand. A traditional approach to answering this question has been to reconstitute the purified receptor and G protein components in vitro. Unfortunately, purification schemes have been successful for only a very limited number of receptor sub-types and their cognate G-proteins. Alternatively, heterologous expression systems can be of more general usefulness in the characterization of cloned receptors and in elucidating receptor G protein coupling specificity (Marullo et al. 1988; Payette et al. 1990; King et al. 1990).

One such system was recently developed in yeast cells, in which the genes for a mammalian $\beta_2$-adrenergic receptor and $G_s$ α-subunit were co-expressed (King et al. 1990). Expression of the $\beta_2$-adrenergic receptor to levels several hundred-fold higher than in any human tissue was attained, and ligand binding was shown to be of the appropriate affinity, specificity, and stereoselectivity. Moreover, a $\beta_2$-adrenergic receptor-mediated activation of the pheromone signal transduction pathway was demonstrated by several criteria, including imposition of growth arrest, morphological changes, and induction of a pheromone-responsive promoter (FUSI) fused to the *Escherichia coli* lacz gene (encoding β-galactosidase) (King et al. 1990).

Finally, expression of a single receptor in the absence of other related sub-types is often impossible to achieve, even in isolated, non-recombinant mammalian cells. Thus, there has been considerable difficulty in applying the standard approaches of classical genetics or even the powerful techniques of molecular biology to the study of opioid receptors. In particular, means are needed for the identification of the DNA sequences encoding individual opioid receptors. Given such isolated, recombinant sequences, it is possible to address the heretofore intractable problems associated with design and testing of isoform-specific opioid receptor agonists and antagonists. The availability of cDNAs encoding the opioid receptors will permit detailed studies of signal-transduction mechanisms and reveal the anatomical distribution of the mRNAs of these receptors, providing information on their expression pattern in the nervous system. This information should ultimately allow better understanding of the opioid system in analgesia, and also the design of more specific therapeutic drugs.

Availability of polynucleotide sequences encoding opioid receptors, and the polypeptide sequences of the encoded receptors, will significantly increase the capability to design pharmaceutical compositions, such as analgesics, with enhanced specificity of function. In general, the availability of these polypeptide sequences will enable efficient screening of candidate compositions. The principle in operation through the screening process is straightforward: natural agonists and antagonists bind to cell-surface receptors and channels to produce physiological effects; certain other molecules bind to receptors and channels; therefore, certain other molecules may produce physiological effects and act as therapeutic pharmaceutical agents. Thus, the ability of candidate drugs to bind to opioid receptors can function as an extremely effective screening criterion for the selection of pharmaceutical compositions with a desired functional efficacy.

Prior methods for screening candidate drug compositions based on their ability to preferentially bind to cell-surface receptors has been limited to tissue-based techniques. In these techniques, animal tissues rich in the receptor type of interest are extracted and prepared; candidate drugs are then allowed to interact with the prepared tissue and those found to bind to the receptors are selected for further study. However, these tissue-based screening techniques suffer from several significant disadvantages. First, they are expensive because the source of receptor cell tissue—laboratory animals—is expensive. Second, extensive technical input is required to operate the screens. And, third, the screens may confuse the results because there are no tissues where only one receptor subtype is expressed exclusively. With traditional prior art screens you are basically looking at the wrong interactions or, at best, the proper interactions mixed in with a whole variety of unwanted interactions. An additional fundamental deficiency of animal tissue screens is that they contain animal receptors—ideal for the development of drugs for animals but of limited value in human therapeutic agents.

The solution to this problem is provided by the present invention. A polynucleotide of the present invention, transfected into suitable host cells, can express polypeptide sequences corresponding to opioid receptors, both in large quantities and through relatively simple laboratory procedures. The result is the availability of extremely specific receptor-drug interactions free from the competitive and unwanted interactions encountered in tissue-based screens. Further expression in a microorganism where no such endogenous receptors exist (e.g. yeast cells or mutant mammalian cell lines) can be useful for screening and evaluating sub-type-selective drugs (Marullo et al. 1988; Payette et al. 1990; and King et al. 1990).

BRIEF SUMMARY OF THE INVENTION

In one aspect, the present invention provides an isolated and purified polynucleotide that encodes an opioid receptor polypeptide. In a preferred embodiment, a polynucleotide of the present invention is a DNA molecule. More preferably, a polynucleotide of the present invention encodes a polypeptide that is a delta, kappa, mu or sigma opioid receptor. Even more preferred, a polynucleotide of the present invention encodes a polypeptide comprising the amino acid residue sequence of SEQ ID NO:2, SEQ ID NO:4 or SEQ ID NO:12. Most preferably, an isolated and purified polynucleotide of the invention comprises the nucleotide base sequence of SEQ ID NO:1, SEQ ID NO:3 or SEQ ID NO:11.

Yet another aspect of the present invention contemplates an isolated and purified polynucleotide comprising a base sequence that is identical or complementary to a segment of at least 10 contiguous bases of SEQ ID NO:1 or SEQ ID NO:11, wherein the polynucleotide hybridizes to a polynucleotide that encodes an opioid receptor polypeptide. Preferably, the isolated and purified polynucleotide comprises a base sequence that is identical or complementary to a segment of at least 25 to 70 contiguous bases of SEQ ID NO:1 or SEQ ID NO: 11. For example, the polynucleotide of the invention can comprise a segment of bases identical or complementary to 40 or 55 contiguous bases of the disclosed nucleotide sequences.

In still another embodiment of the present invention, there is provided an isolated and purified polynucleotide comprising a base sequence that is identical or complementary to a segment of at least 10 contiguous bases of SEQ ID NO:3. The polynucleotide of the invention hybridizes to SEQ ID NO:3, or a complement of SEQ ID NO:3. Preferably, the isolated and purified polynucleotide comprises a base sequence that is identical or complementary to a segment of at least 25 to 70 contiguous bases of SEQ ID NO:3. For example, the polynucleotide of the invention can comprise a segment of bases identical or complementary to 40 or 55 contiguous bases of SEQ ID NO:3.

In another embodiment, the present invention contemplates an isolated and purified opioid receptor polypeptide. Preferably, an opioid receptor polypeptide of the invention is a recombinant polypeptide. More preferably, an opioid receptor polypeptide of the present invention is delta, kappa, mu or sigma opioid receptor polypeptide. Even more preferably, an opioid receptor polypeptide of the present invention comprises the amino acid residue sequence of SEQ ID NO:2, SEQ ID NO:4 or SEQ ID NO: 12.

In an alternative embodiment, the present invention provides an expression vector comprising a polynucleotide that encodes an opioid receptor polypeptide. Preferably, an expression vector of the present invention comprises a polynucleotide that encodes a polypeptide comprising the amino acid residue sequence of SEQ ID NO:2, SEQ ID NO:4 or SEQ ID NO: 12. More preferably, an expression vector of the present invention comprises a polynucleotide comprising the nucleotide base sequence of SEQ ID NO:1, SEQ ID NO:3 or SEQ ID NO: 11. Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter, and the expression vector further comprises a polyadenylation signal that is positioned 3' of the carboxy-terminal amino acid and within a transcriptional unit of the encoded polypeptide.

In yet another embodiment, the present invention provides a recombinant host cell transfected with a polynucleotide that encodes an opioid receptor polypeptide. Preferably, a recombinant host cell of the present invention is transfected with the polynucleotide of SEQ ID NO:1, SEQ ID NO:3 or SEQ ID NO: 11. In one aspect, a host cell of the invention is a eukaryotic host cell. A recombinant host cell of the present invention can be a yeast cell. Preferably, a recombinant host cell of the invention is a PC12 or CHO-G44 cell.

In another aspect, a recombinant host cell of the present invention is a prokaryotic host cell. Preferably, a recombinant host cell of the invention is a bacterial cell of the DH5α strain of *Escherichia coli*. More preferably, a recombinant host cell comprises a polynucleotide under the transcriptional control of regulatory signals functional in the recombinant host cell, wherein the regulatory signals appropriately control expression of an opioid receptor polypeptide in a manner to enable all necessary transcriptional and post-transcriptional modification.

In yet another embodiment, the present invention contemplates a process of preparing an opioid receptor polypeptide comprising transfecting a cell with polynucleotide that encodes an opioid receptor polypeptide to produce a transformed host cell; and maintaining the transformed host cell under biological conditions sufficient for expression of the polypeptide. Preferably, the transformed host cell is a eukaryotic cell. More preferably still, the eukaryotic cell is a COS-1 cell. Alternatively, the host cell is a prokaryotic cell. More preferably, the prokaryotic cell is a bacterial cell of the DH5α strain of *Escherichia coli*. Even more preferably, a polynucleotide transfected into the transformed cell comprises the nucleotide base sequence of SEQ ID NO:2, SEQ ID NO:4 or SEQ ID NO: 11.

In still another embodiment, the present invention provides an antibody immunoreactive with an opioid receptor polypeptide. Preferably, an antibody of the invention is a monoclonal antibody. More preferably, an opioid receptor polypeptide comprises the amino acid residue sequence of SEQ ID NO: 12.

In another aspect, the present invention contemplates a process of producing an antibody immunoreactive with an opioid receptor polypeptide comprising the steps of (a) transfecting a recombinant host cell with a polynucleotide that encodes an opioid receptor polypeptide; (b) culturing the host cell under conditions sufficient for expression of the polypeptide; (c) recovering the polypeptide; and (d) preparing the antibody to the polypeptide. Preferably, the host cell is transfected with the polynucleotide of SEQ ID NO:1, SEQ ID NO:3 or SEQ ID NO: 11. Even more preferably, the present invention provides an antibody prepared according to the process described above.

Alternatively, the present invention provides a process of detecting an opioid receptor polypeptide, wherein the process comprises immunoreacting the polypeptide with an antibody prepared according to the process described above, to form an antibody-polypeptide conjugate, and detecting the conjugate.

In yet another embodiment, the present invention contemplates a process of detecting a messenger RNA transcript that encodes an opioid receptor polypeptide, wherein the process comprises (a) hybridizing the messenger RNA transcript with a polynucleotide sequence that encodes the opioid receptor polypeptide to form a duplex; and (b) detecting the duplex. Alternatively, the present invention provides a process of detecting a DNA molecule that encodes an opioid receptor polypeptide, wherein the process comprises (a) hybridizing DNA molecules with a polynucleotide that encodes an opioid receptor polypeptide to form a duplex; and (b) detecting the duplex.

In another aspect, the present invention contemplates a diagnostic assay kit for detecting the presence of an opioid receptor polypeptide in a biological sample, where the kit comprises a first container containing a first antibody capable of immunoreacting with an opioid receptor polypeptide, with the first antibody present in an amount sufficient to perform at least one assay. Preferably, an assay kit of the invention further comprises a second container containing a second antibody that immunoreacts with the first antibody. More preferably, the antibodies used in an assay kit of the present invention are monoclonal antibodies. Even more preferably, the first antibody is affixed to a solid support. More preferably still, the first and second antibodies comprise an indicator, and, preferably, the indicator is a radioactive label or an enzyme.

In an alternative aspect, the present invention provides a diagnostic assay kit for detecting the presence, in biological samples, of a polynucleotide that encodes an opioid receptor polypeptide, the kits comprising a first container that contains a second polynucleotide identical or complementary to a segment of at least 10 contiguous nucleotide bases of SEQ ID NO:1, SEQ ID NO:3 or SEQ ID NO: 11.

In another embodiment, the present invention contemplates a diagnostic assay kit for detecting the presence, in a biological sample, of an antibody immunoreactive with an opioid receptor polypeptide, the kit comprising a first container containing an opioid receptor polypeptide that immunoreacts with the antibody, with the polypeptide present in an amount sufficient to perform at least one assay.

In yet another aspect, the present invention contemplates a process of screening substances for their ability to interact with an opioid receptor polypeptide comprising the steps of providing an opioid receptor polypeptide, and testing the ability of selected substances to interact with the opioid receptor polypeptide. In a preferred embodiment, the opioid receptor polypeptide is a chimeric opioid receptor polypeptide. More preferably, the chimeric opioid receptor polypeptide is a $\kappa_{1-74}/\delta_{65-372}$ chimeric opioid receptor polypeptide.

In another embodiment, the opioid receptor polypeptide is a mutant opioid receptor polypeptide and, more preferably a mouse delta opioid receptor polypeptide having an asparagine at residue 95 instead of an aspartate.

In a preferred embodiment, providing an opioid receptor polypeptide is transfecting a host cell with a polynucleotide that encodes an opioid receptor polypeptide to form a transformed cell and maintaining the transformed cell under biological conditions sufficient for expression of the opioid receptor polypeptide.

In another aspect, the present invention provides an isolated and purified polynucleotide that encodes a truncated opioid receptor polypeptide. Preferably, the opioid receptor is a kappa or a delta opioid receptor polypeptide. In another embodiment, the opioid receptor comprises amino acid residues 79 to 380 of a kappa opioid receptor polypeptide or amino acid residues 70 to 372 of a delta opioid receptor polypeptide.

In yet another aspect, the present invention provides an isolated and purified polynucleotide that encodes a chimeric opioid receptor polypeptide. Preferably, that chimeric is designated as $\kappa_{1-78}/\delta_{70-372}$, $\delta_{1-69}/\kappa_{79-380}$, $\kappa_{1-74}/\delta_{65-372}$ $\delta_{1-64}/\kappa_{75-380}$.

The present invention also provides an isolated and purified truncated opioid receptor polypeptide. Preferably, that polypeptide is a kappa or a delta opioid receptor polypeptide, and more preferably, that polypeptide comprises amino acid residues 79 to 380 of a kappa opioid receptor polypeptide or amino acid residues 70 to 372 of a delta opioid receptor polypeptide.

The present invention also provides an isolated and purified chimeric opioid receptor polypeptide. That chimeric is preferably designated as $\kappa_{1-78}/\delta_{70-372}$, $\delta_{1-69}/\kappa_{79-380}$, $\kappa_{1-74}/\delta_{65-372}$ or $\delta_{1-64}/\kappa_{75-380}$.

The present invention further provides a process of screening a substance for its ability to interact with an opioid receptor, the process comprising the steps of:

a) providing a chimeric opioid receptor polypeptide; and b) testing the ability of the substance to interact with the chimeric opioid receptor polypeptide. A preferred chimeric is the same as set forth above.

The present invention still further provides a process of screening a substance for its ability to interact with an opioid receptor, the process comprising the steps of:

a) providing a truncated opioid receptor polypeptide; and b) testing the ability of the substance to interact with the truncated opioid receptor polypeptide. A preferred truncated receptor polypeptide is the same as set forth above.

BRIEF DESCRIPTION OF THE DRAWINGS

In the drawings, which form a portion of the specification:

FIG. 1 shows a comparison of amino acid sequences of mouse kappa/msl-1 (mORK1) and delta/msl-2 (mORD1) opioid receptors. Asterisks denote identical amino acids, and bars indicate similar residues. Gaps introduced to generate this alignment are represented by colons. The seven predicted transmembrane domains (TM1–TM7) are noted. The potential sites for N-linked glycosylation in the $NH_2$-terminal extracellular domain are underlined. There are potential phosphorylation sites for cAMP dependent protein kinase in mORK1 and mORD1 at residues 274 and 260, respectively. Potential protein kinase C phosphorylation sites are present in mORK1 at residues 242, 255, 344 and 352, and in mORD1 at residues 255, 357 and 369.

FIG. 3A, FIG. 3B and FIG. 3C shows a partial genomic sequence for a human kappa opioid receptor. Intron 1 begins at residue 1 and ends at residue 101. Intron 2 begins at residue 454. The length of intron 2 is undetermined presently. The 13 colons after residue 455 does not represent 13 unknown nucleotides. The colons signify that intron 2 contains more nucleotide residues than is set out in FIG. 4a and 4b starts at residue 503 and ends at residue 435. The stop codon begins at residue 436. In exon 2, there are several undetermined nucleotide residues. These residues are at 656, 657, 691, 692, 945, and 955.

FIG. 4A, FIG. 4B and FIG. 4C, shows comparison of the amino acid sequences of human kappa and mouse kappa/msl-1 (mORK1) opioid receptors. Gaps introduced to generate this alignment are represented by colons. Amino acid residues 255, 267, 351 and 355 are unidentified because the corresponding nucleotide sequences are as yet unidentified. The mouse sequence begins with amino acid residue 1, and the human sequence begins with amino acid residue 87.

FIG. 5A, FIG. 5B, FIG. 5C, FIG. 5D, FIG. 5E and FIG. 5F, show saturable binding of [$^3$H]U-69,593, ([$^3$H]) naltrindole, or [$^3$H]DAMGO to the cloned κ, δ and $\mu$ opioid receptors. Membranes from PC12 cells stably expressing the cloned κ receptor (FIG. 5A), CHO-DG44 cells stably expressing the cloned δ receptor (FIG. 5B), or COS-7 cells transiently expressing the cloned $\mu$ receptor (FIG. 5C) were incubated for 40 min at 25° C. with increasing concentrations of [$^3$H]U-69,593, [$^3$H]naltrindole, or [$^3$H]DAMGO, respectively, in the presence (Δ) or absence (□) of 10 $\mu$M naloxone in order to determine specific binding (●). Upper, saturation isotherms of representative experiments; lower, linearization of the saturation isotherm data. Analysis of the saturable binding to the κ receptor revealed that [$^3$H]U-69,593 bound to a single site with a $K_D$ of 2.8 nM and a $B_{max}$ of 3346 fmol/mg protein. Analysis of the saturable binding to the δ receptor revealed that [$^3$H]DAMGO bound to a single site with a $K_D$ of 0.18 nM and a $B_{max}$ of 633 fmol/mg protein. Analysis of the saturable binding to the $\mu$ receptor revealed that [$^3$H]DAMGO bound to a single site with a $K_D$ of 0.57 nM and a $B_{max}$ of 444 fmol/mg protein. Experiments were conducted in triplicate and the results of two to three independent experiments were similar.

DETAILED DESCRIPTION OF THE INVENTION

I. The Invention

Figure 2A:
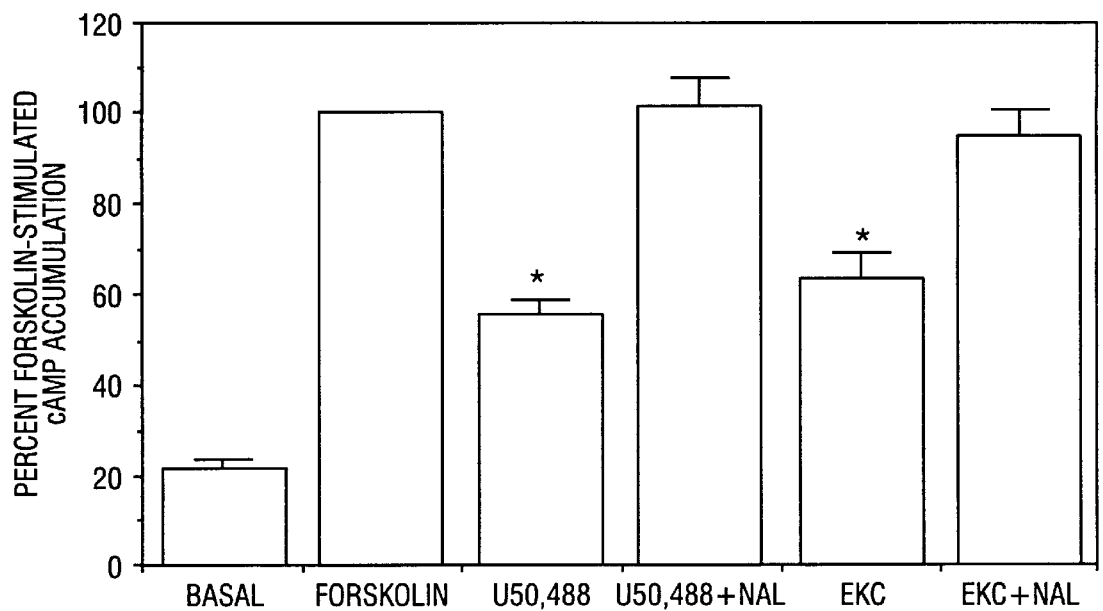
FIG. 2A and FIG. 2B show that mouse kappa/msl-1 (FIG. 2A) and delta/msl-2 (FIG. 2B) opioid receptors mediate opioid inhibition of cAMP formation. COS-1 cells transiently expressing mouse kappa and delta opioid receptors were treated with forskolin (10 $\mu$M)±1 $\mu$M opioid agonist or 1 $\mu$M agonist and 10 $\mu$M naloxone. For these studies, equal numbers of cells (5×10$^5$) were plated. In cells expressing kappa and delta opioid receptors, the basal cAMP levels were 40±3 p/mol/well and forskolin stimulated cAMP formation 5-fold (203±10 pmol/well). The values are expressed as percent of forskolin-stimulated cAMP formation and are the mean±SEM of three different experiments. The asterisks indicate significant (p<0.05) difference in cAMP levels between forskolin and opioid agonist/antagonist-treated cells. Nal, naloxone; EKC, ethylketocyclazocine.

The present invention provides DNA segments, purified polypeptides, methods for obtaining antibodies, methods of cloning and using recombinant host cells necessary to obtain and use recombinant opioid receptors. Thus, the difficulties encountered with applying the standard approaches of classical genetics or techniques in molecular biology evident in the prior art to opioid receptors, have been overcome. Accordingly, the present invention concerns generally compositions and methods for the preparation and use of opioid receptors.

II. Polynucleotide

A. Isolated and Purified Polynucleotide that Encode Opioid Receptor Polypeptides:

In one aspect, the present invention provides an isolated and purified polynucleotide that encodes an opioid receptor polypeptide. In a preferred embodiment, the polynucleotide of the present invention is a DNA molecule. More preferably, the polynucleotide of the present invention encodes polypeptides that are delta, kappa, mu or sigma opioid receptors. Even more preferred, a polynucleotide of the present invention encodes a polypeptide comprising the amino acid residue sequence of SEQ ID NO:2, SEQ ID NO:4 or SEQ ID NO:12. Most preferably, an isolated and purified polynucleotide of the invention comprises the nucleotide base sequence of SEQ ID NO:1, SEQ ID NO:3 or SEQ ID NO:11.

As used herein, the term "polynucleotide" means a sequence of nucleotides connected by phosphodiester linkages. Polynucleotides are presented herein in the direction from the 5' to the 3' direction. A polynucleotide of the present invention can comprise from about 680 to about several hundred thousand base pairs. Preferably, a polynucleotide comprises from about 680 to about 150,000 base pairs. Preferred lengths of particular polynucleotide are set forth hereinafter.

A polynucleotide of the present invention can be a deoxyribonucleic acid (DNA) molecule or ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), inosine (I) and uracil (U).

A polynucleotide of the present invention can be prepared using standard techniques well known to one of skill in the art. The preparation of a cDNA molecule encoding an opioid receptor polypeptide of the present invention is described hereinafter in Examples 1 and 2. A polynucleotide can also be prepared from genomic DNA libraries using lambda phage technologies.

In another aspect, the present invention provides an isolated and purified polynucleotide that encodes an opioid receptor polypeptide, where the polynucleotide is preparable by a process comprising the steps of constructing a library of cDNA clones from a cell that expresses the polypeptide; screening the library with a labelled cDNA probe prepared from RNA that encodes the polypeptide; and selecting a clone that hybridizes to the probe. Preferably, the polynucleotide of the invention is prepared by the above process. More preferably, the polynucleotide of the invention encodes a polypeptide that has the amino acid residue sequence of SEQ ID NO:2, SEQ ID NO:4 or SEQ ID NO:12. More preferably still, the polynucleotide comprises the nucleotide sequence of SEQ ID NO:1, SEQ ID NO:3 or SEQ ID NO:11.

B. Probes and Primers.

In another aspect, DNA sequence information provided by the present invention allows for the preparation of relatively short DNA (or RNA) sequences having the ability to specifically hybridize to gene sequences of the selected polynucleotide disclosed herein. In these aspects, nucleic acid probes of an appropriate length are prepared based on a consideration of a selected nucleotide sequence, e.g., a sequence such as that shown in SEQ ID NO:1, SEQ ID NO:3 or SEQ ID NO:11. The ability of such nucleic acid probes to specifically hybridize to a polynucleotide encoding an opioid receptor lends them particular utility in a variety of embodiments. Most importantly, the probes can be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a gene or polynucleotide that encodes an opioid receptor polypeptide from mammalian cells using polymerage chain reactive (PCR™) technology.

To provide certain of the advantages in accordance with the present invention, a preferred nucleic acid sequence employed for hybridization studies or assays includes probe molecules that are complementary to at least a 10 to 70 or so long nucleotide stretch of a polynucleotide that encodes an opioid receptor polypeptide, such as that shown in SEQ ID NO:1, SEQ ID NO:3 or SEQ ID NO: 11. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 25 to 40 nucleotides, 55 to 70 nucleotides, or even longer where desired. Such fragments can be readily prepared by, for example, directly synthesizing the fragment by chemical means, by application of nucleic acid reproduction technology, such as the PCR™ technology of U.S. Pat. No. 4,683,202, herein incorporated by reference, or by excising selected DNA fragments from recombinant plasmids containing appropriate inserts and suitable restriction enzyme sites.

In another aspect, the present invention contemplates an isolated and purified polynucleotide comprising a base sequence that is identical or complementary to a segment of at least 10 contiguous bases of SEQ ID NO:1, SEQ ID NO:3 or SEQ ID NO: 11, wherein the polynucleotide hybridizes to a polynucleotide that encodes an opioid receptor polypeptide. Preferably, the isolated and purified polynucleotide comprises a base sequence that is identical or complementary to a segment of at least 25 to 70 contiguous bases of SEQ ID NO:1, SEQ ID NO:3 or SEQ ID NO: 11. For example, the polynucleotide of the invention can comprise a segment of bases identical or complementary to 40 or 55 contiguous bases of the disclosed nucleotide sequences.

Accordingly, a polynucleotide probe molecule of the invention can be used for its ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids. For example, one will select relatively low salt and/or high temperature conditions, such as provided by 0.02 M–0.15 M NaCl at temperatures of 50° C. to 70° C. Those conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate an opioid receptor polypeptide coding sequence from other cells, functional equivalents, or the like, less stringent hybridization conditions are typically needed to allow formation of the heteroduplex. In these circumstances, one can desire to employ conditions such as 0.15 M–0.9 M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a polynucleotide of the present invention in combination with an appropriate label for detecting hybrid formation. A wide variety of appropriate labels are known in the art, including radioactive, enzymatic or other ligands, such as avidin/biotin, which are capable of giving a detectable signal.

In general, it is envisioned that a hybridization probe described herein is useful both as a reagent in solution hybridization as well as in embodiments employing a solid phase. In embodiments involving a solid phase, the test DNA (or RNA) is adsorbed or otherwise affixed to a selected matrix or surface. This fixed nucleic acid is then subjected to specific hybridization with selected probes under desired conditions. The selected conditions depend as is well known in the art on the particular circumstances and criteria required (e.g., on the G+C content, type of target nucleic acid, source of nucleic acid, size of hybridization probe). Following washing of the matrix to remove nonspecifically bound probe molecules, specific hybridization is detected, or even quantified, by means of the label.

II. Opioid Receptor Polypeptide

In one embodiment, the present invention contemplates an isolated and purified opioid receptor polypeptide. Preferably, an opioid receptor polypeptide of the invention is a recombinant polypeptide. More preferably, an opioid receptor polypeptide of the present invention is a delta, kappa, mu or sigma opioid receptor polypeptide. Even more preferably, an opioid receptor polypeptides of the present invention comprises the amino acid residue sequence of SEQ ID NO:2, SEQ ID NO:4 or SEQ ID NO: 12. An opioid receptor polypeptide preferably comprises less than about 500 amino acid residues and, more preferably less than about 400 amino acid residues.

Polypeptides are disclosed herein as amino acid residue sequences. Those sequences are written left to right in the direction from the amino to the carboxy terminus. In accordance with standard nomenclature, amino acid residue sequences are denominated by either a single letter or a three letter code as indicated below.

| Amino Acid Residue | 3-Letter Code | 1-Letter Code |
| --- | --- | --- |
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met |  |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Modifications and changes can be made in the structure of a polypeptide of the present invention and still obtain a molecule having like opioid receptor characteristics. For example, certain amino acids can be substituted for other amino acids in a sequence without appreciable loss of receptor activity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

In making such changes, the hydropathic index of amino acids can be considered. The importance of the hydropathic amino acid index in conferring interactive biologic function on a polypeptide is generally understood in the art (Kyte & Doolittle, J. Mol. Biol., 157:105–132, 1982). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. U.S. Pat. No. 4,554,101, incorporated herein by reference, states that the greatest local average hydrophilicity of a polypeptide, as governed by the hydrophilicity of its adjacent amino acids, correlates with its immunogenicity and antigenicity, i.e. with a biological property of the polypeptide.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine (See Table 1, below). The present invention thus contemplates functional or biological equivalents of an opioid receptor polypeptide as set forth above.

TABLE 1

| Original Residue | Exemplary Substitutions |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Met; Leu; Tyr |
| Ser | Thr |
| Thr | Ser |
| Trp | Tyr |
| Tyr | Trp; Phe |
| Val | Ile; Leu |

Biological or functional equivalents of a polypeptide can also be prepared using site-specific mutagenesis. Site-specific mutagenesis is a technique useful in the preparation of second generation polypeptides, or biologically functional equivalent polypeptides or peptides, derived from the sequences thereof, through specific mutagenesis of the underlying DNA. As noted above, such changes can be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by Adelman, et al. (1983). As will be appreciated, the technique typically employs a phage vector which can exist in both a single stranded and double stranded form. Typical vectors useful in site-directed mutagenesis include vectors such as the M13 phage (Messing, et al. 1981). These phage are commercially available and their use is generally known to those of skill in the art.

In general, site-directed mutagenesis in accordance herewith is performed by first obtaining a single-stranded vector which includes within its sequence a DNA sequence which encodes all or a portion of the opioid receptor polypeptide sequence selected. An oligonucleotide primer bearing the desired mutated sequence is prepared, generally synthetically, for example, by the method of Crea, et al. (1978). This primer is then annealed to the singled-stranded vector, and extended by the use of enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as E. coli cells and clones are selected which include recombinant vectors bearing the mutation. Commercially available kits come with all the reagents necessary, except the oligonucleotide primers.

An opioid receptor polypeptide of the present invention is understood to be any opioid receptor polypeptide capable of binding opioid in any of its forms or analogs of opioid. In addition, an opioid receptor polypeptide of the invention is not limited to a particular source. As disclosed herein, the techniques and compositions of the present invention provide, for example, the identification and isolation of msls 1–3 from mouse sources. Thus, the invention provides for the general detection and isolation of the genus of opioid receptor polypeptides from a variety of sources while identifying specifically three species of that genus. It is believed that a number of species of the family of opioid receptor polypeptides are amenable to detection and isolation using the compositions and methods of the present inventions. For example, the present invention also discloses A polypeptide of the present invention is prepared by standard techniques well known to those skilled in the art. Such techniques include, but are not limited to, isolation and purification from tissues known to contain that polypeptide, and express ion from cloned DNA that encodes such a polypeptide using transformed cells (See Examples 1 and 2, hereinafter).

In another embodiment, the present invention contemplates an opioid-like receptor polypeptide. Such a polypeptide comprises the amino acid residue sequence of SEQ ID NO. 6. A polynucleotide encoding, opioid-like receptor polypeptide comprises the nucleotide base sequence of SEQ ID NO. 5.

Opioid receptor polypeptides are found in virtually all mammals including human. The sequence of a mouse delta opiod receptor has been previously described (Kieffer, et al., 1992 and Evans, et al., 1992). As is the case with other receptors, there is likely little variation between the structure and function of opioid receptors in different species. Where there is a difference between species, identification of those differences is well within the skill of an artisan. Thus, the present invention contemplates an opioid receptor polypeptide from any mammal. A preferred mammal is a rodent or a human.

III. Expression Vectors

In an alternate embodiment, the present invention provides expression vectors comprising polynucleotide that encode opioid receptor polypeptides. Preferably, the expression vectors of the present invention comprise polynucleotide that encode polypeptides comprising the amino acid residue sequence of SEQ ID NO:2, SEQ ID NO 4 or SEQ ID NO: 12. More preferably, the expression vectors of the present invention comprise polynucleotide comprising the nucleotide base sequence of SEQ ID NO:1, SEQ ID NO:3 or SEQ ID NO: 11. Even more preferably, the expression vectors of the invention comprise polynucleotide operatively linked to an enhancer-promoter. More preferably still, the expression vectors of the invention comprise polynucleotide operatively linked to a prokaryotic promoter. Alternatively, the expression vectors of the present invention comprise polynucleotide operatively linked to an enhancer-promoter that is a eukaryotic promoter, and the expression vectors further comprise a polyadenylation signal that is positioned 3' of the carboxy-terminal amino acid and within a transcriptional unit of the encoded polypeptide.

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promotor is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell to be transfected. By employing an enhancer-promoter with well-known properties, the level and pattern of gene product expression can be optimized.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA). Transcription-terminating regions are well known in the art. A preferred transcription-terminating region used in an adenovirus vector construct of the present invention comprises a polyadenylation signal of SV40 or the protamine gene.

An expression vector comprises a polynucleotide that encodes an opioid receptor polypeptide. Such a polypeptide is meant to include a sequence of nucleotide bases encoding an opioid receptor polypeptide sufficient in length to distinguish said segment from a polynucleotide segment encoding a non-opioid receptor polypeptide. A polypeptide of the invention can also encode biologically functional polypeptides or peptides which have variant amino acid sequences, such as with changes selected based on considerations such as the relative hydropathic score of the amino acids being exchanged. These variant sequences are those isolated from natural sources or induced in the sequences disclosed herein using a mutagenic procedure such as site-directed mutagenesis.

Preferably, the expression vectors of the present invention comprise polynucleotide that encode polypeptides comprising the amino acid residue sequence of SEQ ID NO:2, SEQ ID NO:4 or SEQ ID NO: 12. An expression vector can include an opioid receptor polypeptide coding region itself of any of the opioid receptor polypeptides noted above or it can contain coding regions bearing selected alterations or modifications in the basic coding region of such an opioid receptor polypeptide. Alternatively, such vectors or fragments can code larger polypeptides or polypeptides which nevertheless include the basic coding region. In any event, it should be appreciated that due to codon redundancy as well as biological functional equivalence, this aspect of the invention is not limited to the particular DNA molecules corresponding to the polypeptide sequences noted above.

Exemplary vectors include the mammalian expression vectors of the pCMV family including pCMV6b and pCMV6c (Chiron Corp., Emeryville Calif.). In certain cases, and specifically in the case of these individual mammalian expression vectors, the resulting constructs can require co-transfection with a vector containing a selectable marker such as pSV2neo. Via co-transfection into a dihydrofolate reductase-deficient Chinese hamster ovary cell line, such as DG44, clones expressing opioid polypeptides by virtue of DNA incorporated into such expression vectors can be detected.

A DNA molecule of the present invention can be incorporated into a vector by a number of techniques which are well known in the art. For instance, the vector pUC18 has been demonstrated to be of particular value. Likewise, the related vectors M13mp18 and M13mp19 can be used in certain embodiments of the invention, in particular, in performing dideoxy sequencing.

An expression vector of the present invention is useful both as a means for preparing quantities of the opioid receptor polypeptide-encoding DNA itself, and as a means for preparing the encoded polypeptide and peptides. It is contemplated that where opioid receptor polypeptides of the invention are made by recombinant means, one can employ either prokaryotic or eukaryotic expression vectors as shuttle systems. However, in that prokaryotic systems are usually incapable of correctly processing precursor polypeptides and, in particular, such systems are incapable of correctly processing membrane associated eukaryotic polypeptides, and since eukaryotic opioid receptor polypeptides are anticipated using the teaching of the disclosed invention, one likely expresses such sequences in eukaryotic hosts. However, even where the DNA segment encodes a eukaryotic opioid receptor polypeptide, it is contemplated that prokaryotic expression can have some additional applicability. Therefore, the invention can be used in combination with vectors which can shuttle between the eukaryotic and prokaryotic cells. Such a system is described herein which allows the use of bacterial host cells as well as eukaryotic host cells.

Where expression of recombinant opioid receptor polypeptides is desired and a eukaryotic host is contemplated, it is most desirable to employ a vector such as a plasmid, that incorporates a eukaryotic origin of replication. Additionally, for the purposes of expression in eukaryotic systems, one desires to position the opioid receptor encoding sequence adjacent to and under the control of an effective eukaryotic promoter such as promoters used in combination with Chinese hamster ovary cells. To bring a coding sequence under control of a promoter, whether it is eukaryotic or prokaryotic, what is generally needed is to position the 5' end of the translation initiation side of the proper translational reading frame of the polypeptide between about 1 and about 50 nucleotides 3' of or downstream with respect to the promoter chosen. Furthermore, where eukaryotic expression is anticipated, one would typically desire to incorporate into the transcriptional unit which includes the opioid receptor polypeptide, an appropriate polyadenylation site.

The pCMV plasmids are a series of mammalian expression vectors of particular utility in the present invention. The vectors are designed for use in essentially all cultured cells and work extremely well in SV40-transformed simian COS cell lines. The pCMV1, 2, 3, and 5 vectors differ from each other in certain unique restriction sites in the polylinker region of each plasmid. The pCMV4 vector differs from these 4 plasmids in containing a translation enhancer in the sequence prior to the polylinker. While they are not directly derived from the pCMV1–5 series of vectors, the functionally similar pCMV6b and c vectors are available from the Chiron Corp. of Emeryville, Calif. and are identical except for the orientation of the polylinker region which is reversed in one relative to the other.

The universal components of the pCMV plasmids are as follows. The vector backbone is pTZ18R (Pharmacia), and contains a bacteriophage f1 origin of replication for production of single stranded DNA and an ampicillin-resistance gene. The CMV region consists of nucleotides −760 to +3 of the powerful promoter-regulatory region of the human cytomegalovirus (Towne stain) major immediate early gene (Thomsen et al., 1984; Boshart et al., 1985). The human growth hormone fragment (hGH) contains transcription termination and poly-adenylation signals representing sequences 1533 to 2157 of this gene (Seeburg, 1982). There is an Alu middle repetitive DNA sequence in this fragment. Finally, the SV40 origin of replication and early region promoter-enhancer derived from the pcD-X plasmid (HindII to PstI fragment) described in (Okayama et al., 1983). The promoter in this fragment is oriented such that transcription proceeds away from the CMV/hGH expression cassette.

The pCMV plasmids are distinguishable from each other by differences in the polylinker region and by the presence or absence of the translation enhancer. The starting pCMV1 plasmid has been progressively modified to render an increasing number of unique restriction sites in the polylinker region. To create pCMV2, one of two EcoRI sites in pCMV1 were destroyed. To create pCMV3, pCMV1 was modified by deleting a short segment from the SV40 region (StuI to EcoRI), and in so doing made unique the PstI, SalI, and BamHI sites in the polylinker. To create pCMV4, a synthetic fragment of DNA corresponding to the 5'-untranslated region of a mRNA transcribed from the CMV promoter was added C. The sequence acts as a translational enhancer by decreasing the requirements for initiation factors in polypeptide synthesis (Jobling et al., 1987); Browning et al., 1988). To create pCMV5, a segment of DNA (HpaI to EcoRI) was deleted from the SV40 origin region of pCMV1 to render unique all sites in the starting polylinker.

The pCMV vectors have been successfully expressed in simian COS cells, mouse L cells, CHO cells, and HeLa cells. In several side by side comparisons they have yielded 5- to 10-fold higher expression levels in COS cells than SV40-based vectors. The pCMV vectors have been used to express the LDL receptor, nuclear factor 1, GS alpha polypeptide, polypeptide phosphatase, synaptophysin, synapsin, insulin receptor, influenza hemmagglutinin, androgen receptor, sterol 26-hydroxylase, steroid 17- and 21-hydroxylase, cytochrome P-450 oxidoreductase, beta-adrenergic receptor, folate receptor, cholesterol side chain cleavage enzyme, and a host of other cDNAs. It should be noted that the SV40 promoter in these plasmids can be used to express other genes such as dominant selectable markers. Finally, there is an ATG sequence in the polylinker between the HindIII and PstI sites in pCMU that can cause spurious translation initiation. This codon should be avoided if possible in expression plasmids. A paper describing the construction and use of the parenteral pCMV1 and pCMV4 vectors has been published (Anderson et al., 1989b).

IV. Transfected Cells

In yet another embodiment, the present invention provides recombinant host cells transformed or transfected with polynucleotide that encode opioid receptor polypeptides, as well as transgenic cells derived from those transformed or transfected cells. Preferably, the recombinant host cells of the present invention are transfected with polynucleotide of SEQ ID NO:1, SEQ ID NO:3 or SEQ ID NO: 11. Means of transforming or transfecting cells with exogenous polynucleotide such as DNA molecules are well known in the art and include techniques such as calcium-phosphate- or DEAE-dextran-mediated transfection, protoplast fusion, electroporation, liposome mediated transfection, direct microinjection and adenovirus infection (Sambrook, Fritsch and Maniatis, 1989).

The most widely used method is transfection mediated by either calcium phosphate or DEAE-dextran. Although the mechanism remains obscure, it is believed that the transfected DNA enters the cytoplasm of the cell by endocytosis and is transported to the nucleus. Depending on the cell type, up to 90% of a population of cultured cells can be transfected at any one time. Because of its high efficiency, transfection mediated by calcium phosphate or DEAE-dextran is the method of choice for experiments that require transient expression of the foreign DNA in large numbers of cells. Calcium phosphate-mediated transfection is also used to establish cell lines that integrate copies of the foreign DNA, which are usually arranged in head-to-tail tandem arrays into the host cell genome.

In the protoplast fusion method, protoplasts derived from bacteria carrying high numbers of copies of a plasmid of interest are mixed directly with cultured mammalian cells. After fusion of the cell membranes (usually with polyethylene glycol), the contents of the bacteria are delivered into the cytoplasm of the mammalian cells and the plasmid DNA is transported to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA tandemly integrated into the host chromosome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Liposome transfection involves encapsulation of DNA and RNA within liposomes, followed by fusion of the liposomes with the cell membrane. The mechanism of how DNA is delivered into the cell is unclear but transfection efficiencies can be as high as 90%.

Direct microinjection of a DNA molecule into nuclei has the advantage of not exposing DNA to cellular compartments such as low-pH endosomes. Microinjection is therefore used primarily as a method to establish lines of cells that carry integrated copies of the DNA of interest.

The use of adenovirus as a vector for cell transfection is well known in the art. Adenovirus vector-mediated cell transfection has been reported for various cells (Stratford-Perricaudet, et al. 1992).

A transfected cell can be prokaryotic or eukaryotic. Preferably, the host cells of the invention are eukaryotic host cells. More preferably, the recombinant host cells of the invention are COS-1 cells. Where it is of interest to produce a human opioid receptor polypeptides, cultured mammalian or human cells are of particular interest.

In another aspect, the recombinant host cells of the present invention are prokaryotic host cells. Preferably, the recombinant host cells of the invention are bacterial cells of the DH5α strain of *Escherichia coli*. In general, prokaryotes are preferred for the initial cloning of DNA sequences and constructing the vectors useful in the invention. For example, *E. coli* K12 strains can be particularly useful. Other microbial strains which can be used include *E. coli* B, and *E. coli* $\chi^{1776}$ (ATCC No. 31537). These examples are, of course, intended to be illustrative rather than limiting.

Prokaryotes can also be used for expression. The aforementioned strains, as well as *E. coli* W3110 (F$^-$,λ$^-$, prototrophic, ATCC No. 273325), bacilli such as *Bacillus subtilis,* or other enterobacteriaceae such as *Salmonella typhimurium* or *Serratia marcesans,* and various Pseudomonas species can be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* can be transformed using pBR322, a plasmid derived from an *E. coli* species (Bolivar, et al. 1977). pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own polypeptides.

Those promoters most commonly used in recombinant DNA construction include the β-lactamase (penicillinase) and lactose promoter systems (Chang, et al. 1978; Itakura., et al. 1977, Goeddel, et al. 1979; Goeddel, et al. 1980) and a tryptophan (TRP) promoter system (EPO Appl. Publ. No. 0036776; Siebwenlist et al., 1980). While these are the most commonly used, other microbial promoters have been discovered and utilized, and details concerning their nucleotide sequences have been published, enabling a skilled worker to introduce functional promoters into plasmid vectors (Siebwenlist, et al. 1980).

In addition to prokaryotes, eukaryotic microbes such as yeast can also be used. *Saccharomyces cerevisiase* or common baker's yeast is the most commonly used among eukaryotic microorganisms, although a number of other strains are commonly available. For expression in Saccharomyces, the plasmid YRp7, for example, is commonly used (Stinchcomb, et al. 1979; Kingsman, et al. 1979; Tschemper, et al. 1980). This plasmid already contains the trpl gene which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoter sequences in yeast vectors include the promoters for 3-phosphoglycerate kinase (Hitzeman., et al. 1980) or other glycolytic enzymes (Hess, et al. 1968; Holland, et al. 1978) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also introduced into the expression vector downstream from the sequences to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin or replication and termination sequences is suitable.

In addition to microorganisms, cultures of cells derived from multicellular organisms can also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (Kruse and Peterson, 1973). Examples of such useful host cell lines are AtT-20, VERO and HeLa cells, Chinese hamster ovary (CHO) cell lines, and W138, BHK, COSM6, COS-7, 293 and MDCK cell lines. Expression vectors for such cells ordinarily include (if necessary) an origin of replication, a promoter located upstream of the gene to be expressed, along with any necessary ribosome binding sites, RNA splice sites, polyadenylation site, and transcriptional terminator sequences.

For use in mammalian cells, the control functions on the expression vectors are often derived from viral material. For example, commonly used promoters are derived from polyoma, Adenovirus 2, Cytomegalovirus and most frequently Simian Virus 40 (SV40). The early and late promoters of SV40 virus are particularly useful because both are obtained easily from the virus as a fragment which also contains the SV40 viral origin of replication (Fiers, et al. 1978). Smaller or larger SV40 fragments can also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication can be provided with by construction of the vector to include an exogenous origin, such as can be derived from SV40 or other viral (e.g., Polyoma, Adeno, VSV, BPV, CMV) source, or can be provided by the host cell chromosomal replication mechanism. If the vector is integrated into the host cell chromosome, the latter is often sufficient.

V. Preparing Recombinant Opioid Receptor Polypeptides

In yet another embodiment, the present invention contemplates a process of preparing opioid receptor polypeptides comprising transfecting cells with polynucleotide that encode opioid receptor polypeptides to produce transformed host cells; and maintaining the transformed host cells under biological conditions sufficient for expression of the polypeptide. Preferably, the transformed host cells are eukaryotic cells. More preferably still, the eukaryotic cells are COS-1 cells. Alternatively, the host cells are prokaryotic cells. More preferably, the prokaryotic cells are bacterial cells of the DH5α strain of *Escherichia coli*. Even more preferably, the polynucleotide transfected into the transformed cells comprise the nucleotide base sequence of SEQ ID NO:1, SEQ ID NO:3 or SEQ ID NO: 11. Most preferably transfection is accomplished using a hereinbefore disclosed expression vector.

A host cell used in the process is capable of expressing a functional, recombinant opioid receptor polypeptide. A preferred host cell is a Chinese hamster ovary cell. However, a variety of cells are amenable to a process of the invention, for instance, yeasts cells, human cell lines, and other eukaryotic cell lines known well to those of skill in the art.

Following transfection, the cell is maintained under culture conditions for a period of time sufficient for expression of an opioid receptor polypeptide. Culture conditions are well known in the art and include ionic composition and concentration, temperature, pH and the like. Typically, transfected cells are maintained under culture conditions in a culture medium. Suitable medium for various cell types are well known in the art. In a preferred embodiment, temperature is from about 20° C. to about 50° C., more preferably from about 30° C. to about 40° C. and, even more preferably about 37° C.

pH is preferably from about a value of 6.0 to a value of about 8.0, more preferably from about a value of about 6.8 to a value of about 7.8 and, most preferably about 7.4. Osmolality is preferably from about 200 milliosmols per liter (mosm/L) to about 400 mosm/l and, more preferably from about 290 mosm/L to about 310 mosm/L. Other biological conditions needed for transfection and expression of an encoded protein are well known in the art.

Transfected cells are maintained for a period of time sufficient for expression of an opioid receptor polypeptide. A suitable time depends inter alia upon the cell type used and is readily determinable by a skilled artisan. Typically, maintenance time is from about 2 to about 14 days.

Recombinant opioid receptor polypeptide is recovered or collected either from the transfected cells or the medium in which those cells are cultured. Recovery comprises isolating and purifying the opioid receptor polypeptide. Isolation and purification techniques for polypeptides are well known in the art and include such procedures as precipitation, filtration, chromatography, electrophoresis and the like.

VI. Antibodies

In still another embodiment, the present invention provides antibodies immunoreactive with opioid receptor polypeptides. Preferably, the antibodies of the invention are monoclonal antibodies. More preferably, the opioid receptor polypeptides comprise the amino acid residue sequence of SEQ ID NO:2, SEQ ID NO:4 or SEQ ID NO: 12. Means for preparing and characterizing antibodies are well known in the art (See, e.g., *Antibodies "A Laboratory Manual,* E. Howell and D. Lane, Cold Spring Harbor Laboratory, 1988).

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide may vary in its immunogenicity. It is often necessary therefore to couple the immunogen (e.g., a polypeptide or polynucleotide) of the present invention with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier protein are well known in the art and include glutaraldehyde, m-maleimidobencoyl-N-hydroxysuccinimide ester, carbodiimide and bis-biazotized benzidine.

As is also well known in the art, immunogencity to a particular immunogen can be enhanced by the use of nonspecific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies inter alia, upon the nature of the immunogen as well as the animal used for immunization. A variety of routes can be used to administer the immunogen (subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

In another aspect, the present invention contemplates a process of producing an antibody immunoreactive with an opioid receptor polypeptide comprising the steps of (a) transfecting recombinant host cells with polynucleotide that encode opioid receptor polypeptides; (b) culturing the host cells under conditions sufficient for expression of the polypeptides; (c) recovering the polypeptides; and (d) preparing the antibodies to the polypeptides. Preferably, the host cell is transfected with the polynucleotide of SEQ ID NO:1, SEQ ID NO:3 or SEQ ID NO: 11. Even more preferably, the present invention provides antibodies prepared according to the process described above.

A monoclonal antibody of the present invention can be readily prepared through use of well-known techniques such as those exemplified in U.S. Pat. No. 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptide. The selected clones can then be propagated indefinitely to provide the monoclonal antibody.

By way of specific example, to produce an antibody of the present invention, mice are injected intraperitoneally with between about 1–200 $\mu$g of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radio-labeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immuno-specific reaction with the bound antibody. The polypeptide or polynucleotide is then easily removed from the substrate and purified.

VII. Pharmaceutical Compositions

In a preferred embodiment, the present invention provides pharmaceutical compositions comprising opioid receptor polypeptides and physiologically acceptable carriers. More preferably, the pharmaceutical compositions comprise opioid receptor polypeptides comprising the amino acid residue sequence of SEQ ID NO:1, SEQ ID NO:4 or SEQ ID NO: 12. Even more preferably, the pharmaceutical compositions of the invention comprise polynucleotide that encode opioid receptor polypeptides, and physiologically acceptable carriers. Still more preferably, the pharmaceutical compositions of the present invention comprise opioid receptor polypeptides comprising the amino acid residue sequence of SEQ ID NO:2, SEQ ID NO:4 or SEQ ID NO: 12. Alternatively, the pharmaceutical compositions comprise polynucleotide comprising the nucleotide sequence of SEQ ID NO:1, SEQ ID NO:3 or SEQ ID NO: 11.

A composition of the present invention is typically administered parenterally in dosage unit formulations containing standard, well-known nontoxic physiologically acceptable carriers, adjuvants, and vehicles as desired. The term parenteral as used herein includes intravenous, intramuscular, intraarterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A carrier can also be a liposome. Means for using liposomes as delivery vehicles are well known in the art [See, e.g. Gabizon et al., 1990; Ferruti et al., 1986; and Ranade, V. V., 1989].

A transfected cell can also serve as a carrier. By way of example, a liver cell can be removed from an organism, transfected with a polynucleotide of the present invention using methods set forth above and then the transfected cell returned to the organism (e.g. injected intravascularly).

VIII. Detecting Polynucleotide and the Polypeptides Encoded

Alternatively, the present invention provides a process of detecting opioid receptor polypeptides, wherein the process comprises immunoreacting the polypeptides with antibodies prepared according to the process described above to form antibody-polypeptide conjugates, and detecting the conjugates.

In yet another embodiment, the present invention contemplates a process of detecting messenger RNA transcripts that encode opioid receptor polypeptides, wherein the process comprises (a) hybridizing the messenger RNA transcripts with polynucleotide sequences that encode the opioid receptor polypeptides to form duplexes; and (b) detecting the duplex. Alternatively, the present invention provides a process of detecting DNA molecules that encode opioid receptor polypeptides, wherein the process comprises (a) hybridizing DNA molecules with polynucleotide that encode opioid receptor polypeptides to form duplexes; and (b) detecting the duplexes.

IX. Screening Assays

In yet another aspect, the present invention contemplates a process of screening substances for their ability to interact with opioid receptor polypeptides comprising the steps of providing opioid receptor polypeptides, and testing the ability of selected substances to interact with the opioid receptor polypeptides.

Utilizing the methods and compositions of the present invention, screening assays for the testing of candidate substances such as agonists and antagonists of opioid receptors can be derived. A candidate substance is a substance which potentially can interact with or modulate, by binding or other intramolecular interaction, an opioid receptor polypeptide. In some instances, such a candidate substance will be an agonist of the receptor and in other instances can exhibit antagonistic attributes when interacting with the receptor polypeptide. In other instances, such substances can have mixed agonistic and antagonistic properties or can modulate the opioid receptor in other ways.

Recombinant receptor expression systems of the present invention possess definite advantages over tissue-based systems. The methods of the present invention make it possible to produce large quantities of opioid receptors for use in screening assays. More important, however, is the relative purity of the receptor polypeptides provided by the present invention. A relatively pure polypeptide preparation for assaying a protein-protein interaction makes it possible to use elutive methods without invoking competing, and unwanted, side-reactions.

Cloned expression systems such as those of the present invention are also useful where there is difficulty in obtaining tissue that satisfactorily expresses a particular receptor. Cost is another very real advantage, at least with regard to the microbial expression systems of the present invention. For antagonists in a primary screen, microorganism expression systems of the present invention are inexpensive in comparison to prior art tissue-screening methods.

Traditionally, screening assays employed the use of crude receptor preparations. Typically, animal tissue slices thought to be rich in the receptor of interest was the source of the receptor. Alternatively, investigators homogenized the tissue and used the crude homogenate as a receptor source. A major difficulty with this approach is that there are no tissue types where only one receptor type is expressed. The data obtained therefore could not be definitively correlated with a particular receptor. With the recent cloning of receptor sub-types and sub-sub-types, this difficulty is highlighted. A second fundamental difficulty with the traditional approach is the unavailability of human tissue for screening potential drugs. The traditional approach almost invariably utilized animal receptors. With the cloning of human receptors, there is a need for screening assays which utilize human receptors.

With the availability of cloned receptors, recombinant receptor screening systems have several advantages over tissue based systems. A major advantage is that the investigator can now control the type of receptor that is utilized in a screening assay. Specific receptor sub-types and sub-sub-types can be preferentially expressed and its interaction with a ligand can be identified. Other advantages include the availability of large amounts of receptor, the availability of rare receptors previously unavailable in tissue samples, and the lack of expenses associated with the maintenance of live animals.

Screening assays of the present invention generally involve determining the ability of a candidate substance to bind to the receptor and to affect the activity of the receptor, such as the screening of candidate substances to identify those that inhibit or otherwise modify the receptor's function. Typically, this method includes preparing recombinant receptor polypeptide, followed by testing the recombinant polypeptide or cells expressing the polypeptide with a candidate substance to determine the ability of the substance to affect its physiological function. In preferred embodiments, the invention relates to the screening of candidate substances to identify those that affect the enzymatic activity of the human receptor, and thus can be suitable for use in humans.

As is well known in the art, a screening assay provides a receptor under conditions suitable for the binding of an agent to the receptor. These conditions include but are not limited to pH, temperature, tonicity, the presence of relevant co-factors, and relevant modifications to the polypeptide such as glycosylation or prenylation. It is contemplated that the receptor can be expressed and utilized in a prokaryotic or eukaryotic cell. The host cell expressing the receptor can be used whole or the receptor can be isolated from the host cell. The receptor can be membrane bound in the membrane of the host cell or it can be free in the cytosol of the host cell. The host cell can also be fractionated into sub-cellular fractions where the receptor can be found. For example, cells expressing the receptor can be fractionated into the nuclei, the endoplasmic reticulum, vesicles, or the membrane surfaces of the cell.

pH is preferably from about a value of 6.0 to a value of about 8.0, more preferably from about a value of about 6.8 to a value of about 7.8 and, most preferably about 7.4. In a preferred embodiment, temperature is from about 20° C. to about 50° C., more preferably from about 30° C. to about 40° C. and, even more preferably about 37° C. Osmolality is preferably from about 5 milliosmols per liter (mosm/L) to about 400 mosm/l and, more preferably from about 200 milliosmols per liter to about 400 mosm/l and, even more preferably from about 290 mosm/L to about 310 mosm/L. The presence of co-factors can be required for the proper functioning of the receptor. Typical co-factors include sodium, potassium, calcium, magnesium, and chloride. In addition, small, non-peptide molecules, known as prosthetic groups can be required. Other biological conditions needed for receptor function are well known in the art.

It is well known in the art that proteins can be reconstituted in artificial membranes, vesicles or liposomes. (Danboldt, et al. 1990). The present invention contemplates that the receptor can be incorporated into artificial membranes, vesicles or liposomes. The reconstituted receptor can be utilized in screening assays.

It is further contemplated that the receptor of the present invention can be coupled to a solid support. The solid support can be agarose beads, polyacrylamide beads, polyacrylic beads or other solid matrices capable of being coupled to proteins. Well known coupling agents include cyanogen bromide, carbonyldiimidazole, tosyl chloride, and gluteraldehyde.

It is further contemplated that secondary polypeptides which can function in conjunction with the receptor of the present invention can be provided. For example, the receptor of the present invention exerts its physiological effects in conjunction with a G-protein and an effector polypeptide.

In a typical screening assay for identifying candidate substances, one employs the same recombinant expression host as the starting source for obtaining the receptor polypeptide, generally prepared in the form of a crude homogenate. Recombinant cells expressing the receptor are washed and homogenized to prepare a crude polypeptide homogenate in a desirable buffer such as disclosed herein. In a typical assay, an amount of polypeptide from the cell homogenate, is placed into a small volume of an appropriate assay buffer at an appropriate pH. Candidate substances, such as agonists and antagonists, are added to the admixture in convenient concentrations and the interaction between the candidate substance and the receptor polypeptide is monitored.

Where one uses an appropriate known substrate for the receptor, one can, in the foregoing manner, obtain a baseline activity for the recombinantly produced receptor. Then, to test for inhibitors or modifiers of the receptor function, one can incorporate into the admixture a candidate substance whose effect on the receptor is unknown. By comparing reactions which are carried out in the presence or absence of the candidate substance, one can then obtain information regarding the effect of the candidate substance on the normal function of the receptor.

Accordingly, it is proposed that this aspect of the present invention provides those of skill in the art with methodology that allows for the identification of candidate substances having the ability to modify the action of opioid receptor polypeptides in one or more manners.

In one embodiment, such an assay is designed to be capable of discriminating those candidate substances with the desirable properties of opioids but which lack the undesirable properties of opioids. In another embodiment, screening assays for testing candidate substances such as agonists and antagonists of opioid receptors are used to identify such candidate substances having selective ability to interact with one or more of the opioid receptor polypeptides but which polypeptides are without a substantially overlapping activity with another of the opioid receptor polypeptides identified herein.

Additionally, screening assays for the testing of candidate substances are designed to allow the investigation of structure activity relationships of opioid with the receptors, e.g., study of binding of naturally occurring hormones or other substances capable of interacting or otherwise modulating with the receptor versus studies of the activity caused by the binding of such molecules to the receptor. In certain embodiments, the polypeptides of the invention are crystallized in order to carry out x-ray crystallographic studies as a means of evaluating interactions with candidate substances or other molecules with the opioid receptor polypeptide. For instance, the purified recombinant polypeptides of the invention, when crystallized in a suitable form, are amenable to detection of intra-molecular interactions by x-ray crystallography.

An important aspect of the invention is the use of recombinantly produced opioid receptor polypeptide in screening assays for the identification of substances which can inhibit or otherwise modify or alter the function of the receptor. The use of recombinantly produced receptor is of particular benefit because the naturally occurring receptor is present in only small quantities and has proven difficult to purify. Moreover, this provides a ready source of receptor, which has heretofore been unavailable.

As described above, receptors in the presence of agonists exert its physiological effects through a secondary molecule. A screening assay of the invention, in preferred embodiments, conveniently employs an opioid receptor polypeptide directly from the recombinant host in which it is produced. This is achieved most preferably by simply expressing the selected polypeptide within the recombinant host, typically a eukaryotic host, followed by preparing a crude homogenate which includes the enzyme. A portion of the crude homogenate is then admixed with an appropriate effector of the receptor along with the candidate substance to be tested. By comparing the binding of the selected effector to the receptor in the presence or absence of the candidate substance, one can obtain information regarding the physiological properties of the candidate substance.

The receptor can be expressed in a prokaryotic or a eukaryotic cell. Receptors have been expressed in *E. coli*

(Bertin, et al. 1992), in yeast (King, et al. (1990) and in mammalian cells (Bouvier, et. al. 1988).

A cell expressing a receptor can be used whole to screen agents. For example, cells expressing the receptor of the present invention can be exposed to radiolabelled agent and the amount of binding of the radiolabelled agent to the cell can be determined.

The cell expressing the receptor can be fractionated into sub-cellular components which contain the receptor of the present invention. Methods for purifying sub-cellular fractions are well known in the art. Sub-cellular fractions include but are not limited to the cytoplasm, cellular membrane, other membranous fractions such as the endoplasmic reticulum, golgi bodies, vesicles and the nucleus. Receptors isolated as sub-cellular fractions can be associated with cellular membranes. For example, if cellular membrane vesicles are isolated from the cell expressing the receptor, the receptor molecule can be membrane bound. It is further contemplated that the receptor of the present invention can be purified from a cell that expresses the receptor. Methods of purification are well known in the art. The purified receptor can be used in screening assays.

In that most such screening assays in accordance with the invention are designed to identify agents useful in mimicking the desirable aspects of opioids while eliminating the undesirable aspects of the hormone, preferred assays employ opioids as the normal agonist.

There are believed to be a wide variety of embodiments which can be employed to determine the effect of the candidate substance on the receptor polypeptides of the invention, and the invention is not intended to be limited to any one such method. However, it is generally desirable to employ a system wherein one can measure the ability of the receptor polypeptide to bind to and or be modified by the effector employed in the presence of a particular substance.

The detection of an interaction between an agent and a receptor can be accomplished through techniques well known in the art. These techniques include but are not limited to centrifugation, chromatography, electrophoresis and spectroscopy. The use of isotopically labelled reagents in conjunction with these techniques or alone is also contemplated. Commonly used radioactive isotopes include $^3$H, $^{14}$C, $^{22}$Na, $^{32}$P, $^{35}$S, $^{45}$Ca, $^{60}$Co, $^{125}$I, and $^{131}$I. Commonly used stable isotopes include $^2$H, $^{13}$C, $^{15}$N, $^{18}$O.

For example, if an agent can bind to the receptor of the present invention, the binding can be detected by using radiolabelled agent or radiolabelled receptor. Briefly, if radiolabelled agent or radiolabelled receptor is utilized, the agent-receptor complex can be detected by liquid scintillation or by exposure to X-Ray film.

When an agent modifies the receptor, the modified receptor can be detected by differences in mobility between the modified receptor and the unmodified receptor through the use of chromatography, electrophoresis or centrifugation. When the technique utilized is centrifugation, the differences in mobility is known as the sedimentation coefficient. The modification can also be detected by differences between the spectroscopic properties of the modified and unmodified receptor. As a specific example, if an agent covalently modifies a receptor, the difference in retention times between modified and unmodified receptor on a high pressure liquid chromatography (HPLC) column can easily be detected.

As a specific example, if an agent covalently modifies a receptor, the spectroscopic differences between modified and unmodified receptor in the nuclear magnetic resonance (NMR) spectra can be detected. Alternatively, one can focus on the agent and detect the differences in the spectroscopic properties or the difference in mobility between the free agent and the agent after modification of the receptor.

When a secondary polypeptide is provided, the agent-receptor-secondary polypeptide complex or the receptor-secondary polypeptide complex can be detected. Differences in mobility or differences in spectroscopic properties as described above can be detected.

It is further contemplated that when a secondary polypeptide is provided the enzymatic activity of the effector polypeptide can be detected. For example, many receptors exert physiological effects through the stimulation or inhibition of adenylyl cyclase. The enzymatic activity of adenylyl cyclase in the presence of an agent can be detected.

The interaction of an agent and a receptor can be detected by providing a reporter gene. Well known reporter genes include β-galactosidase (β-Gal), chloramphenicol transferase (CAT) and luciferase. The reporter gene is expressed by the host and the enzymatic reaction of the reporter gene product can be detected.

In preferred assays, an admixture containing the polypeptide, effector and candidate substance is allowed to incubate for a selected amount of time, and the resultant incubated mixture subjected to a separation means to separate the unbound effector remaining in the admixture from any effector/receptor complex so produced. Then, one simply measures the amount of each (e.g., versus a control to which no candidate substance has been added). This measurement can be made at various time points where velocity data is desired. From this, one can determine the ability of the candidate substance to alter or modify the function of the receptor.

Numerous techniques are known for separating the effector from effector/receptor complex, and all such methods are intended to fall within the scope of the invention. Use of thin layer chromatographic methods (TLC), HPLC, spectrophotometric, gas chromatographic/mass spectrophotometric or NMR analyses. It is contemplated that any such technique can be employed so long as it is capable of differentiating between the effector and complex, and can be used to determine enzymatic function such as by identifying or quantifying the substrate and product.

The effector/receptor complex itself can also be the subject of techniques such as x-ray crystallography. Where a candidate substance replaces the opioid molecule as the drug's mode of action, studies designed to monitor the replacement and its effect on the receptor will be of particular benefit.

A. Screening Assays for Opioid Receptor Polypeptides.

The present invention provides a process of screening a biological sample for the presence of an opioid receptor polypeptide. A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide.

In accordance with a screening assay process, a biological sample is exposed to an antibody immunoreactive with the opioid receptor polypeptide whose presence is being assayed. Typically, exposure is accomplished by forming an admixture in a liquid medium that contains both the antibody and the candidate opioid receptor polypeptide. Either the antibody or the sample with the opioid receptor polypeptide can be affixed to a solid support (e.g., a column or a microtiter plate).

The biological sample is exposed to the antibody under biological reaction conditions and for a period of time sufficient for antibody-polypeptide conjugate formation. Biological reaction conditions include ionic composition and concentration, temperature, pH and the like.

Ionic composition and concentration can range from that of distilled water to a 2 molal solution of NaCl. Preferably, osmolality is from about 100 mosmols/l to about 400 mosmols/l and, more preferably from about 200 mosmols/l to about 300 mosmols/l. Temperature preferably is from about 4° C. to about 100° C., more preferably from about 15° C. to about 50° C. and, even more preferably from about 25° C. to about 40° C. pH is preferably from about a value of 4.0 to a value of about 9.0, more preferably from about a value of 6.5 to a value of about 8.5 and, even more preferably from about a value of 7.0 to a value of about 7.5. The only limit on biological reaction conditions is that the conditions selected allow for antibody-polypeptide conjugate formation and that the conditions do not adversely affect either the antibody or the opioid receptor polypeptide.

Exposure time will vary inter alia with the biological conditions used, the concentration of antibody and polypeptide and the nature of the sample (e.g., fluid or tissue sample). Means for determining exposure time are well known to one of ordinary skill in the art. Typically, where the sample is fluid and the concentration of polypeptide in that sample is about $10^{-10}$ M, exposure time is from about 10 minutes to about 200 minutes.

The presence of opioid receptor polypeptide in the sample is detected by detecting the formation and presence of antibody-opioid receptor polypeptide conjugates. Means for detecting such antibody-antigen (e.g., receptor polypeptide) conjugates or complexes are well known in the art and include such procedures as centrifugation, affinity chromatography and the like, binding of a secondary antibody to the antibody-candidate receptor complex.

In one embodiment, detection is accomplished by detecting an indicator affixed to the antibody. Exemplary and well known such indicators include radioactive labels (e.g., $^{32}$P, $^{125}$I, $^{14}$C), a second antibody or an enzyme such as horse radish peroxidase. Means for affixing indicators to antibodies are well known in the art. Commercial kits are available.

B. Screening Assay for Anti-opioid Receptor Antibody.

In another aspect, the present invention provides a process of screening a biological sample for the presence of antibodies immunoreactive with an opioid receptor polypeptide (i.e., an anti-opioid receptor antibody). In accordance with such a process, a biological sample is exposed to an opioid receptor polypeptide under biological conditions and for a period of time sufficient for antibody-polypeptide conjugate formation and the formed conjugates are detected.

C. Screening Assay for Polynucleotide that Encodes an Opioid Receptor Polypeptide.

A DNA molecule and, particularly a probe molecule, can be used for hybridizing as oligonucleotide probes to a DNA source suspected of possessing an opioid receptor polypeptide encoding polynucleotide or gene. The probing is usually accomplished by hybridizing the oligonucleotide to a DNA source suspected of possessing such a receptor gene. In some cases, the probes constitute only a single probe, and in others, the probes constitute a collection of probes based on a certain amino acid sequence or sequences of the opioid receptor polypeptide and account in their diversity for the redundancy inherent in the genetic code.

A suitable source of DNA for probing in this manner is capable of expressing opioid receptor polypeptides and can be a genomic library of a cell line of interest. Alternatively, a source of DNA can include total DNA from the cell line of interest. Once the hybridization process of the invention has identified a candidate DNA segment, one confirms that a positive clone has been obtained by further hybridization, restriction enzyme mapping, sequencing and/or expression and testing.

Alternatively, such DNA molecules can be used in a number of techniques including their use as: (1) diagnostic tools to detect normal and abnormal DNA sequences in DNA derived from patient's cells; (2) means for detecting and isolating other members of the opioid receptor family and related polypeptides from a DNA library potentially containing such sequences; (3) primers for hybridizing to related sequences for the purpose of amplifying those sequences; (4) primers for altering the native opioid receptor DNA sequences; as well as other techniques which rely on the similarity of the DNA sequences to those of the opioid receptor DNA segments herein disclosed.

As set forth above, in certain aspects, DNA sequence information provided by the invention allows for the preparation of relatively short DNA (or RNA) sequences (e.g., probes) that specifically hybridize to encoding sequences of the selected opioid receptor gene. In these aspects, nucleic acid probes of an appropriate length are prepared based on a consideration of the selected opioid receptor sequence (e.g., a sequence such as that shown in SEQ ID NO:1, SEQ ID NO:3 or SEQ ID NO: 11). The ability of such nucleic acid probes to specifically hybridize to opioid receptor encoding sequences lend them particular utility in a variety of embodiments. Most importantly, the probes can be used in a variety of assays for detecting the presence of complementary sequences in a given sample. However, uses are envisioned, including the use of the sequence information for the preparation of mutant species primers, or primers for use in preparing other genetic constructions.

To provide certain of the advantages in accordance with the invention, a preferred nucleic acid sequence employed for hybridization studies or assays includes probe sequences that are complementary to at least a 14 to 40 or so long nucleotide stretch of the opioid receptor encoding sequence, such as that shown in SEQ ID NO:1, SEQ ID NO:3 or SEQ ID NO: 11. A size of at least 14 nucleotides in length helps to ensure that the fragment is of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments can be readily prepared by, for example, directly synthesizing the fragment by chemical means, by application of nucleic acid reproduction technology, such as the PCR™ technology of U.S. Pat. No. 4,683,202, herein incorporated by reference, or by introducing selected sequences into recombinant vectors for recombinant production.

Accordingly, a nucleotide sequence of the present invention can be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 0.02 M–0.15 M NaCl at temperatures of 50° C. to 70° C. Such conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate opioid receptor coding sequences from related species, functional equivalents, or the like, less stringent hybridization conditions are typically needed to allow formation of the heteroduplex. Under such circumstances, one employs conditions such as 0.15 M–0.9 M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a nucleic acid sequence of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend inter alia on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantified, by means of the label.

D. Screening for Agonists and Antagonists

Delta receptors are one of the three major subtypes of opioid receptors. The endogenous peptides that interact with this receptor are methionine- and leucine-enkephalin. These receptors are coupled to multiple cellular effector systems, including adenylyl cyclase, $Ca^{++}$ and $K^+$ channels via pertussin-toxin sensitive G proteins. Delta opioid receptors mediate analgesic effects of opioids. While delta opioid receptor agonists can induce analgesia, they have limited abuse potential. Therefore, highly selective delta opioid receptor agonists can be clinically useful in the treatment of chronic pain without the harmful side-effects of addiction.

Development of highly selective, clinically useful delta opioid receptor agonists would be facilitated by understanding the specific sites within the delta receptor necessary for agonist binding. The cloning of the mouse delta opioid receptor cDNA has opened up the possibility to investigate the structural domains of this receptor subtype that are responsible for its functioning. As indicated below, a single amino acid in the second transmembrane spanning region of the delta receptor is critical for the binding of delta-selective opioid agonists.

To investigate structural components of the mouse delta opioid receptor involved in ligand binding, an aspartate at residue 95 was converted to an asparagine by site-directed mutagenesis. This aspartate is conserved among G protein-linked receptors and has been proposed to mediate Na+ regulation of agonist binding. To test the ligand binding characteristics of the delta receptor, the mutant and wild-type receptors were expressed in COS-7 cells. Both receptors could be labeled with the delta-selective agonist [$^3$H]-DPDPE and the antagonist [$^3$H]-naltrindole. Na+ (90 mM) reduced [$^3$H]-DPDPE binding to the wild-type delta receptor but not to the mutant receptor. Na+ did not affect [$^3$H]-naltrindole binding but reduced the potency of agonists to inhibit radiolabeled antagonist binding to the wild-type receptor but not to the mutant receptor, indicating that Na+ selectively reduces the affinity of the wild-type receptor for agonists.

The binding of [$^3$H]-DPDPE to the mutant receptor was reduced compared to the wild-type. The reduced binding could be due to uncoupling of the receptor from G proteins, low expression of the mutant receptor or an alteration in the ligand binding properties of the receptor. The mutant receptor remained coupled to G proteins since GTPγS could reduce [$^3$H]-DPDPE binding to the receptor. Furthermore, the mutant receptor could mediate agonist inhibition of cAMP formation, a response requiring G protein coupling. The mutant receptor was expressed at higher levels than the wild-type receptor. Therefore, the mutant receptor had a selective reduction in affinity for agonists.

This was further indicated by the diminished potencies of the delta selective agonists DPDPE, DSLET, deltorphin and met-enkephalin to inhibit [$^3$H]-naltrindole binding to the mutant receptor compared to the wild-type receptor. The affinity of the mutant receptor was over 100-fold less for these peptides. In contrast, the affinity of the mutant and wild-type receptors for the delta selective antagonists naltrindole, NTB and BNTX were similar, indicating that the mutant receptor had a specific reduction in affinity for agonists.

The potency of a non-selective opioid agonist such as bremazocine at binding to the mutant and wild-type delta receptors was similar. This compound is an agonist at all opioid receptor subtypes. The alkaloid buprenorphine is a compound being used to treat opioid addiction, that has been reported to be a partial mu opioid agonist and is a full agonist at the delta receptor since it inhibits forskolin stimulated cAMP formation in COS cells expressing either the wild-type or mutant delta receptor. This non-peptide agonist potently binds to both the mutant and wild-type delta opioid receptor with similar affinities. Since the mutant receptor exhibits similar affinity as the wild-type receptor for non-selective, non-peptide opioid agonists but had diminished affinity for the delta-selective peptide agonists, differences in ligand binding properties of the mutant and wild-type receptors were examined relative to the peptide nature of the agonists or their delta receptor-selective characteristics.

BW373U86 and SIOM are non-peptide, potent delta opioid receptor selective agonists. Both compounds stimulate the wild-type and mutant delta receptors to inhibit cAMP formation. BW373U86 and SIOM potently inhibit [$^3$H]-naltrindole binding to the wild-type delta receptor. In contrast, BW373U86 is over 100-fold, and SIOM is over 50-fold less potent at binding to the mutant receptor. These findings indicate that the mutant delta receptor has reduced affinity for delta opioid receptor-selective agonists of different structures.

The data show that the aspartate at residue 95 of the mouse delta opioid receptor is necessary for the high affinity binding of the delta receptor selective agonists. This residue is not necessary for antagonist binding nor for the binding of non-selective opioid agonists. The ability of the non-selective agonists to bind to and stimulate the mutant and wild-type delta receptors equally well suggests that the single residue mutation did not induce large conformational changes in the receptor that would non-selectively alter the ligand binding domain or inhibit the interaction of the receptor with G proteins, which is essential for the receptor to bind agonists with high affinity. Because the binding of non-selective agonists and the delta selective antagonists to the delta receptor was not affected by the point mutation, such agonists and antagonists may interact with similar regions of the ligand binding domain of this opioid receptor that are distinct from the site involved in delta opioid receptor selective agonist binding. The aspartate 95 may facilitate the binding of agonists selective for the delta receptor by providing a negative charge for stabilization of ligand interaction with the receptor that is not necessary for the binding of non-selective agonists or delta opioid antagonists. Similarly an aspartate in the beta-adrenergic receptor has been proposed to provide a charge for stabilization of the binding of beta-adrenergic selective agonists. Recent studies have also shown that a single amino acid in the tachykinin and cholecytokinin receptors are responsible for subtype selective antagonist binding, further indicating that a single residue can be critical for specific ligand-receptor interactions.

The data show that selective agonists and antagonists bind differently to the delta opioid receptor. This suggests that they may interact with distinct regions of this receptor. A domain of the second transmembrane spanning region of the delta opioid receptor containing the aspartate 95 is involved the selective binding of agonists.

E. Chimeric Opioid Receptor Polypeptides

Kappa and delta opioid receptors exhibit distinct pharmacological specificities. The high degree of amino acid sequence similarly between the kappa and delta opioid receptors in their transmembrane spanning regions suggests that extracellular domains are likely involved in selective ligand binding to each receptor. The amino-terminal extracellular regions of the two receptors are divergent in amino acid sequence.

Standard mutagenesis techniques well known in the art are used to create chimeric opioid receptor polypeptides comprising portions from different receptor subtypes. In a preferred embodiment, the amino-terminal region of a particular receptor subtype (e.g.,kappa, delta) is linked to a portion (non-amino-terminal) of a different receptor subtype. In this way, amino-terminals of particular receptor subtypes can be exchanged. A mutant polynucleotide (e.g., cDNA) that encodes such a chimeric receptor polypeptide is then transfected into a host cell where the chimeric receptor is expressed. A preferred host cell is a COS cell. The recombinant chimeric receptor receptor polypeptide is then tested for its ability to bind subtype-selective agonists and antagonists.

An SpeI restriction site in the first transmembrane spanning region was engineered into mouse kappa receptor and delta receptor cDNAs using oligonucleotide-directed mutagenesis. The site was engineered into identical locations in both cDNAs, thereby avoiding frameshifts and/or deletions or additions in sequence. There are no naturally occurring SpeI restriction sites in the coding regions of either the kappa or delta opioid receptor cDNAs. Fragments corresponding to the amino-termini of each receptor are isolated by cutting at this newly engineered SpeI site in both cDNAs. Those fragments are then ligated to purified cDNA corresponding to the carboxy-terminus of the opposite receptor to generate chimeric $kappa_{1-74}/delta_{65-372}$ and $delta_{1-64}/kappa_{75-380}$ receptors.

The mutant DNA fragments are subcloned into a suitable expression vector (e.g., the mammalian expression vector pCMV6$_o$) and either transiently transfected into or stably expressed in a suitable host cell such as COS-7 cells or CHO cells. The chimeric is then used in agonist, antagonist studies. By way of example, a $kappa_{1-74}/delta_{65-372}$ chimeric is tested for its ability to be labeled with the delta receptor selective agonist [$^3$H]-DPDPE and the antagonist [$^3$H]-naltrindole, which bind potently to the wild-type delta receptor and the kappa selective agonist [$^3$H]-U69,593 and the antagonist [$^3$H]-naloxone, which bind to the cloned kappa but not the cloned delta opioid receptor. If the delta opioid receptor radioligands do not bind to this chimeric receptor, but [$^3$H]-U69,593 and [$^3$H]-naloxone do bind with high potency, the ligand binding regions of both receptors is likely included in the amino-terminus.

Mouse kappa and delta opioid receptor cDNA were mutated using the Altered Site™ in vitro Mutagenesis System (Promega Corp. Madison Wis.). To engineer in the SpeI restriction site at residues 78–80 in the first transmembrane spanning regions of the kappa receptor cDNA, the mouse kappa receptor cDNA was subcloned into the phagemid pALTER™ and with the helper phage R408, single-stranded template was produced. A 24-mer oligonucleotide (GTGGGCAATTCACTAGTCATGTTT; SEQ ID NO:7) encoding the desired mutation (TCTGGT to ACTAGT) was annealed to the single-stranded template and elongated with T4 DNA polymerase. The heteroduplex DNA was then used to transform the repair-minus E. coli strain BMH 71-18 mut S.

Transformants were selected by growth in LB plates containing 125 µg/ml ampicillin. Double-stranded plasmid DNA was sequenced by the Sanger dideoxy chain termination method and digested with SpeI to confirm the presence of the mutation. For the delta receptor cDNA, a 24-mer oligonucleotide (CTGGGCAACGTACTAGTCATGTTT; SEQ ID NO:8) encoding the desired mutation (GOTCGT to ACTAGT) was used and similar procedures as described above for the kappa receptor cDNA were employed. Each mutated cDNA was excised from pALTER™ with EcoRI and SalI in the case of the delta receptor cDNA and SalI and BamHI for the kappa receptor cDNA and subcloned into the corresponding sites in the mammalian expression vector pCMV6c. The 6' regions of each cDNA corresponding to the N-terminal regions of each receptor (residues 1–75 in the kappa receptor and 1–65 in the delta receptor) were excised with EcoRI/SpeI (delta receptor) and SalI/SpeI (kappa receptor) and gel purified. The N-terminal fragment of the kappa receptor was ligated to the C-terminal fragment of the delta receptor. The inserts were excised from the vector and their size determined by agarose gel electrophoresis to establish whether appropriate ligation occurred. The chimeric kappa-delta receptor cDNA was then transiently transfected into COS-7 cells by a calcium-phosphate-mediated procedure.

The selective kappa agonist [$^3$H]-U69593 did not bind to the kappa$_{1-74}$/delta$_{65-372}$ chimera. The antagonist [$^3$H]-naloxone, which binds with high affinity to the wild-type kappa but not delta receptor, bound to the chimera. The [$^3$H]-naloxone binding was potently inhibited by the kappa selective antagonist nor-BNI, but not by the selective kappa agonists U50, 488 or dynorphin. These findings indicated that the amino-terminus of the kappa receptor likely has the antagonist binding site but not the agonist binding site. The agonist binding site, thus, likely resides in other regions of the receptor, such as the third and fourth extracellular domains, which have different amino acid sequences from the delta receptor. These data further indicate that agonists and antagonists bind to clearly dissociated regions of the kappa receptor.

The finding that the naloxone binding site is in the amino-terminal region of the kappa receptor suggests that a limited region of the kappa receptor may be similar to the mu receptor. Naloxone potently binds to mu opioid receptors as well as kappa receptors. These data indicate that screening cDNA libraries with probes against the amino-terminus of the kappa receptor will facilitate cloning of the mu receptor.

Both the selective delta agonist [$^3$H]-DPDPE and the selective delta antagonist [$^3$H]-naltrindole potently bound to the chimeric kappa$_{1-74}$/delta$_{65-372}$. These data indicate that their binding sites are not in the N-terminus of the delta receptor, because this chimera does not have an amino-terminus of the delta receptor. Their binding sites likely reside in other parts of the delta receptor.

X. Ligand Binding and G Protein Coupling Domains of the Kappa and Delta Opioid Receptors A. Ligand Binding Domains The kappa and delta opioid receptors exhibit distinct pharmacological specificities. The N-terminal extracellular regions of the two receptors are divergent in amino acid sequence. Mutagenesis techniques are used to exchange the N-termini of each receptor. The mutant cDNAs are transfected into suitable host cells (e.g., COS cells) and the chimeric receptors tested for their ability to bind kappa and delta subtype-selective agonists and antagonists. For the mutagenesis, an SpeI restriction site in the first transmembrane spanning region is engineered into the mouse kappa receptor and delta receptor cDNAs using oligonucleotide-directed mutagenesis. The site is engineered into identical locations in both cDNAs thereby avoiding frameshifts and/or deletions or additions of sequence. There are no naturally occurring SpeI restriction sites in the coding regions of either the kappa or delta opioid receptor cDNAs. Therefore, after cutting at this newly engineered site in both cDNAs, it is possible to isolate the fragments corresponding to the N-termini of each receptor and ligate them to the purified cDNA corresponding to the C-terminus of the opposite receptor to generate chimeric kappa 1-74/delta 65-372 and delta 1-64/kappa 75-380 receptors. Each mutant DNA fragment is subcloned into a suitable mammalian expression vector (e.g., pCMV6c) and either transiently transfected into COS-7 cells or stably expressed in CHO cells.

The kappa 1-74/delta 65-372 chimera is tested for its ability to be labeled with the delta receptor selective agonist [$^3$H]-DPDPE and the antagonist [$^3$H]-naltrindole, which bind potently to the wild-type delta receptor, and the kappa selective agonist [$^3$H]-U69,593 and the antagonist [$^3$H]-naloxone, which bind to the cloned kappa but not the cloned delta opioid receptor. If the delta opioid receptor radioligands do not bind to this chimeric receptor, but [$^3$H]-U69,593 and [$^3$H]-naloxone do bind with high potency, the ligand binding region of the both receptors is likely included in the N-terminus. Similar pharmacological analysis of the delta 1-64/kappa 75-380 chimera serve to further establish whether the ligand binding domains of both receptors are localized to their N-termini.

Differences likely also exist in the ability of agonists and antagonists to bind to the chimeric receptors. Such differences are also examined using mutagenesis. By way of example, if the delta selective agonist [$^3$H]-DPDPE does not bind to the kappa 1-74/delta 65-372 chimera whereas [$^3$H]-U69593 does, it is likely that that [$^3$H]-DPDPE would bind potently to the delta 1-64/kappa 75-380 chimera, but [$^3$H]-U69593 would not. Conversely, if [$^3$H]-naltrindole and [$^3$H]-naloxone bind similarly to the chimeric and wild-type receptors, then the results would support the hypothesis that antagonists bind to different regions of the opioid receptors than agonists.

To further identify and isolate the ligand binding domains of the two receptors in the N-terminal regions, smaller regions of the N-termini are exchanged and the mutant receptors tested for their affinities for kappa or delta agonists or antagonists.

If the initial studies reveal that the N-termini do not contain the ligand binding domains, it is likely that either the third and fourth extracellular domains (the only two other extracellular regions in the opioid receptors which differ significantly in amino acid sequence) serve as ligand binding domains. These regions correspond to residues 197–220 and 300–311 of the kappa receptor and residues 187–208 and 287–298 of the delta opioid receptors. The third and fourth extracellular domains of the receptors are exchanged between the two receptors and the mutant receptors tested for their ability to bind kappa and delta receptor agonists and antagonists.

Mouse kappa and delta opioid receptor cDNA are mutated using the Altered Site™ in vitro Mutagenesis System (Promega Corp. Madison Wis.). To engineer in the SpeI restriction site at residues 78–80 in the first transmembrane spanning regions of the kappa receptor cDNA, the mouse kappa receptor cDNA is subcloned into the phagemid pALTER™ and with the helper phage R408, single-stranded template is produced. A 24-mer oligonucleotide (GTGGGCAATTCACTAGTCATGTTT; SEQ ID NO:7) encoding the desired mutation (TCTGGT to ACTAGT) is annealed to the single-stranded template and elongated with T4 DNA polymerase. The heteroduplex DNA is then used to transform the repair-minus *E. coli* strain BMH 71-18 mut S. Transformants are selected by growth in LB plates containing 125 μg/ml ampicillin. Double-stranded plasmid DNA is sequenced by the Sanger dideoxy chain termination method and digested with SpeI to confirm the presence of the mutation. For the delta receptor cDNA, a 24-mer oligonucleotide (CTGGGCAACGTACTAGTCATGTTT; SEQ ID NO:8) encoding the desired mutation (GCTCGT to ACTAGT) is used and similar procedures as described above for the kappa receptor cDNA are employed.

Each mutated cDNA is excised from pALTER™ with EcoRI/SalI in the case of the delta receptor cDNA and SalI and BamHI for the kappa receptor cDNA and subcloned into the corresponding sites in a suitable mammalian expression vector (e.g., pCMV6c). The 5' regions of each cDNA corresponding to the N-terminal regions of each receptor (residues 1–75 in the kappa receptor and 1–65 in the delta receptor) are excised with EcoRI/SpeI (delta receptor) and SalI/SpeI (kappa receptor) and gel purified. The N-terminal fragment of the delta receptor is ligated to the C-terminal fragment of the kappa receptor and the N-terminal fragment of the kappa receptor is ligated to the C-terminal region of the delta receptor. The inserts are excised from the vector and their size determined by agarose gel electrophoresis to establish whether appropriate ligation occurred.

The chimeric receptor cDNA is then transiently transfected into COS-7 cells by a calcium- phosphate mediated procedure. The chimeric receptors in which the third or fourth extracellular loops are exchanged between the kappa and delta opioid receptors is generated by PCR™ using a similar approach as described above.

For the receptor binding studies, chimeric receptors are labeled with the radioligands [$^3$H]-U69593, [$^3$H]-naloxone, [$^3$H]-DPDPE and [$^3$H]-naltrindole. Specific binding is defined as naloxone-sensitive tissue binding. Competitive inhibition studies are performed using a number of kappa ligands such as U50488, U69593, nor-BNI and dynorphin. Stereospecificity of binding is tested using the isomers of naloxone and by comparing the potencies of levorphanol and dextorphan at inhibiting binding. Delta receptor ligands such as DPDPE, DSLET, enkephalin, deltorphin and BW373U86 and the antagonists naltrindole, NTB and BNTX are also tested. Analysis of IC$_{50}$ values is determined using the computer curve fitting program PROPHET.

The effects of GTPγS on either radiolabeled agonist binding or agonist inhibition of radiolabeled antagonist binding are studied to determine whether the mutant receptors are G protein-coupled. To investigate the functional activity of the mutant receptors, the ability of the receptors to mediate agonist inhibition of forskolin-stimulated cAMP formation is determined as described using standard techniques.

B. G Protein Coupling Domains

G proteins couple the opioid receptors to various effector systems and are therefore critical in mediating the cellular actions of the opioids. The regions of the receptors involved in associating with G proteins have not been previously identified. For the adrenergic and muscarinic receptors, several different intracellular domains have been identified as being involved in G protein association (Dohlman et al., 1991). The third intracellular loop of these receptors was first proposed to interact with G proteins. The amino acid sequences of the third intracellular loops of the kappa and delta opioid receptors are very similar (see below). Therefore, exchanging the third intracellular loops of the kappa and delta opioid receptors would be unlikely to provide any significant information on whether these regions are G protein coupling domains. However, the kappa and delta opioid receptors have high amino acid sequence similarity with the somatostatin receptor subtype SSTR1 with 40% amino acid identity overall. Furthermore, the third intracellular loops of opioid receptors and SSTR1 are identical in size (28 amino acids for each) but differ in sequence (see below).

It has been shown that SSTR1 does not couple with G proteins, nor does it mediate agonist inhibition of adenylyl cyclase activity (Rens-Domiano et al., 1992; Yasuda et al., 1992). As a result, the third intracellular loop of SSTR1 is not likely to contain sequences required for G protein coupling. The third intracellular loops of the kappa and delta receptors are exchanged with the corresponding region of SSTR1 by site-directed mutagenesis to determine if they are G protein coupling domains. If the third intracellular loops of the opioid receptors is a G protein coupling domain, the chimeric opioid receptors likely will lose their ability to associate with G proteins. On the other hand, the chimeric SSTR1 should gain an ability to couple to G proteins. G protein association with the chimeric receptors is tested by the effects of GTPγS on agonist binding to the receptor, the effect of pertussis toxin treatment on agonist binding and on the ability of the chimeric receptors to mediate agonist inhibition of cAMP formation. Expression of the chimeric opioid receptors is detected with both radiolabeled antagonist and agonist binding. Chimeric SSTR1 expression is detected with [$^{125}$I]-Tyr$^{11}$ somatostatin binding as previously described (Raynor and Reisine, 1989).

Third Intracellular loops

SSTR1  Leu Ile Ile Ala Lys Met Arg Met Val Ala Leu Lys Ala Gly Trp
       Gln Gln Arg Lys Arg Ser Glu Arg Lys Ile Thr Leu Met
       (SEQ ID NO:13).

Kappa  Leu Met Ile Leu Arg Leu Lys Ser Val Arg Leu Leu Ser Gly Ser
       Arg Glu Lys Asp Arg Asn Leu Arg Arg Ile Thr Lys Leu
       (SEQ ID NO:14).

Delta  Leu Met Leu Leu Arg Leu Arg Ser Val Arg Leu Leu Ser Gly Ser
       Lys Glu Lys Asp Arg Ser Leu Arg Arg Ile Thr Arg Met
       (SEQ ID NO:15).

Second Intracellular loops

SSTR1  Asp Arg Tyr Val Ala Val Val His Pro Ile Lys Ala Ala Arg Tyr
       Arg Arg Pro (SEQ ID NO:16).

Kappa  Asp Arg Tyr Ile Ala Val Cys His Pro Val Lys Ala Leu Asp Phe
       Arg Thr Pro (SEQ ID NO:17).

Delta  Asp Arg Tyr Ile Ala Val Cys His Pro Val Lys Ala Leu Asp Phe
       Arg Thr Pro (SEQ ID NO:17).

The second intracellular loop of some receptors has also been proposed to contribute to G protein coupling (Dohlman et al., 1991). This region of the kappa and delta opioid receptors is identical (See above). However, the sequences differ from those in SSTR1. The second intracellular loop can contain a G protein coupling domains of the opioid receptor. These regions are exchanged with SSTR1 and the chimeric opioid receptors tested for loss of G protein coupling and the chimeric SSTR1 tested for gain of G protein association.

A third potential region of the opioid receptors that may be involved in G protein coupling is the cytoplasmic tail. This is the only intracellular domain that differs in amino acid sequence between the two opioid receptors. While both opioid receptors couple to pertussis toxin sensitive G proteins, the subtypes of G proteins with which they associate are likely different. If these receptors can interact with different G proteins, then the unique sequences of the C-termini of the opioid receptors likely provides the structural basis for their ability to interact with different G proteins. These regions are exchanged with the corresponding region of SSTR1 and the chimeric receptors tested for G protein association using radioligand binding techniques and for their ability to mediate agonist inhibition of adenylyl cyclase activity.

The C-termini of the kappa and delta opioid receptors are exchanged to determine whether the C-termini are involved in subtle differences in the ability of the kappa and delta receptor to associate with subtypes of G proteins. The chimeric and wild-type receptors are then stably expressed in suitable host cells (e.g., CHO cells or PC12 cells). The chimeric receptors are then tested for which G proteins they associate with using an immunoprecipitation approach. Furthermore, the coupling of the chimeric receptors to different effector systems, such as adenylyl cyclase, $Ca^{++}$ and $K^+$ channels is also analyzed to determine whether the C-termini direct the receptors to couple to selective G proteins to regulate specific effector systems.

To construct the hybrid kappa receptor/SSTR1 or delta receptor/SSTR1 mutants in which the third intracellular loop of SSTR1 is exchanged with a similar region of the kappa and delta receptor, PCR is employed. Three fragments, the N-termini, C-termini and third intracellular loops of SSTR1, the delta and kappa receptors are amplified from 10–50 ng of plasmid DNA under the following conditions: 25–30 cycles consisting of 1 min at 95° C., 1 min at 55° C. and 1 min at 72° C.

N-terminal fragment: The N-terminal fragments is be generated with a forward primer spanning a unique SalI site in the cDNA for SSTR1, EcoRI site of the delta receptor and SalI site for the kappa receptor. The reverse primer is made to the 3' end of the fifth membrane-spanning region of SSTR1, the delta and kappa receptors. Digestion of the SSTR1, delta and kappa receptor N-terminal products with SalI, EcoRI and SalI, respectively, yields DNA fragments with 5' overhangs and 3' blunt ends. The forward (F) and reverse (R) primers to be used in PCR™ amplification of the N-terminal fragment (N-) include the following:

| SSTR1 | N-F = TATCTAGGTC GACGG; (SEQ ID NO:18), |
|---|---|
| SSTR1 | N-R = CATCTTAGCA ATGAT; (SEQ ID NO:19), |
| delta receptor | N-F = GTCGAGAATT CCCCG; (SEQ ID NO:20), |
| delta receptor | N-R = CAGGCGCAGT AGCAT; (SEQ ID NO:21), |
| kappa receptor | N-F = TAGGTCGACG GTATC (SEQ ID NO:22), and |

-continued

| kappa receptor | N-R = CAGGCGCAGG ATCAT (SEQ ID NO:23). |
|---|---|

Third intracellular loop: The third intracellular loop (3-i-loop) is amplified using a forward primer encoding the 5' end of the 3-i-loop of SSTR1, delta and kappa receptors and a reverse primer spanning the juncture between the 3-i-loop and the C-terminal fragment. This primer incorporates the restriction site MboI at identical positions within SSTR1, the delta and kappa receptor cDNA. Digestion of SSTR1, delta and kappa receptor third intracellular loop PCR™ fragments with MboI produces DNA with 5' blunt ends and 3' MboI overhangs. Primers used in PCR™ amplification of the 3-i-loop include the following:

| SSTR1 | 3-i-loop-F = CGCATGGTGGCCCTC; (SEQ ID NO:24), |
|---|---|
| SSTR1 | 3-i-loop-R = GGTGATCTTGCGCTC; (SEQ ID NO:25), |
| delta receptor | 3-i-loop-F = CGCAGCGTGCGTCTG; (SEQ ID NO:26), |
| delta receptor | 3-i-loop-R = CGTGATCCGCCGCAG; (SEQ ID NO:27), |
| kappa receptor | 3-i-loop-F = AAGAGTGTCCGGCTC; and (SEQ ID NO:28), |
| kappa receptor | 3-i-loop-R = GGTGATCCGGCGGAG; (SEQ ID NO:29). |

C-terminal fragment: The C-terminal fragment is be generated with a forward primer that spans the juncture between the 3-i-loop and the C-terminal fragment and a reverse primer that encodes a unique EcoRI site for SSTR1, SalI site for the delta receptor and XbaI site for the kappa receptor. The forward primer encodes an MboI site, just as the reverse primer of the 3-i-loop fragment does. This provides directional ligation of the 3-i-loop with the C-terminal fragment. Digestion of the C-terminal products of SSTR1, the delta and kappa receptors with EcoRI, SalI and XbaI, respectively, and MboI yields DNA fragments with 5' MboI overhangs and their respective 3' overhangs. The following primers are used in PCR™ amplification of the C-terminal fragment (C-):

| SSTR1 | C-F = GAGCGCAAGATCACC; (SEQ ID NO:30), |
|---|---|
| SSTR1 | C-R = TCGAGAATTCCCCGG; (SEQ ID NO:31), |
| delta receptor | C-F = CTGCGGCGCGATCAC; (SEQ ID NO:32), |
| delta receptor | C-R = TAGGTCGACGGTGTGG (SEQ ID NO:33), |
| kappa receptor | C-F = CTCCGGCGGATCACC; (SEQ ID NO:34), and |
| kappa receptor | C-R = GGGTCGAGAACTAGT; (SEQ ID NO:35). |

After PCR™ amplification and digestions, the N- and C-terminal fragments of SSTR1 are joined with the third intracellular loop of the delta or kappa receptor and ligated into pCMV-6b (that has been digested with SalI and EcoRI) in the presence of T4 DNA ligase at 16° C. for 24 hrs. Once the hybrid is appropriately ligated into the expression vector, the entire insert is sequenced using the Sanger dideoxy chain termination method (Sequenase version 2.0, USB) as described by the manufacturer. This procedure is repeated for the delta and kappa receptor containing the third intracellular loop of SSTR1. It should be noted that the C-terminal fragments of the delta and kappa receptor have 1 and 2 endogenous MboI sites, respectively. The inserts of the delta and kappa receptors have previously been subcloned into the phagemid pALTER™. By oligonucleotide-directed mutagenesis (Altered Sites, Promega), these endogenous MboI sites are destroyed by single nucleotide changes that do not alter amino acid sequence. This is carried out prior to PCR™ amplification.

Exchange of the second intracellular loop is carried out in analogous fashion to the third intracellular loop exchange. The C-terminal exchanges are carried out in an analogous fashion as the N-terminal exchanges in which a common restriction site is engineered into the same corresponding site of SSTR1, the delta and kappa receptor and the appropriate restriction enzyme are used to digest the C-terminal fragment from each receptor and then the C-terminal fragment of SSTR1 is ligated to either the remainder of the kappa or delta receptor or the C-terminal fragment of the opioid receptors is ligated to the remainder of SSTR1.

The chimeric receptors are stably expressed in suitable host cells (e.g., CHO and PC12 cells) and tested for G protein coupling by the ability of GTP analogs to reduce high affinity agonist binding to each receptor. The kappa receptor is labeled with [$^3$H]-U69,593, the delta receptor is labeled with [$^3$H]-DPDPE and the chimeric SSTR1 labeled with [$^{125}$I]-Tyr$^{11}$SRIF as previously described (Rens-Domiano et al., 1992; Yasuda et. al., 1992). The chimeric receptors are also tested for their ability to mediate agonist inhibition of forskolin stimulation of cAMP formation.

XI. Identification of the G Proteins and Cellular Effector Systems Coupled to the Kappa and Delta Opioid Receptors A. G Proteins Coupled to Opioid Receptors Both kappa and delta opioid receptors couple to multiple cellular effector systems. G proteins are necessary to link many receptors to cellular effector systems. We have developed a biochemical approach to directly determine which G proteins physically associate with the opioid receptors. This approach has been employed to identify the Gi and Go subtypes associated with the SRIF receptors and the alpha2a adrenergic receptors (Law et al., 1991, 1993; Law and Reisine, 1992; Okuma and Reisine, 1992). Briefly, the approach involves (1) solubilizing the receptors from tissue sources expressing the receptor with a mild detergent CHAPS to maintain receptor/G protein association, (2) centrifuging at high speed to remove unsolubilized material, and immunoprecipitating the receptor/G protein complex with peptide-directed antisera against either Gi$\alpha$1 (3646), Gi$\alpha$2 (1521), Gi$\alpha$3 (1518), Go$\alpha$1 or Go$\alpha$2. The antisera have been generated and provided by Dr. D. Manning (Dept. Pharmacology, Univ. PA) and are directed against internal sequences of the alpha subtypes. The antisera are selective for each alpha subunit, based on their specificities determined with recombinant forms of the alpha subunits, and the antisera are equally effective at immunoprecipitating the alpha subunits as determined by there ability to immunoprecipitate alpha subunits metabolically labeled with [$^{35}$S]-methionine. Following imnmunoprecipitation, the immunoprecipitate is separated from the supernatant and high affinity agonist binding to either the immunoprecipitated receptor or the solubilized receptor remaining in the supernatant can be performed. Specificity of the immunoprecipitation is determined using the peptides to which the antisera where generated to block the immunoprecipitation. The delta opioid receptor is labelled using [$^{125}$I]-beta-endorphin because it is one of the most potent agonist available at binding to the delta receptor and its high specific activity facilitates detection of the receptor. Furthermore, labeling the receptor with agonists assures that the receptor detected is G protein coupled since the affinity of the G protein uncoupled receptor for agonists is low. The solubilized and immunoprecipitated delta receptor is also labelled with the antagonist [$^3$H]-naltrindole. To label the kappa receptor, the high affinity agonist [$^3$H]-U69,593 and the antagonist [$^3$H]-naloxone are employed. For tissue sources, we have stably expressed both the delta and kappa opioid receptors in CHO cells and PC12 cells. These studies allow us to determine which G proteins physically associate with the cloned delta and kappa opioid receptors.

For these studies, we use similar methodology as we have employed to study G protein coupling to SRIF and alpha2 adrenergic receptors (see Law et al., 1991, 1993: Okuma and Reisine, 1992. Either CHO (DG44) or PC12 cells stably expressing either the cloned delta or kappa receptors are solubilized with a buffer containing the non-ionic detergent CHAPS (20 mM CHAPS, 20% glycerol, 250 mM PMSF and buffer A which consists of 50 mM Tris-HCl (pH 7.8), 1 mM EGTA, 5 mM MgCl2, 10 $\mu$g leupeptin, 2 $\mu$g pepstatin and 200 $\mu$g bacitracin. Following solubilization, the solution is centrifuged at 100,000×g for 60 min at 4° C. and the supernatant removed and diluted 1:5 in 7.5% glycerol, 0.5 $\mu$g/ml aprotinin in buffer A. The sample is then concentrated using an Amicon 8050 ultrafiltration device. To immunoprecipitate opioid receptor/G protein complexes, the solubilized receptors is incubated with an aliquot of G protein specific antisera, the samples are placed in a rotator at 4° C. for 4–6 hrs. 100 $\mu$l of 50% (w/v) protein A sepharose beads are then added to the samples and incubated overnight. Another aliquot of antisera is subsequently added bringing the total antisera dilution to 1:20 which is the optimal concentration of antisera that immunoprecipitates somatostatin and alpha2 receptor/G proteins complexes. The samples are incubated for 3 hrs and then centrifuged at 10,000 rpm for 2 min in an Eppendorp microcentrifuge. The supernatant is removed and tested for the presence of opioid receptor using a binding assay described below. The immunoprecipitate is resuspended in buffer A and centrifuged again. The supernatant is removed and the immunoprecipitate resuspended in buffer A and the presence of opioid receptor detected with a binding assay described below.

Solubilized opioid receptors are detected by radioligand binding assay. For the delta receptor, [$^{125}$I]-beta-endorphin is typically used to label the receptor. Specific binding is determined by DSLET (1 $\mu$M) or naltrindole (1 $\mu$M) displaceable binding. The binding reaction is at 25° C. and is terminated by adding 9 ml of cold Tris-HCl buffer (pH 7.8) to the reaction mixture and filtering the samples under vacuum. The bound radioactivity is analyzed using a gamma counter. Parallel studies are conducted using [$^3$H]-naltrindole. [$^3$H]-naltrindole is used to determine the total amount of solubilized delta receptor present, since its binding is not dependent on G protein coupling. In contrast, [$^{125}$I]-beta-endorphin only detects the presence of G protein coupled receptor. To detect immunoprecipitated delta opioid receptors, the immunoprecipitated receptor is resuspended in Tris-HCl (pH 7.8) buffer and similar binding assays as described above are performed. To detect solubilized and immunoprecipitated kappa opioid receptors, the agonist [$^3$H]-U69,593 is used to detect kappa receptor/G protein complexes and [$^3$H]-naloxone is used to detect total kappa receptor present.

The G protein-directed antisera used are the same employed previously to study SRIF and alpha2 adrenergic receptor/G protein coupling. The antiserum 8730 is directed against the C-terminus of Giα and recognizes all forms of Giα. The Giα subtype selective antisera used are 3646 (Giα1), 1521 (Giα2) and 1518 (Giα3). These antisera are directed against internal regions of Giα. Their selectivity has been established on their specificity towards recombinant forms of the Giα subtypes. The antisera 9072 and 2353 are directed against the C-terminus and an internal region of Goα, respectively. They selectively interact with Goα. The Goα1 and Goα2 antisera used to distinguish which splice variant of Goα the opioid receptor interact with have been generated against the peptides Glu Tyr Pro Gly Ser Asn Thr Tyr Glu Asp (SEQ ID NO:36) and Glu Tyr Thr Gly Pro Ser Ala Phe Thr Glu (SEQ ID NO:37) which correspond to residues 290–299 of the Goα subtypes (Law et al., 1993).

XII. The Molecular Basis of Agonist Regulation of Opioid Receptors and Their mRNA While acute stimulation of opioid receptors can induce analgesia, chronic exposure of the receptors to agonists can induce tolerance (Koob and Bloom, 1992). The specific neurochemical mechanisms involved in these behavioral phenomena are not known. However, a number of studies have linked tolerance development to opioid receptor desensitization (Nestler, 1993, Loh and Smith, 1990; Childers, 1988). Delta opioid receptors in cell lines and in animals have been reported to desensitize following chronic exposure to opioid agonists (Law et al., 1983–85). Furthermore, we have found that the cloned delta opioid receptor expressed in COS or CHO cells desensitizes following agonist pretreatment (unpublished results). Studies in rodents have also suggested that kappa receptors can be modulated by chronic opioid treatment. We have shown that the cloned kappa receptors expressed in COS cells are desensitized following agonist pretreatment.

While short-term opioid treatment can induce opioid receptor desensitization, prolonged exposure of cells in culture to opioids or long-term treatment of animals with opioids causes opioid receptor downregulation. Downregulation involves an inactivation of the receptor due to its internalization or degradation. This has been most clearly established for delta opioid receptors expressed in NG-108 cells (Law et al., 1984, 1985). For many hormone and neurotransmitter receptors, receptor desensitization and downregulation are linked, both in a temporal and molecular manner (Hausdorff et al., 1992).

For many neurotransmitters and hormones, receptor down-regulation can cause a number of long-term adaptive cellular responses. One of the most clear-cut changes is modification in the expression of genes encoding the receptors that are downregulated. While chronic opioid treatments have been reported to cause opioid receptor down-regulation, little is known about the adaptive cellular responses following chronic opioid use.

A. Molecular Basis of Opioid Receptor Desensitization

Pretreatment of COS cells expressing the cloned kappa receptor to agonists desensitizes the kappa receptor. The enzyme BARK is involved in kappa receptor desensitization because in cells coexpressing the kappa receptor and a dominant negative BARK mutant, agonist pretreatment did not cause kappa receptor desensitization. BARK catalyzes the phosphorylation of a number of agonist occupied receptors and the phosphorylation has been linked to the agonist induced desensitization of those receptors, since phosphorylation has been shown to uncouple receptors from G proteins and effector systems (Hausdorff et al., 1992; Benovic et al., 1989). Peptides directed antisera against the kappa receptor are generated and used to test whether the kappa receptor becomes phosphorylated during desensitization and whether BARK is involved in catalyzing the phosphorylation. We have already synthesized two peptides, corresponding to the C-terminus (Thr Val Gln Asp Pro Ala Ser Met Arg Asp Val Gly; SEQ ID NO:38, residues 367 to 378) and N-terminus (Ser Pro Ile Gln Ile Phe Arg Gly Asp Pro Gly Pro Thr Cys Ser; SEQ ID NO:39, residues 3 to 17) of the kappa receptor. These sequences are unique regions of the kappa receptor, and do not correspond to any other sequences available in the Genbank database. The peptides are used to generate antisera using the same approach employed to generate peptide directed antisera against the SRIF receptors. The antisera are tested for their ability to immunoprecipitate solubilized kappa receptors, detected using radioligand binding techniques, and for their ability to immunoprecipitate kappa receptors in transfected COS cells metabolically labeled with [$^{35}$S]-methionine. Specificity of the antisera is determined by the ability of the peptides to which they were generated to block the ability of the antisera to immunoprecipitate the receptors. The antisera is also tested for their ability to selectively detect the cloned kappa receptor by immunoblotting using COS or CHO cells transiently or stably expressing the kappa receptor, respectively.

Once the specificity of the antisera have been characterized, they are used to determine whether the kappa opioid receptor becomes phosphorylated during desensitization. For these studies, either COS or CHO cells expressing the kappa receptor are preloaded with [$^{32}$P]-orthophosphate. The cells are treated for varying times (1, 5, 10, 15, 30, 45 min and 1, 2 and 4 hrs) with U50,488, the treatment stopped and the cells solubilized and the kappa receptors immunoprecipitated. The immunoprecipitated receptors are then subjected to SDS-PAGE and autoradiography to determine whether they are phosphorylated. The N-terminal directed antisera should be able to recognize both the phosphorylated and non-phosphorylated receptors equally well since its epitope is in an extracellular domain that is not accessible to intracellular kinases and therefore should not be obstructed by phosphate groups. The C-terminal directed antisera are also used to immunoprecipitate the receptor. It may be affected by phosphorylation, if phosphorylated residues are near the antiseras epitope. If it is unable to immunoprecipitate the phosphorylated receptor whereas the N-terminal directed does, then the results suggest that regions of the C-terminus are phosphorylated. If the receptor becomes phosphorylated, the specificity of the reaction is tested by determining whether nor-BNI can block the agonist induced phosphorylation, just as it can block agonist induced desensitization. The role of BARK in the phosphorylation is tested by determining whether the BARK dominant negative mutant prevents the receptor from becoming phosphorylated, just as it prevents kappa receptor desensitization.

If the BARK dominant negative mutant blocks agonist induced kappa receptor phosphorylation, regions within the kappa receptor that are phosphorylated and involved in kappa receptor desensitization are identified using standard techniques. Phosphorylation likely occurs at intracellular domains of the receptor since these are regions that would be accessible to BARK. Exchange mutagenesis is used to localization regions within the kappa receptor that may be phosphorylated and involved in desensitization. Our previous studies have shown that the SRIF receptor SSTR1 does not desensitize following chronic agonist treatment and therefore would not be expected to be phosphorylated in an agonist dependent manner (Rens-Domiano et al., 1992). This receptor has 40% identity in amino acid sequence with the kappa receptor. Previously generated series of kappa receptor/SSTR1 exchange mutants, the second and third intracellular loops and the cytoplasmic tail are the major intracellular domains of the two receptors and are the regions of the kappa receptor likely to be phosphorylated since they contain multiple serine and threonine residues, which are acceptors of BARK catalyzed phosphorylation. Treatment of CHO cells expressing the chimeric kappa receptor/SSTR1 with kappa agonists (U50,488) is used to test phosphorylation of the receptors. For these studies, CHO cells stably expressing the mutant receptors are pre-loaded with [$^{32}$P]-orthophosphate and following the agonist treatments, the cells are solubilized and the chimeric receptors immunoprecipated with antisera directed against the N-terminal region of the kappa receptor, which is an epitope that should not be disturbed by the receptor mutagenesis. Once chimeras that are not phosphorylated following agonist pretreatment are identified, single point mutations of the serines and threonines in the wild-type kappa receptor are induced in those regions that had been exchanged in chimeric receptors. The mutant receptors are tested for their ability to desensitize following chronic agonist treatment and whether they become phosphorylated in response to agonist stimulation.

We have already synthesized (Dr. S. Khan, peptide synthesis facility, Wistar Inst. Philadelphia, Pa.) the peptides Ser Pro Ile Gln Ile Phe Arg Gly Asp Pro Gly Pro Thr Cys Ser (SEQ ID NO:39), and Thr Val Gln Asp Pro Ala Ser Met Arg Asp Val Gly (SEQ ID NO:38), which correspond to unique sequences in the N- and C-terminus of the kappa receptor. The peptides are covalently linked to Keyhole Limpet Hemocyanin (KLH) protein as a carrier using a bifunctional coupling reagent, glutaraldehyde. Peptide-KLH conjugates are emulsified in the presence of Freund's Complete Adjuvant for the first injection, followed by incomplete Adjuvant for the next injections. New Zealand rabbits receive subcutaneous injections every four weeks and are bled 10 days after each immunization.

Membranes from either CHO cells or COS cells expressing the cloned kappa receptor and control cells are subjected to 8% SDS-PAGE, the proteins transferred to nitroscreen membrane, and the membranes saturated at 37° C. for 2 hr with 5% defatted milk, 0.02% azide and PBS. Varying dilutions of the antisera (1:10 to 1:10,000) in 5% milk/PBS are incubated with the membranes over night at 4° C. under continuous shaking, the nitrocellulose membranes are then washed and the complexed antibodies detected with a phosphatase alkaline labeled anti-rabbit antibody kit. Non-specific reactions are determined by specific peptide blockade. Preimmune sera is also used as a control for specificity.

Kappa receptors in COS or CHO cells are solubilized and incubated overnight in the presence of the antisera precoated Protein A-Sepharose beads (20 µl serum for 20 µl of a 50% protein A-Sepharose beads/50% PBS solution) at 4° C. The supernatants and immunoprecipitates are analyzed for the presence of high affinity [$^3$H]-U69593 and [$^3$H]-naloxone binding. In addition, the receptor is metabolically labelled with [$^{35}$S]-methionine, as described in Theveniau et al., 1992 and immunoprecipitated with antisera. For these studies, COS or CHO cells expressing the cloned kappa receptor are incubated overnight in methionine-free medium containing 0.5 mCi of [$^{35}$S]-methionine. The cells are washed with PBS, and the proteins solubilized in RIPA buffer. The receptor is immunoprecipitated by an overnight incubation with antibody-coated protein A beads. The immunoprecipitate is boiled in sample buffer and subjected to 10% SDS-PAGE and autoradiography.

Either COS or CHO cells expressing the kappa receptor or the chimeric kappa receptor/SSTR1 are incubated with 0.3 mCi of [$^{32}$P]-orthophosphate for 24 hrs to determine which receptor is phosphorylated during desensitization. The cells are then stimulated with U50488 for varying times (0, 5, 15, 30, 45, 60, 90, 120, or 240 min). The reaction is stopped, the cells washed with cold PBS, the membranes solubilized as described above and the receptor immunoprecipitated with the peptide directed antisera. The immunoprecipitate is subjected to SDS-PAGE and autoradiography to determine whether the receptor is phosphorylated. Specificity of the immunoprecipitation is demonstrated by blocking with the peptide to which the antisera whether generated and the lack of phosphorylation of the kappa receptor in control, non-treated cells.

B. Molecular Basis of Delta Opioid Receptor Desensitization

Like kappa receptors, delta opioid receptors desensitize following chronic agonist pretreatment. The cloned delta receptor stably expressed in CHO cells desensitizes following chronic agonist pretreatment. The desensitization is characterized as a decrease in affinity of the receptors for agonists, an uncoupling of the receptors from G proteins and a diminished ability of the delta receptor to mediate agonist inhibition of cAMP formation. Studies similar to those described above for the kappa receptor are performed to test whether the delta receptor expressed in COS cells become desensitized following agonist treatment.

For these studies, peptide-directed antisera against the cloned delta receptor are generated using the peptides (Ser Asp Ala Phe Pro Ser Ala Phe Pro Ser Ala Gly Ala; SEQ ID NO:40), and (Ala Thr Thr Arg Glu Arg Val Thr Ala Cys Thr Pro Ser; SEQ ID NO:41), which correspond to the residues 20 to 32 and 367 to 379 in the N- and C-termini respectively. The antisera are then used to determine whether the delta receptor becomes phosphorylated during desensitization. For these studies the cloned delta receptor is expressed in COS and CHO cells, the cells are preloaded with 32P-orthophosphate and stimulated for varying times [1, 5, 10, 15, 30 and 60 min) with DSLET (1 µM)]. The cells are then solubilized and the delta receptor immunoprecipitated with the antisera. The immunoprecipitate is subjected to SDS-PAGE and autoradiography to determine whether the receptor becomes phosphorylated. Similar studies are performed on COS cells cotransfected with the delta receptor and the BARK dominant negative mutant to determine whether BARK is involved in the phosphorylation of the delta receptor.

To determine regions of the delta opioid receptor that become phosphorylated during desensitization, similar approaches as described for the kappa receptor are used with delta opioid receptor/SSTR1 chimeric receptors. Where chimeras do not become phosphorylated, point mutations are induced in the wild-type receptor to convert the serines and threonines in the corresponding region that was exchanged with SSTR1. The mutated delta receptor is then tested for its ability to be desensitized following agonist pretreatment and whether it becomes phosphorylated.

XIII. Expression of the Opioid Receptor Genes

Chronic opioid treatment induces a number of adaptive cellular responses. For some neurotransmitters and hormones, chronic exposure of target cells or tissues to agonists can induce long-term changes in the expression of receptor genes. There is no information available to date concerning the long-term effects of opioid treatment on the expression of the delta and kappa opioid receptor genes.

NG-108 cells, which endogenously express delta opioid receptors (Law et al., 1983), are treated with delta agonists to desensitize and downregulate the receptor and determine whether accompanying changes occur in the expression of the delta opioid receptor gene. Changes in delta receptor gene expression are measured by Northern analysis employing delta receptor specific probes. NG-108 cells are treated for varying times (5, 15, 45, 60 min, 2, 4, 8, 16 and 24 hrs) with the delta selective agonist DPDPE (1–100 nM). Where DPDPE treatment alters delta receptor mRNA levels, the ability of other agonists (DSLET, deltorphin and bremazocine) to induce this effect are studied. These studies test whether a cellular response to chronic delta receptor agonist treatment is a change in delta receptor gene expression.

To investigate whether chronic treatment with delta opioid selective agonists modifies delta receptor gene expression in vivo, post-mortem, frozen brains of rats and mice that have been chronically treated with DPDPE and made tolerant (antinociception) to this agonist are obtained. The procedures used and scheduling of the drug administrations are the same as previously described (Cowan and Murray, 1990; Heyman et al., 1988). In selected brain regions (cerebral cortex, striatum, hippocampus, and cerebellum) and spinal cord of saline treated controls and DPDPE treated animals, changes in delta opioid receptor mRNA are quantified by Northern analysis. On the same blots, kappa receptor mRNA is reprobed to determine the selectivity of the changes in opioid receptor gene expression. In addition, in other groups of control and treated animals, relative levels of delta opioid receptor mRNA are measured by semi-quantitative in situ hybridization histochemistry. The advantage of the use of in situ hybridization histochemistry to detect changes in delta receptor mRNA as a consequence of chronic delta agonist treatment is the superior anatomical resolution at the regional (film autoradiography) and cellular level (emulsion autoradiography). This is particularly important for analyzing changes in delta receptor mRNA in small nuclei such as the locus coerleus and other brainstem nuclei in which delta receptors have important roles and in which tolerance to delta agonists have been demonstrated (Nestler, 1993). For the in situ hybridization, the sections are processed and applied to film and the optical density of the autoradiograms in selected regions, such as the locus coerleus, substantia nigra, striatum, nucleus accumbens, hippocampus, amygdala, hypothalamus and central grey analyzed. These regions express delta opioid receptor mRNA in mouse brain and have been shown in autoradiographic studies to express delta receptors in rat brain (Herz, 1993). After exposure to film, the sections are dipped in photographic emulsion and the autoradiographic signal determined at the single cell level to confirm the anatomic specificity of the labeling. Quantitation at the single cell level is performed in brain regions where labeling on films is not optimal due to scattering of the labeled cells. Single cell analysis also complements optical density measurements if microscopic analysis suggests heterogeneous effects on subpopulations of neurons in a given regions. Parallel studies are performed to determine whether kappa receptor mRNA is modified in the brains of animals made tolerant to DPDPE to determine the specificity of the effect on delta receptor gene expression. The delta receptor agonist used for these treatments, DPDPE, does not bind to the kappa receptor, nor any other opioid receptor.

A. Selective Changes in Kappa Receptor Gene Expression

There are no cell lines that endogenously express kappa receptors. Furthermore, the COS and CHO cells we have stably expressed the cloned kappa receptor are transfected with the mouse cDNA under a CMV promoter. Therefore, the cDNA is not under the normal control of regulatory regions and factors that would modulate kappa receptor gene expression. Therefore, chronic treatment of rodents with kappa agonists is tested to determine if such agonists can induce changes in kappa receptor gene expression. For these studies, frozen post-mortem brains are obtained from rats and mice treated with U50,488 to induce behavioral tolerance to the antinociceptive actions of kappa agonists using previously described procedures (Cowan and Murray, 1990). Modified kappa receptor gene expression in selective brain regions is made using Northern analysis and by in situ hybridization histochemistry employing kappa receptor selective RNA probes. Results from brain sections of the treated animals are be compared to levels of kappa receptor mRNA detected in brain sections from control, saline treated animals. In adjacent sections, delta opioid receptor mRNA levels are detected to determine whether the treatment selectively effects kappa receptor gene expression. U50,488 does not bind to delta opioid receptors nor any other receptor besides kappa receptors. Therefore, if U50,488 treatments induce selective changes in kappa receptor mRNA levels but not delta receptor mRNA levels, then the changes in kappa receptor gene expression are likely directly linked to activation and modulation of kappa receptors.

B. Effects of Morphine on Opioid Receptor Gene Expression

Morphine binds potently to mu receptors with nM $IC_{50}$ values. However it is impotent at the cloned kappa receptor ($IC_{50}$ 1 $\mu$M) and does not inhibit binding to the cloned delta receptor at 10 $\mu$M. Its selective high affinity for mu receptors suggests that it may not affect kappa or delta opioid receptor gene expression, if changes in expression of the genes is due solely to activation of kappa or delta receptors.

The effects of morphine on kappa and delta opioid receptor mRNA levels in brains sections are studied using in situ hybridization histochemistry and in brain regions by Northern analysis. Frozen post-mortem brains from rats and mice made tolerant to the antinociceptive actions of morphine are obtained using previously described procedures (Tortella et al., 1981; Cowan and Murray, 1990).

NG-108 cells will be exposed to DPDPE (1 $\mu$M) for varying times (0, 5, 15, 45 mins, 1, 2, 4, 8, 16 and 24 hrs). The cells are washed with PBS, detached from flasks and RNA extracted with the guanidinium isothiocyanate-cesium chloride procedure, denatured with glyoxal, fractionated on a 1% agarose gel and transferred to a nylon membranes. The blots are probed with a [$^{32}$P]-labeled fragment of the cloned mouse delta opioid receptor cDNA corresponding to the initial 350 bp of the coding region of the cDNA. After hybridization, the blot is washed at room temperature in 2×SSC and 0.05% SDS at room temperature and then at 48° C. in 0.1×SSC and 0.1% SDS for 30 min. The blot is then exposed to X-ray film in the presence of an intensifying screen at −75° C. As an internal control to account for differences in total RNA per lane, the blot is reprobed with a probe for beta-actin mRNA. Relative levels of delta receptor mRNA are quantitated by densitometry and by excising the bands on the gel containing the mRNA and determining radioactive content by scintillation spectroscopy. If levels of delta receptor mRNA in NG-108 cells are too low to be detected by Northern analysis, reverse-transcriptase PCR™ is used to measure the mRNA levels. Northern analysis for delta opioid receptor mRNA in different rat and mouse brain regions are conducted using similar procedures as described above. Similar procedures are used to detect kappa receptor mRNA using the PstI/EcoRI fragment of the mouse kappa receptor cDNA which corresponds to the initial 375 bp of the cDNA as described by Yasuda et al.

In situ hybridization histochemistry is performed with 35S-radiolabeled RNA probes as previously described (Chesselet et al., 1987). For these studies, brain sections are kept at −70° C., brought to room temperature, acetylated, incubated in Tris/glycine 0.1 M, pH 7.0 and dehydrated in graded ethanol. Hybridization is conducted at 50° C. for 3.5 hr in humid chambers. The hybridization buffer contains 40% formamide, C4×SSC (1×SCC in 15 mM sodium citrate and 150 mM NaCl, pH 7.2), 10% dextran sulfate, 10 mM DTT, tRNA, herring sperm DNA, Denhardt's solution and labeled probe. We have demonstrated that quantitative differences in the level of mRNAs can be reliably detected with these conditions (Weiss-Wunder and Chesselet, 1991). For these studies brain sections from saline treated control animals and the corresponding brain section from the treated animal are processed together. Post-hybridization washes are in 50% formamide/2×SSC at 52° C., for 5, 20 and 25 min. Between the second and third washes, the sections are rinsed in 2×SSC and treated with RNAse A (100 mg/ml) in 2×SSC at 37° C. for 30 min. The sections are rinsed overnight in 2×SSC/Triton X-100® (0.0%), dehydrated in graded ethanol containing 300 mM ammonium acetate and processed for autoradiography. Autoradigrams are quantified as previously described (Soghomomian et al., 1992). Controls include hybridization with sense probes, and verification of the anatomical pattern of hybridization with non-overlapping antisense probes.

For single cell analysis with the Morphon Image analysis system, cells are observed under brightfield illumination with a 100× or a 40× objective and the image magnified and transferred onto a videoscreen. Autoradiographic grains within a defined region are analyzed as previously described (Weiss-Wunder and Chesselet, 1991).

The exact procedures used to treat animals will vary depending upon the animal model. By way of example, male ICR mice (20–25 g, Hilltop Inc., Pa.) are housed eight per cage with food and water freely available. A 12 hr light/12 hr dark daily cycle is maintained. Groups of 8 mice receive s.c. injections of U50,488, morphine or distilled water. DPDPE is injected into the left lateral cerebroventricle. The animals are lightly anesthetized with ether and then each mouse receives a small incision in the scalp. By using a 10 $\mu$l microsyringe fitted with a 27-gauge needle, 5 $\mu$l of DPDPE or distilled water is delivered 2 mm lateral and caudal to bregma at a depth of 3 mm. The wound is closed with a stainless steel clip and subsequent icv injections are made through the same hole in the skull. A typical injection schedule has been previously described (Cowan and Murray, 1990; Mattia et al., 1991). Groups of mice are injected with either U50,488 (s.c), morphine (s.c.), DPDPE (icv) and distilled water (n-64, s.c. or n=32, icv) at 1 PM on day 1 at appropriate doses. Antinociception is assessed at 0, 10, 20, and 30 min using the latency to tail-flick with 50° C. warm water as the nociceptive stimulus and calculated as 100×(test latency—control latency)/(15 or 30—control latency). A cut-off point of 15 or 30 sec is typically chosen depending on the intial latencies. Control mice receiving the distilled water are also measured for tail-flick latency. Regression lines, A50 values and 95% confidence limits are determined from individual data points using procedure 8 in the computer program of Tallarida and Murray (1987). The mice are injected with agonist or distilled water according to an injection schedule and then re-run in the antinociceptive assay. Pharmacological tolerance is reflected by the rightward (and possibly downward) displacement of initial dose-response curves. Four hr after the last injection, each animal is decapitated and the whole brain dissected out over crushed ice and immediately stored at −80° C. For some animals, following decipitation, the brains are dissected and cerebral cortex, hippocampus, cerebellum, medulla, midbrain, hypothalamus and striatum, collected, immediately frozen at −80° C. and used for Northern analysis.

For studies on rats, male S.D. albino rats are housed five per cage with a 12 hr light/12 hr dark daily cycle. The rats receive s.c. injections of U50,488, morphine or distilled water. DPDPE (5 $\mu$l) is injected into rats previously implanted with PE10 cannula in the left lateral cerebral ventricle (Tortella et al., 1981). The rats are injected as previously described (Heyman et al., 1988; Cowan and Murray, 1990). Groups of rats are injected with U50,488 (s.c.), morphine (s.c.), DPDPE (icv) or distilled water (n=64 s.c. or n=32 ICV) at 1 PM on day 1. Antinociception is assessed at 0, 10, 20, and 30 min using the latency to hind-paw lick on the 50° C. hot plate as the nociceptive stimulus and calculated as 100×(test latency—control latency)/(30, 45, or 60—control latency). A cut-off point of 30, 45, or 60 sec is chosen depending on the initial latencies. Calculations, injection schedules and data analysis are the same as described for mice.

XIV. Assay Kits

In another aspect, the present invention contemplates diagnostic assay kits for detecting the presence of opioid receptor polypeptides in biological samples, where the kits comprise a first container containing a first antibody capable of immunoreacting with opioid receptor polypeptides, with the first antibody present in an amount sufficient to perform at least one assay. Preferably, the assay kits of the invention further comprise a second container containing a second antibody that immunoreacts with the first antibody. More preferably, the antibodies used in the assay kits of the present invention are monoclonal antibodies. Even more preferably, the first antibody is affixed to a solid support. More preferably still, the first and second antibodies comprise an indicator, and, preferably, the indicator is a radioactive label or an enzyme.

The present invention also contemplates a diagnostic kit for screening agents. Such a kit can contain an opioid receptor of the present invention. The kit can contain reagents for detecting an interaction between an agent and a receptor of the present invention. The provided reagent can be radiolabelled. The kit can contain a known radiolabelled agent capable of binding or interacting with a receptor of the present invention.

It is further contemplated that the kit can contain a secondary polypeptide. The secondary polypeptide can be a G-protein. The secondary polypeptide can also be an effector protein. When a secondary polypeptide is included in a kit, reagents for detecting an interaction between the receptor and the secondary polypeptide can be provided. As a specific example, an antibody capable of detecting a receptor/G-protein complex can be provided. As another specific example, an antibody capable of detecting a G-protein/effector complex can be provided. Reagents for the detection of the effector can be provided. For example, if the effector provided is adenylyl cyclase, reagents for detecting the activity of adenylyl cyclase can be provided. The identity of such agents is within the knowledge of those skilled in the relevant art.

In an alternative aspect, the present invention provides diagnostic assay kits for detecting the presence, in biological samples, of polynucleotide that encode opioid receptor polypeptides, the kits comprising a first container that contains a second polynucleotide identical or complementary to a segment of at least 10 contiguous nucleotide bases of SEQ ID NO:1 or SEQ ID NO:3 or SEQ ID NO:11.

In another embodiment, the present invention contemplates diagnostic assay kits for detecting the presence, in a biological sample, of antibodies immunoreactive with opioid receptor polypeptides, the kits comprising a first container containing an opioid receptor polypeptide that immunoreacts with the antibodies, with the polypeptides present in an amount sufficient to perform at least one assay. The reagents of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media or a microscope slide. When the reagent provided is a dry powder, the powder can be reconstituted by the addition of a suitable solvent. The solvent can be provided.

EXAMPLES

Examples have been included to illustrate preferred modes of the invention. Certain aspects of the following examples are described in terms of techniques and procedures found or contemplated by the present inventors to work well in the practice of the invention. These examples are exemplified through the use of standard laboratory practices of the inventor. In light of the present disclosure and the general level of skill in the art, those of skill will appreciate that the following examples are intended to be exemplary only and that numerous changes, modifications and alterations can be employed without departing from the spirit and scope of the invention.

Example 1
Isolation of cDNA Clones

Two degenerate oligonucleotides,
SSTR-D1, 5'-ACCAA(T/C)(G/A)TCTA(T/C)AT(T/C)AT(T/C)CTIAACCTGGC-3' SEQ ID NO:9; and
SSTR-D2, 5'-ACIGTCAG(G/A)CAG(A/T)A(G/T)AT(G/A)CTGGTGAA-3' SEQ ID NO:10
were selected using conserved sequences present in the second and third transmembrane domains of the somatostatin (SRIF) receptor subtypes, SSTR1, SSTR2 and SSTR3 (Yasuda, et al. 1992; Yamada, et al. 1992). Amplification using the polymerase chain reaction (PCR™) was carried using an aliquot ($\approx 1\times10^6$ pfu) of a mouse brain cDNA library (Clontech, Palo Alto, Calif.; catalogue no. ML1036a) as a template.

The cycle conditions were: 10 cycles of denaturation at 94° C. for 1 min, annealing at 37° C. for 1 min and extension at 72° C. for 2 min, followed by 35 cycles of denaturation at 94° C. for 1 min, annealing at 55° C. for 1 min and extension at 72° C. for 2 min. The PCR™ products were separated on a 3% low melting temperature agarose gel, and DNA fragments between 150 and 200 bp were isolated, cloned into M13 mp18 and sequenced.

Two PCR™ products encoding novel SRIF receptor-like sequences were identified, termed msl-1 (SD3) and msl-2 (SD15). These were $^{32}$P-labeled by nick translation and used to screen the mouse brain cDNA library by hybridization using standard conditions with a final post-hybridization wash in 0.1×SSC and 0.1% SDS at 50° C. before exposure to X-ray film.

Mouse brain cDNAs encoding SRIF receptor-related sequences were amplified using PCR™ and degenerate oligonucleotide primers as set forth above. PCR™ products of 150–200 bp were cloned and sequenced. Of the 33 clones characterized, two encoded mSSTR1, two SSTR2, nine mSSTR3, four were identical and encoded a new member of the G protein-coupled receptor superfamily designated msl-1, and one encoded a second new receptor-like sequence termed msl-2. The sequences of the remaining 15 clones were unrelated to those of G protein-coupled receptors or of any other sequences in the GenBank data base. The clones msl-1 and msl-2 were used as probes to screen a mouse brain cDNA library and to isolate λmsl-1 and λmsl-2 having inserts of 3.1 and 2.3 kb, respectively.

The sequences of the inserts in λmsl-1 and λmsl-2 (deposited in the GenBank database with accession numbers L11065 and L11064, respectively) were determined and shown to encode polypeptides of 380 and 372 amino acids, respectively (FIG. 1) the sequences are SEQ ID NO:2 and SEQ ID NO:4 respectively. The sequences of msl-1 and msl-2 were most closely related to those of members of the recently described SRIF receptor family with ~35% identity with the sequence of mSSTR1.

The sequences of msl-1 and msl-2 share many features conserved among members of the G polypeptide receptor superfamily including the sequence Asp-Arg-Tyr (DRY) in the NH$_2$-terminal end of the second intracellular loop and cysteine residues in the first and second extracellular loops that can form a disulfide bond. There are also potential sites for N-linked glycosylation in the putative NH2-terminal domain and several potential phosphorylation sites for cAMP-dependent protein kinase and protein kinase C (Kennelly & Krebs, 1991) in intracellular loops and in the COOH-terminal domain (See FIG. 1).

Alignment of the amino acid sequences of msl-1 and msl-2 showed that they have 61% amino acid identity and 71% similarity. As noted previously in other comparisons of closely-related G protein-coupled receptors (Probst, et al., 1992), the sequences of the putative membrane-spanning segments are more highly conserved than those of the NH$_2$— and COOH-terminal domains. It is notable that the sequences of the intracellular loops, including the short third intracellular loop which is believed to be critical for G protein coupling (Kobilka, et al., 1988), are highly conserved between msl-1 and msl-2, suggesting that they can couple to the same G proteins. Both msl-1 and msl-2 have a conserved Asp residue in the second transmembrane domain. This Asp has been proposed to mediate sodium inhibition of agonist binding in the adrenergic (Horstman, et al., 1990) and somatostatin receptors.

Example 2
Expression and Binding Results

A 1.2 kb Pst I fragment of the mouse kappa opioid receptor cDNA clone, λmsl-1, and 1.3 kb EcoRI-SacI fragment of the delta opioid receptor cDNA clone λmsl-2, were cloned into the CMV promoter-based expression vectors pCMV-6b and pCMV-6c (obtained from Dr. Barbara Chapman, Chiron Corp., Emeryville, Calif.), respectively. The resulting constructs, pCMV-msl-1 and pCMV-msl-2, were used to transfect COS-1 cells as described previously (Yasuda, et al. 1992).

Binding studies using membranes prepared from COS-1 cells transiently expressing msl-1 and msl-2 were carried out 72 h post-transfection. Briefly, cells were harvested in 50 mM Tris-HCl (pH 7.8), 1 mM ethylene glycol bis(β-aminoethyl ether)-N,N'-tetraacetic acid, 5 mM MgCl$_2$, 10 μg/ml leupeptin, 10 μg/ml pepstatin, 200 μg/ml bacitracin, and 0.5 μg/ml aprotinin (Buffer 1) using a Polytron (Brinkmann, setting 2.5, 30 sec). The homogenate was then centrifuged at 48,000×g for 20 min at 4° C. The pellet was re-suspended in Buffer 1 and this membrane preparation was used for radioligand binding studies.

Cell membranes (20–30 μg total protein) were incubated with [$^3$H]U69,593 (1 nM, specific activity 37.2 Ci/mmol) or [$^3$H]dextromethorphan (1 nM, specific activity 82.7 Ci/mmol), [$^3$H]DTG (1 mM, specific activity 37.2 Ci/mmol) or [$^3$H]DAMGO (1 nM, specific activity 55 Ci/mmol) (Dupont NEN, Boston, Mass.) in a final volume of 200 μl for 40 min at 25° C. in the presence or absence of competing agents. Nonspecific binding was defined as the radioactivity remaining bound in the presence of 10 μM naloxone for all radioligands except [3H]dextromethorphan and [$^3$H]DTG for which 10 μM haloperidol or carbetapentane citrate were used.

The binding reaction was terminated by the addition of ice-cold 50 mM Tris-HCl (pH 7.8) and rapid filtration over Whatman GF/B glass fiber filters that were pre-treated with 0.5% polyethylimine and 0.1% bovine serum albumin for at least 1 h. The filters were then washed with 12 ml of ice-cold 50 mM Tris-HCl (pH 7.8) and the bound radioactivity determined using a liquid scintillation counter. Data from radioligand binding studies were used to generate inhibition curves. IC$_{50}$ values were obtained by curve-fitting performed by the mathematical modeling program FITCOMP available on the NIH-sponsored PROPHET system.

The homology between msl-1 and msl-2 and the SRIF receptors suggested that they might be new members of the SRIF receptor family. However, membranes from COS-1 cells transiently expressing msl-1 and msl-2 did not show specific [$^{125}$I-Tyr$^{11}$] SRIF binding demonstrating that msl-1 and msl-2 were not SRIF receptors. Since the SRIF agonist SMS 201–995 has been reported to bind to SRIF and mu opioid receptors, we considered that msl-1 and msl-2 might be opioid receptors. While studies were in progress to test this hypothesis, two groups reported the cloning of a mouse delta-opioid receptor from NG 108–15 cells. The sequence of their receptor was identical to msl-2.

Binding studies using agonists selective for delta, kappa, mu and sigma opioid receptors confirmed that msl-2 was a delta opioid receptor and showed that msl-1 was a kappa receptor. The binding properties of membranes prepared from COS-1 cells expressing msl-1 and msl-2 are summarized in Table 2.

TABLE 2

BINDING POTENCY OF OPIOID LIGLANDS FOR CLONED MOUSE OPIOID RECEPTORS EXPRESSED IN COS-1 CELLS

| | IC$_{50}$(nM) | |
|---|---|---|
| | [$^3$H]U-69, 693 msl-1 (ORK1) | [$^3$H]Naltrindole msl-2 (ORD1) |
| Endogenous opioid ligands | | |
| Dynorphin A (1–17) | 0.4 | >100 |
| Dynorphin A (1–8) | 0.2 | >100 |
| Dynorphin B | 0.1 | >100 |
| α-Neoendorphin | 0.1 | 10 |
| β-Endorphin (human) | 42 | 15.3 |
| Leu-enkephalin | >1000 | 79 |

TABLE 2-continued

BINDING POTENCY OF OPIOID LIGLANDS FOR CLONED MOUSE OPIOID RECEPTORS EXPRESSED IN COS-1 CELLS

| | IC$_{50}$(nM) | |
|---|---|---|
| | [$^3$H]U-69, 693 msl-1 (ORK1) | [$^3$H]Naltrindole msl-2 (ORD1) |
| Met-enkephalin | >1000 | 41 |
| Kappa-selective liglands | | |
| Dynorphin (1–17)NH$_2$ | 0.2 | >100 |
| (D-Ala$^2$,F$_5$Phe$^4$]Dynorhpin(1–17)NH$_2$ | 0.2 | >100 |
| Bremazocine | 0.3 | 19 |
| [Met$^5$]Dynorphin (1–17) | 0.6 | >100 |
| U-62, 066 | 1.0 | >1000 |
| Ethylketocyclazocine | 1.1 | 611 |
| U-50, 488 | 1.1 | >1000 |
| nor-BNI | 1.2 | 197 |
| U-69, 593 | 2.6 | >1000 |
| ICI 204, 448 | 6.6 | >1000 |
| [D-Ala$^2$, F$_5$Phe$^4$]Dynorphin (1–13)NH$_2$ | 19 | >100 |
| Nalbuphine | 36 | >1000 |
| Dynorphin (7–17) | >1000 | >1000 |
| Delta-selective ligands | | |
| Naltridole | 37 | 1.9 |
| DADL | >1000 | 20 |
| DSLET | >1000 | 21 |
| DPDPE | >1000 | 122 |
| Other | | |
| Naltrexone | 0.66 | 368 |
| (−)-Naloxone | 4.9 | 565 |
| (+)-Naloxone | >1000 | >1000 |
| Levorphanol | 5.3 | 103 |
| Dextrorphan | >1000 | >1000 |
| DAMGO | >1000 | >1000 |
| Haloperidol | >1000 | >1000 |
| DTG | >1000 | >1000 |
| Dextromethorphan | >1000 | >1000 |
| Carbetapentane citrate | >1000 | >1000 |
| SRIF | >1000 | >1000 |
| SMS 201–995 | >1000 | >1000 |

That msl-1 is a kappa type receptor is indicated by the high affinity of the receptor for U-50,488 and U-69,593 which bind potently and specifically to kappa, receptors but not to any other receptor (Zukin, et al., 1988; Clark, et al., 1989). Also consistent with msl-1 being a kappa receptor is its high affinity for dynorphin A and its much lower affinity for β-endorphin and the enkephalins. Furthermore, msl-1 exhibited very low affinity for mu, delta or sigma specific ligands. Agonist and antagonist binding to msl-1 was stereospecific, as expected for an opioid receptor.

Both msl-1 and msl-2 are coupled to G proteins since GppNHp (100 μM) decreased agonist binding to msl-1 by 44% and to msl-2 by 20%. Moreover, 90 mM NaCl decreased agonist binding to msl-1 and msl-2 by 95% and 60%, respectively, confirming the sodium dependence of opioid agonist binding noted using membranes prepared from brain (Pert & Snyder, 1974; Ott, et al., 1988).

Inhibition of forskolin-stimulated cyclic AMP accumulation was observed in COS-1 cells transiently expressing msl-1 and msl-2 for 72 h. Briefly, cells cultured in 12 well Costar tissue culture plates were incubated with 1 ml of DMEM medium containing 10% fetal bovine serum and 500 nM 3-isobutyl-1-methylxanthine for 30 min. The medium was removed, the cells were washed and replaced with similar medium containing 10 μM forskolin alone or with 1 μM opioid agonists and/or antagonists. After 30 min, the medium was removed and 0.5 ml of 1 N HCl added to the cells which were then sonicated for 10 sec. The HCl was removed by evaporation in a SpeedVac and the c-AMP content of the samples determined using a radioimmunoassay kit (NEN/Dupont).

Figure 2B:
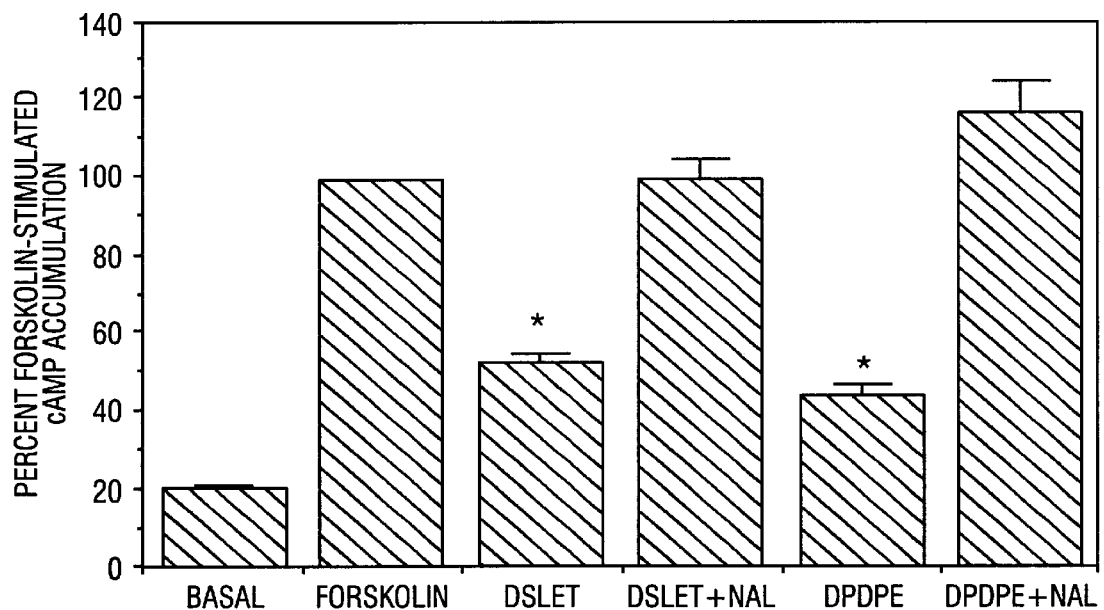

The two opioid receptors mediate opioid inhibition of adenylyl cyclase activity. The kappa-specific agonists U-50, 448 and ethylketocyclazocine inhibited forkolin-stimulated cAMP accumulation in COS-1 cells transiently expressing msl-1 by 50% and this effect was completely reversed by naloxone (See FIG. 2A and FIG. 2B). The delta-specific agonists DPDPE and DSLET inhibited forskolin-stimulated cAMP formation in COS-1 cells expressing msl-2 by 70% and this effect could also be blocked by naloxone. These results show that both msl-1 and msl-2 are able to mediate subtype-specific agonist induced inhibition of adenylyl cyclase activity in COS-1 cells.

Example 3

Tissue Distribution of Kappa Opioid Receptor (msl-1) mRNA

For Northern blot analysis, a mouse multiple tissue Northern blot (Clontech) was hybridized with a $^{32}$P-labeled 376 bp Pst I-EcoRI fragment of λmsl-1, corresponding to nucleotides 172–548, according to the manufacturer's recommendations. After hybridization, the blot was washed at room temperature in 2×SSC and 0.05% SDS at room temperature and then at 48° C. in 0.1×SSC and 0.1% SDS for 30 min. The blot was exposed to X-ray in the presence of an intensifying screen at −75° C. for 7 days. For Southern blot analysis, 10 μg of mouse and human DNA was digested with EcoRI, separated on a 1% agarose gel, and transferred to a nitrocellulose filter. The blot was hybridized with a $^{32}$P-labeled 1.2 kb Pst I fragment of λmsl-1, nucleotides 172–1408 using standard conditions. The blot was washed at 48° C. in 0.1×SSC and 0.1% SDS for 30 min before exposure to X-ray film for 6 days.

In situ hybridization using brain sections prepared from adult male BALB/c mice was carried out as described previously (Breder, et al., 1992) using $^{35}$S-labeled antisense and sense riboprobes transcribed from a plasmid containing the 376 bp Pst-I-EcoRI fragment of λmsl-1 described above. After hybridization and washing, the sections were dipped in NTB2 photographic emulsion and exposed for 4 weeks. Slides were developed with D-19 developer and then counterstained for 3 min in thionin before viewing using dark-field microscopy.

RNA blotting showed a single transcript of 5 kb encoding the kappa opioid receptor msl-1 mRNA in adult mouse brain. No hybridization signal was seen in heart, spleen, liver, lung, skeletal muscle, kidney or testes. The distribution of kappa opioid receptor mRNA in the central nervous system of the adult mouse was studied by in situ hybridization. There are high levels of expression in the neocortex, piriform cortex, hippocampus, amygdala, medial habenula, hypothalamus (arcuate and paraventricular nuclei), locus ceruleus and parabrachial nucleus.

The hybridization of $^{32}$P-labeled msl-1 cDNA to EcoRI-digested mouse and human DNAs showed intense labeling of two mouse DNA fragments of 18 and 3.4 kb whereas this probe hybridized to multiple fragments of human DNA: strongly to fragments of 8.0, 6.0 and 2.5 kb, and faintly to fragments of 9.5, 5.1, 4.8 and 3.1 kb. The molecular basis for the multiple bands seen in these blots needs to be established. The presence of an internal Eco RI site in the msl-1 cDNA sequence can account for hybridization to two mouse fragments. Moreover, this result suggests that there can only be a single kappa receptor gene in the mouse genome.

The hybridization to multiple DNA fragments in the human blot is more difficult to interpret. The partial sequence of the human kappa opioid receptor gene indicates that there are at least two introns in this gene located in codons corresponding to amino acids Arg$^{86}$ and Asp$^{184}$ of the mouse sequence and this result can explain, at least in part, the multiple bands seen in the Southern blot of human DNA.

Recent reports (Xie, et al., 1992) disclose the expression cloning of a putative opioid receptor cDNA from human placenta, a rich source of kappa receptors. Cells expressing this cloned receptor bound opioid ligands with only moderate affinity, although in a stereospecific manner, but did not show the expected kappa receptor selectivity. The sequence of this clone also showed greater sequence identity with the human neuromedin K receptor than to the cloned mouse delta or kappa opioid receptors further confounding its relationship with these latter receptors which exhibit affinity and selectivity expected for bona-fide opioid receptors.

The recent cloning of a delta opioid receptor and our studies here describing the cloning of a kappa-type opioid receptor strongly suggest that the different opioid receptor classes represent distinct gene products. However, the molecular basis for the different subtypes within some classes, e.g., kappa$_1$, kappa$_2$ and kappa$_3$, remains to be determined. The pharmacological characterization of msl-1 as expressed in COS-1 cells suggests that it is a kappa1 receptor. The other kappa subtypes could be the products of other genes or arise by differential glycosylation or other post-translational modification of a common polypeptide or represent G protein coupled and uncoupled states an identical molecule (Frielle, et al., 1988). Alternatively, if there are introns in the kappa opioid receptor gene as our preliminary analysis of the human gene indicates, then perhaps alternative splicing could generate kappa subtypes with slightly different pharmacological properties.

The comparison of the amino acid sequences of the mouse delta and kappa opioid receptors showed the sequences of the putative membrane spanning segments and connecting loops were more highly conserved than the NH—$_2$ and COOH-termini. The sequence conservation included the third intracellular loop. This is the region where other G protein-coupled receptors bind to G proteins which suggests that perhaps these two receptors interact with similar G proteins. The availability of these two cloned receptors with very distinct pharmacological properties will permit the localization of the ligand binding site(s) by comparing the binding properties of chimeric polypeptides as has been done for the adrenergic (Frielle, et al. 1988) and tachykinin receptors (Yokota, et al. 1992).

The different classes of opioid receptors are believed to subserve different physiological functions (Olson, et al., 1989; Simon 1991; Lutz & Pfister 1992). The distribution of kappa opioid receptor mRNA in the mouse brain suggests that the kappa receptor can be involved in the regulation of arousal, neuroendocrine and autonomic functions, as well as processing of sensory information. Preliminary RNA blotting studies suggest that there can be differences in the distribution of kappa opioid receptor mRNA among species. For example, in the in situ hybridization show high levels of mRNA in the cortex and very low levels in the striatum, whereas Northern blotting studies using RNA prepared from different regions of the rat brain suggest that mRNA levels are higher in the striatum than in the cerebral cortex, a result consistent with ligand binding studies in rat brain (Mansour, et al., 1987, Nock, et al, 1988, Unterwald, et al., 1991). The functional consequences of such differences are unknown but imply that results of studies using kappa selective agonists in one species cannot be extrapolated to other species. Indeed, of the three opioid receptor classes, the kappa type shows the most divergent distribution among species. Preliminary in situ hybridization studies show that delta opioid receptor mRNA has a similar but distinct distribution compared with that of the kappa receptor in the mouse brain including expression in the cerebral cortex, hippocampus, amygdala and hypothalamus.

The availability of the cloned opioid receptors will permit direct studies of their functions in vivo. They will also greatly facilitate the development of more selective agonists and antagonists for clinical applications. This will be particularly important in the future for kappa receptors since agonists for this class of opioid receptor induce analgesia but have limited abuse potential (Unterwald, et al. 1987) and fewer side effects on respiratory function (Shook, et al. 1990). Similarly, identification of other members of the kappa opioid receptor family can lead to the development of selective ligands that induce analgesia but have few of the sedative or psychomimetic side-effects of kappa agonists (Pfeiffer, et al. 1986) or instead selectively antagonize these unfavorable side-effects.

Example 4
Diagnostic/Therapeutic Applications

Given the isolation and purification of distinct opioid receptor polypeptides, it is possible to utilize these polypeptides in methods designed to screen candidate substances such as candidate agonists and antagonists with potentially preferential properties for use in diagnostic and therapeutic applications.

For instance, as noted recently by (Dohlman, et al. 1991) with the growing number of receptor sub-types, G proteins, and effectors, characterization of ligand binding and G protein recognition properties of receptors is an important challenge for the diagnostic and therapeutic industries. As noted therein, reconstitution experiments were the first to show that receptors can, with varying degrees of specificity, couple to multiple (and in some cases functionally distinct) G proteins (Kanaho, et al. 1984)

For instance, cloning and over-production of the muscarinic and $\alpha_2$-adrenergic receptors led to the demonstration that a single receptor sub-type, when expressed at high levels in the cell, will couple to more than one type of G protein. For each of these receptors, agonist treatment led to both inhibition of adenylyl cyclase and stimulation of phosphoinositide metabolism. Finally, individual G protein species have been shown to stimulate more than one effector, $G_s$, for example, has been reported to regulate calcium channels, in addition to adenylyl cyclase. These authors note that given this complexity and apparent degeneracy of function, a question of fundamental importance is how, and under what circumstances, can G proteins organize signals from multiple receptors and direct them to the appropriate effectors?

The traditional approach has been to reconstitute the purified receptor and G protein components in vitro. Unfortunately, as noted by these authors, purification schemes have been successful for only a very limited number of receptor sub-types and there cognate G-proteins. Alternatively, and as here enabled by the cloning and sequencing of the opioid receptors identified thus far, heterologous expression systems can be of more general usefulness in the characterization of cloned receptors and in elucidating receptor-G protein coupling specificity.

One such system has been recently developed in yeast cells, in which genes for a mammalian $\beta_2$-adrenergic and $G_s$ α-subunit were coexpressed (King, et al. 1990). Expression of the $\beta_2$-adrenergic to levels several hundred-fold higher than any human tissue was attained, and ligand binding was shown to be of the appropriate affinity, specificity, and stereoselectivity. Moreover, a $\beta_2$-adrenergic-mediated activation of the pheromone signal transduction pathway was demonstrated by several criteria, including altered growth rates, morphological changes, and induction of a pheromone-responsive promoter (FUS 1) fused to the *Escherichia coli* lacZ gene (encoding β-galactosidase).

The ability to control the yeast pheromone response pathway by expression of the $\beta_2$-adrenergic and $G_s$ α has the potential to greatly facilitate structural and functional characterization of such receptors. By scoring for growth rates or β-galactosidase induction, the properties of mutant receptors can be tested rapidly. In addition, isolated recombinant opioid receptors as enabled herein should be capable of discriminating candidate substances with the desirable properties of opioids, which however lack the undesirable properties of opioids. Furthermore, it should be possible using systems such as that described above to identify candidate substances having selective ability to interact with one or more of the opioid receptor polypeptides enabled by the present application over others in the same family of opioid receptors.

Thus, for instance, it will be possible to utilize a battery of opioid receptors cloned and expressed in a particular common cell line and to expose such a battery of receptor polypeptides to a variety of candidate substances. The results of such a screening assay should be capable of identifying a candidate substance capable of, for instance, interacting with a delta, kappa, mu or sigma opioid receptor.

Furthermore, it should be possible then to investigate the structure-activity relationships of opioids when compared to the isolated recombinant opioid receptors enabled by the present application. Such studies would include not only binding studies to identify candidate substances such as agonists and antagonists which will bind each individual opioid receptor, but will also include studies to identify those candidate substances which stimulate an activity in the opioid receptor apart from the binding of the same to the receptor.

Moreover, as noted by Dohlman, et al. 1991, as additional genes for the putative G-protein, coupled receptors, such as those enabled by the present application, are isolated, a series of ligands can be conveniently screened to identify those with activity toward the unidentified gene product. As noted by these authors as well, expression of a single receptor in the absence of other related sub-types is often impossible to achieve in native mammalian cells. Thus, expression in a microorganism, or in an isolated eukaryotic cell that has no such endogenous receptors can be useful for screening and evaluating sub-type-selective drugs (Marullo, et al. 1988; Payette, et al. 1990, and King, et al. 1990).

Example 5
Human Opioid Receptors

Human opioid receptor polypeptides are isolated and identified from human gene sequences that encode such receptor polypeptides. A partial genomic sequence containing both introns and exons of a human kappa opioid receptor is shown in FIG. 3. FIG. 4A and FIG. 4B compare the partial amino acid sequences of human kappa opioid receptor with the mouse kappa opioid receptor. The mouse sequence begins with amino acid residue 1 and the human sequence begins with amino acid residue 87.

A cDNA library was constructed from the hippocampus of a human brain and screened with a polynucleotide probe from the mouse kappa opioid receptor. Briefly, cDNA molecules were ligated with EcoRI linkers. The vector λgt10 was digested with EcoRI to create linear vector. The cDNA molecules with the EcoRI linkers were ligated into the linear vector. The host cell for library construction was *E. coli* strain LE392.

The amino acid sequences of the human and mouse kappa opioid receptors are highly homologous. As can be seen in FIG. 4a and 4b (SEQ ID NO:12) of the 295 amino acids, 292 are identical or similar. 281 residues are identical and 6 residues involve conservative substitutions. Residues 232, 284, 285, 328, and 348 are substitutions which involve leucine, isoleucine or valine. As is appreciated by skilled artisans, substitutions involving leucine, isoleucine and valine are conservative substitutions. Residue 218 is a change from glutamic acid to aspartic acid, and residue 274 is a change from lysine to arginine. As is well known in the art, the hydropathic index of glutamic acid and aspartic acid are identical at −3.5. Furthermore, lysine and arginine are the two least hydropathic amino acids with an index of −3.9 and −4.5, respectively. Thus the amino acid changes at positions 218 and 274 are conservative substitutions. In addition there are 4 amino acids in the human kappa opioid receptor at positions, 255, 267, 351, and 355 which have not yet been identified because the complete nucleotide sequences have not yet been ascertained. However, it is noted that there is only one nucleotide missing from the sequences that encode for residues 351 and 355. It is likely that when these two nucleotides are identified, amino acid residues 351 and 355 will be homologous. Residues 255 and 267 are not presently identified because two nucleotides that encode for the residues are missing from the nucleotide sequence. The only significant difference between the human and mouse kappa opioid receptor is found in residue 358 in which a serine is replace by an asparagine.

The human kappa opioid receptor shown in FIG. 4A and 4B (SEQ ID NO:2) is a partial sequence in which the amino terminus of the human kappa opioid receptor is not presented. The gene sequence encoding the amino terminus of the human kappa opioid receptor is to be identified by screening a genomic or a cDNA library with a polynucleotide o f the human or mouse kappa opioid receptor. Preferably a polynucleotide of the human kappa opioid receptor of FIG. 3 is the probe. Human opioid receptor subtypes are identified by screening with a human opioid receptor probe.

Further, human cDNA that encodes an opioid receptor polypeptide is transfected into a suitable host cells using techniques set forth hereinbefore and the opioid receptor polypeptide is expressed. The expressed human polypeptide is screened using agonists and antagonists to identify the opioid receptor subtype.

Example 6
Stable Transfection of Mammalian Cells
A. Isolation of Stable Transformants PC-12 cells were grown in RPMI medium with 10% horse serum and 5% bovine serum in 5% $CO_2$ at 37° C. to 50% confluency. The cells were transfected by the lipofection method (Muller et al., 1990) with 7 μg of the 1.2-kilobase Pst I fragment of the mouse κ receptor cDNA cloned into the CMV promoter-based expression vector pCMV-6c as previously described (Yasuda et al., 1993). The cells were selected and maintained in a similar medium containing 200 μg/ml G418. The generation of the CHO-DC44 cell line stably expressing the mouse δ receptor was accomplished as previously described (Rens-Domiano et al., 1992). Briefly, a 1.3-kilobase EcoI-SacI fragment of the mouse δ opioid receptor cDNA was inserted into the expression vector pCMV-6c and contransfected with pSV2noo into CHO cells and stable transfectants were selected and grown as previously described (Yasuda et al., 1993 and Rens-Domiiano et al., 1992). The rat μ receptor was expressed transiently in COS-7 cells, as previously described (Chen et al., 1993 and Kong et al., 1993).

B. Pharmacological Properties

Receptor binding assays were performed using membranes from either PC12 cells stably expressing the cloned mouse κ receptor, CHO-DG44 cells stably expressing the mouse δ receptor, or COS-7 cells transiently expressing the rat μ receptor 48–72 hours after transfection as previously described (4,10). For radioligand binding assays, cells were harvested in 50 mM Tris-HCI (pH 7.8) containing 1 mM ethylene glycol bis(β-aminoethyl ether)-N,N'-tetraacctic acid, 5 mM $MgCl_2$, 10 μg/ml leupeptin, 10 μg/ml pepstatin 200 μg/ml bacitracin and 0.5 μg/ml aprolinin (buffer 1) and centrifuged at 24,000×g for 7 min at 4° C. The pellet was homogenized in buffer 1 using a Polytron (Brinkmann, setting 2.5 30 sec). The Homogenate was then centrifuged at 48,000×g for 20 min at 4° C. The pellet was homogenized in buffer I and this membrane preparation was used for the radioligand binding studies. For inhibition studies, cell membranes (10–20 μg protein) were incubated with [$^3$H]U-69,593 (2 nM, specific activity 47.4 Ci/mmol), [$^3$H] naltrindote (1 nM, specific activity 31.2 Ci/mmol), or [$^3$H] DAMGO (1 nM, specific activity 55 Ci/mmol) (NEN/Dupont, Wilmington, Del.) in a final volume of 200 μL for 40 min at 25° C. in the presence or absence of competing agents. For saturation experiments, cell membranes were incubated with increasing concentrations of the radioligands. Nonspecific binding was defined as the radioactivity remaining bound in the presence of 10 μM naloxone for all radioligands. The binding reaction was terminated by the addition of ice-cold 50 mM Tris-HCl buffer (pH 7.8) and rapid filtration over Whatman GF/B glass fiber filters which were pretreated with 0.5% polyethyleneimine/0.1% BSA for at least 1 hour. The filters were then washed with 12 mL of ice-cold Tris-HCl buffer and the bound radioactivity counted in a scintillation counter. Data from radioligand binding studies were used to generate inhibition curves. $IC_{50}$ values were obtained from curve-fitting performed by the mathematical modeling program FITCOMP (Perry and McGonigle, 1988) and saturation data was analyzed using FITSAT (McGonigle et al., 1988) available on the National Institutes of Health-sponsored PROPHET system. The inhibitory binding constant ($K_i$) was calculated from the $IC_{50}$ values using the Chong-Prusoff equation (Cheng and Prusoff, 1973).

Figure 5A:
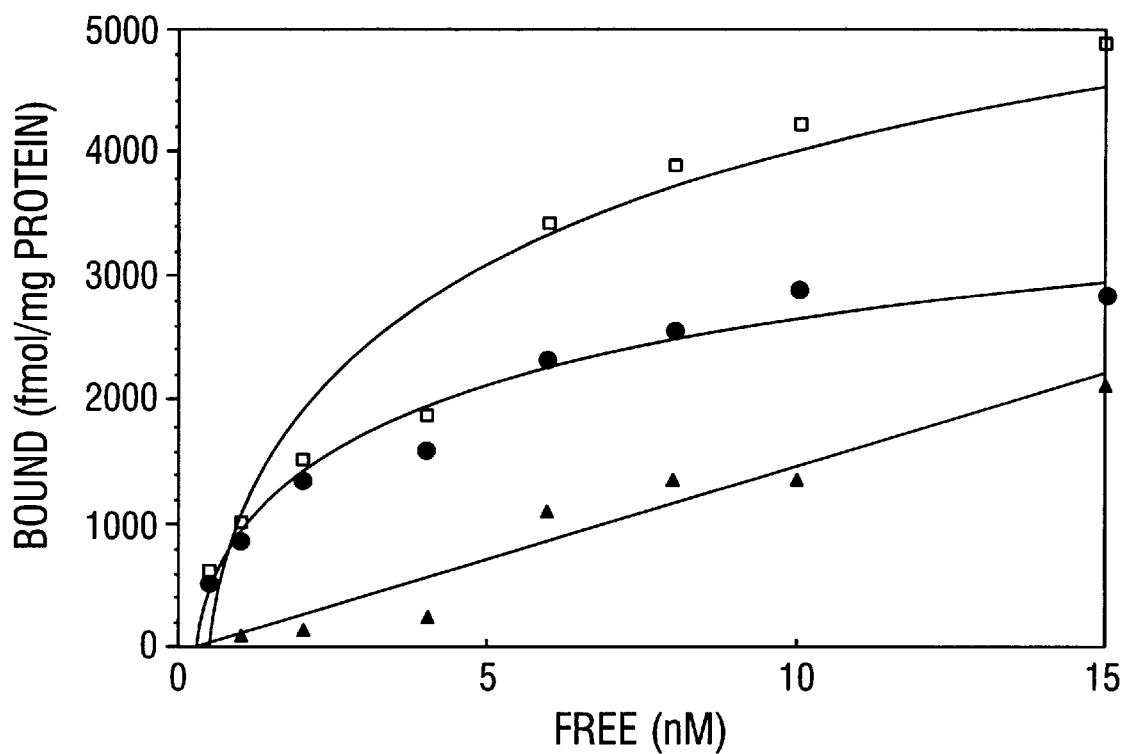
Figure 5B:
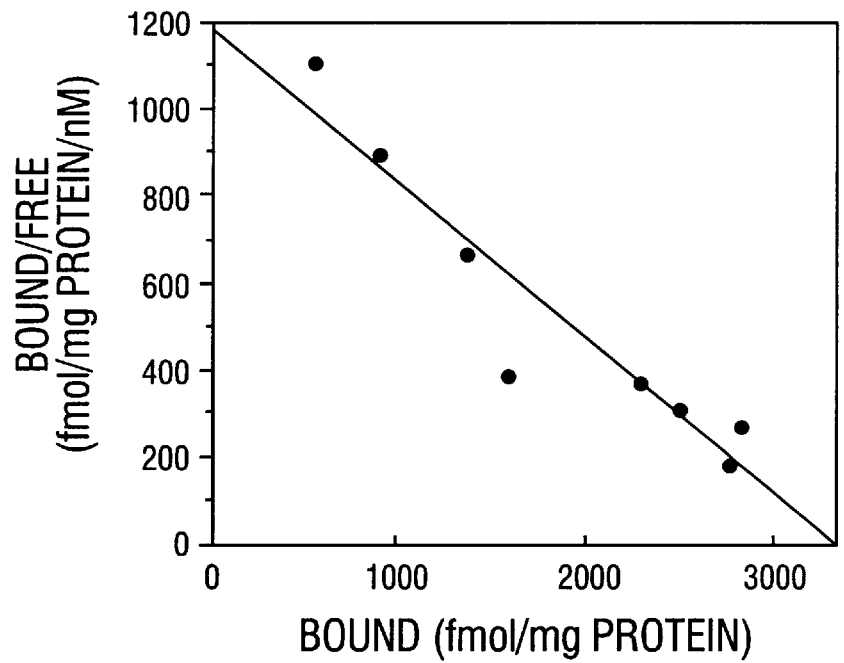
Figure 5C:
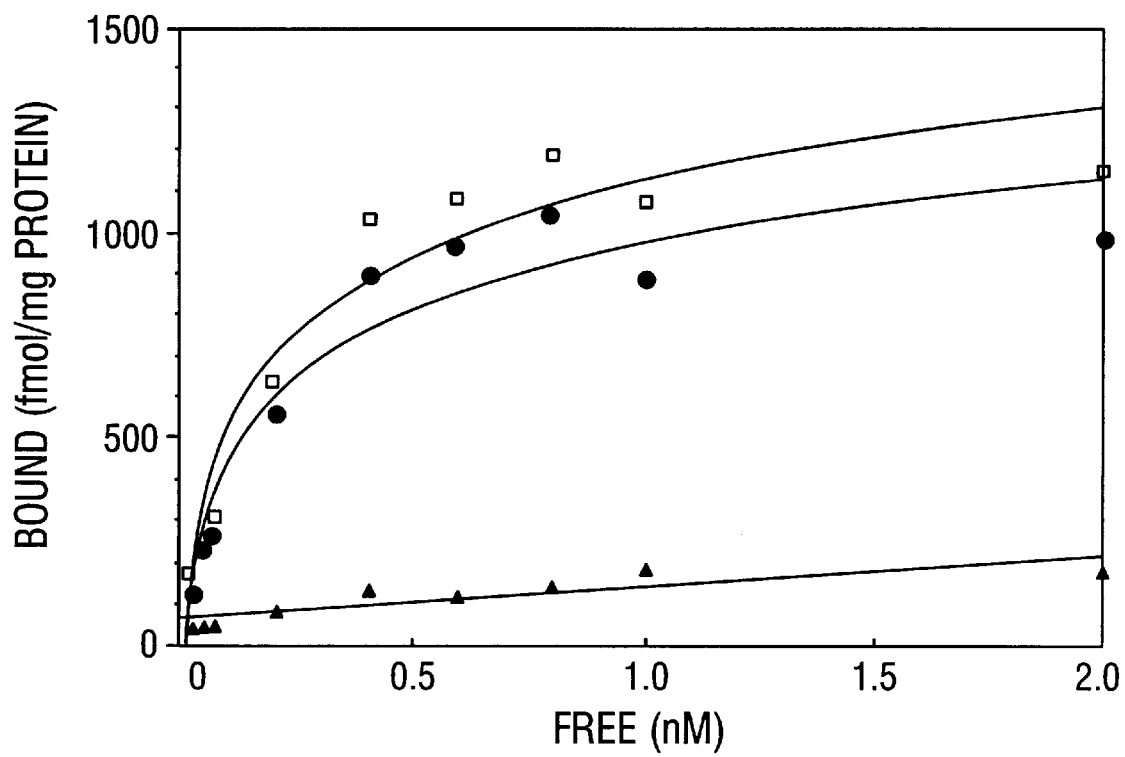
Figure 5D:
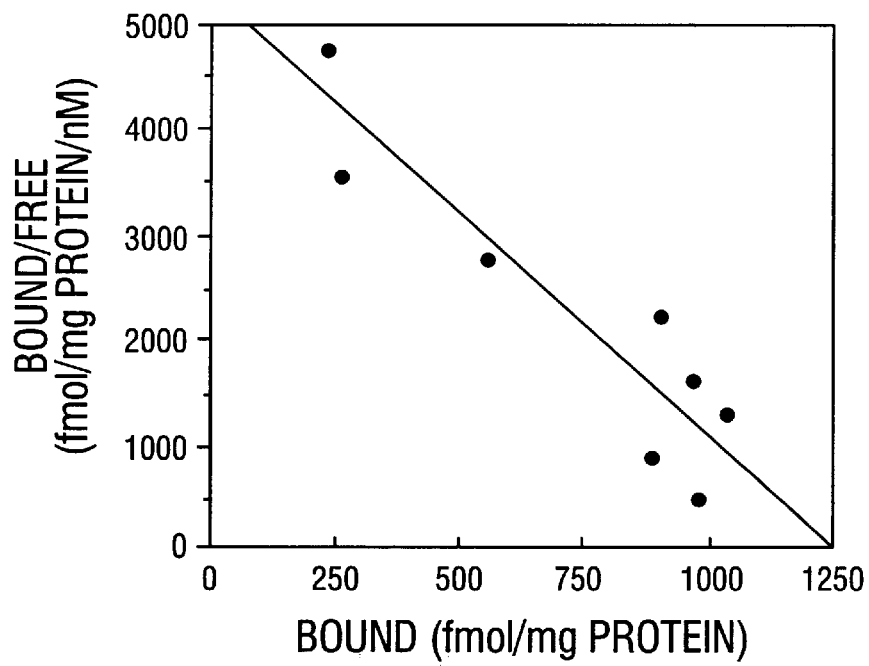
Figure 5E:
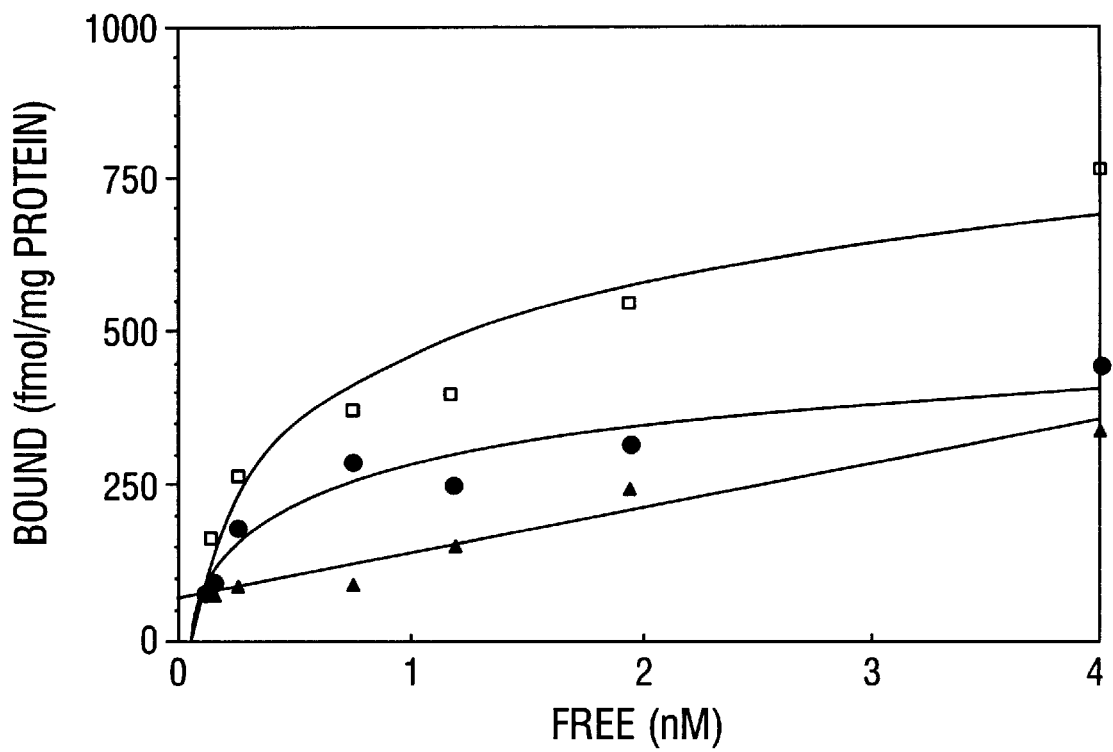
Figure 5F:
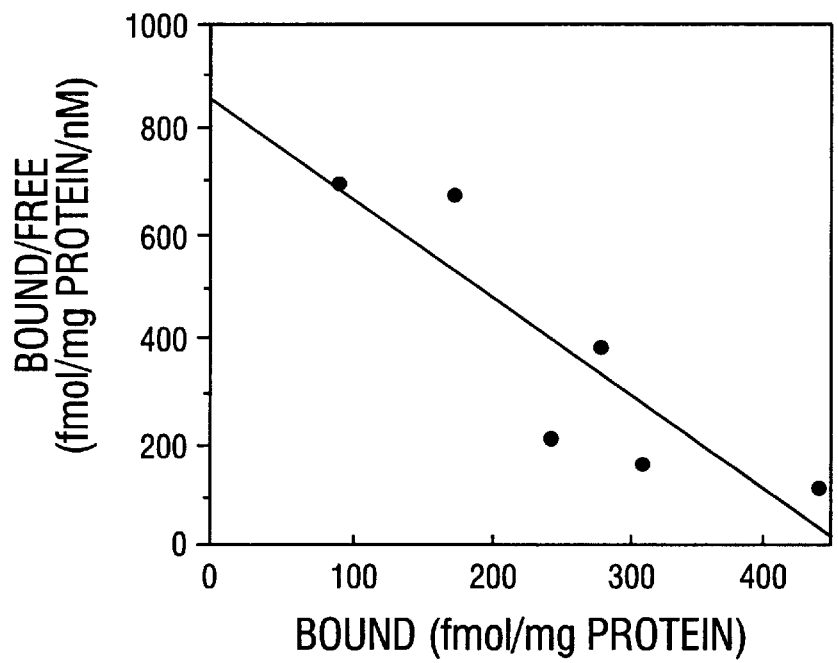

Cloned cDNAs encoding κ, δ, and μ receptors were expressed stably in PC12 (κ) or CHO-G44 cells (δ) or transiently in COS-7 cells (μ). The κ, δ, and μ opioid receptors were labelled with the selective opioid radioligands [$^3$H]U-69,593, [$^3$H]naltrindole, or [$^3$H]DAMGO, respectively. The binding of these radioligands is saturable and of high affinity (FIG. 5A and FIG. 5B). The saturation experiments demonstrated that [$^3$H]U-69,593 binds to the cloned κ receptor with a $K_D$ of 2.8 nM and a $B_{max}$ of 3346 fmol/mg protein. Similarly, [$^3$H]naltrindole binding to the cloned δ receptor is of high affinity and binds with a $K_D$ of 0.18 nM and a $B_{max}$ of 633 fmol/mg protein. The $K_D$ for [$^3$H]DAMGO binding to the cloned μ receptor is 0.57 nM and the $B_{max}$ is 444 fmol/mg protein. All data were best fit by a single-site analysis. No specific radioligand binding was detectable in appropriate nontransfected control cells.

A battery of opioid ligands were used to identify the pharmacological specificities of the cloned κ, δ, and μ opioid receptors (Table 3). These include both peptide and nonpeptide compounds previously characterized as selective and nonselective agents for opioid receptors (Lutz and Pfister, 1992; Goldstein and Naidu, 1989; Schiller, 1993; Portoghese, 1993; and Corbett et al., 1993). The endogenous opioid peptide dynorphin A is selective for the κ receptor, whereas β-endorphin, Leu- and Met-enkephalin are selective for the μ and δ receptors as they either did not bind to the κ receptor, as for Leu- and Mcl-enkephalin, or bound with low potency, as for β-endorphin. Des-Tyr$^1$-β-endorphin did not bind to any of the opioid receptors. The binding to each receptor is stereoselective, being inhibited by (−)nuloxone and levorphanol but not by their respective isomers (+)naloxone or dextrorphan. Other relatively non-selective compounds tested were (±)bremazocine, ethylketocyclzocine, etorphine, pentazocine, and diprenorphine. Each of these compounds is relatively non-selective for μ vs. κ and displayed higher affinities for these receptors than for the 5 receptor. Analogous results were found with β-FNA and β-CNA, although the values given are not true Ki's due to the covalent nature of these ligands. Furthermore, naltrexone, nalbuphine, and nalorphine were also relatively selective for κ, μ, only binding to the δ receptor at much higher concentrations.

TABLE 3

BINDING POTENCIES (K$_i$-nM) OF LIGANDS FOR THE CLONED κ, δ AND μ OPIOID RECEPTORS

|  | κ RECEPTOR [$^3$H]U-69,593 | δ RECEPTOR [$^3$H]naltrindole | μ RECEPTOR [$^3$H]DAMGO |
|---|---|---|---|
| NON-SELECTIVE COMPOUNDS |  |  |  |
| dynorphin A | 0.5 | >1000 | 32 |
| Leu-enkephalin | >1000 | >1000 | 3.4 |
| Met-enkephalin | >1000 | 4.0 | 3.4 |
| β-endorphin | 52 | 1.0 | 1.0 |
| des-Tyr$^1$-β-endorphin | >1000 | >1000 | >1000 |
| (−)naloxone | 2.3 | 17 | 0.93 |
| (+)naloxone | >1000 | >1000 | >1000 |
| levorphano | 6.5 | 5.0 | 0.086 |
| dextrorphan | >1000 | >1000 | >1000 |
| (±)bremazocine | 0.089 | 2.3 | 0.75 |
| ethylketocyclazocine | 0.40 | 101 | 3.1 |
| etorphine | 0.13 | 1.4 | 0.23 |
| pentazocine | 7.2 | 31 | 5.7 |
| diprenorphine | 0.017 | 0.23 | 0.072 |
| β-CNA | 0.083 | 115 | 0.90 |
| β-FNA | 2.8 | 48 | 0.33 |
| naltrexone | 3.9 | 149 | 1.0 |
| nalbuphine | 39 | >1000 | 11 |
| nalorphine | 1.1 | 148 | 0.97 |
| MU-SELECTIVE COMPOUNDS |  |  |  |
| CTOP | >1000 | >1000 | 0.18 |
| dermorphin | >1000 | >1000 | 0.33 |
| methadone | >1000 | >1000 | 0.72 |
| DAMGO | >1000 | >1000 | 2.0 |
| PLO17 | >1000 | >1000 | 30 |
| morphiceptin | >1000 | >1000 | 56 |
| codeine | >1000 | >1000 | 79 |
| fentanyl | 255 | >1000 | 0.39 |
| sufentanil | 75 | 50 | 0.15 |
| lofentanil | 5.9 | 5.5 | 0.68 |
| naloxonazine | 11 | 8.6 | 0.054 |
| morphine | 538 | >1000 | 14 |
| KAPPA-SELECTIVE COMPOUNDS |  |  |  |
| norBNI | 0.027 | 65 | 2.2 |
| spiradoline | 0.036 | >1000 | 21 |
| U-50,488 | 0.12 | >1000 | >1000 |
| U-69,593 | 0.59 | >1000 | >1000 |

TABLE 3-continued

BINDING POTENCIES (K$_i$-nM) OF LIGANDS FOR THE CLONED κ, δ AND μ OPIOID RECEPTORS

|  | κ RECEPTOR [$^3$H]U-69,593 | δ RECEPTOR [$^3$H]naltrindole | μ RECEPTOR [$^3$H]DAMGO |
|---|---|---|---|
| ICI 204,488 | 0.71 | >1000 | >1000 |
| DELTA-SELECTIVE COMPOUNDS |  |  |  |
| DPDPE | >1000 | 14 | >1000 |
| D-Ala$^2$-deltorphin II | >1000 | 3.3 | >1000 |
| DSLBT | >1000 | 4.8 | 39 |
| BW 3734 | 17 | 0.013 | 26 |
| DADL | >1000 | 0.74 | 16 |
| SIOM | >1000 | 1.7 | 33 |
| naltrindole | 66 | 0.02 | 64 |
| NTB | 13 | 0.66 | 1128 |
| BNTX | 55 | 0.66 | 18 |

Compounds which have been previously characterized as μ-selective including both peptide and non-peptide agonists and antagonists were also utilized. As expected, most of these compounds bound to the cloned μ receptor with K$_i$ values in the low nM range (Table 3). Exceptions include morphine, codeine, morphiceptin and PL017, which bind with affinities in the 10–100 nM range. The majority of the ligands tested are selective for the μ receptor and did not bind to the κ or δ receptors. Of the ligands which showed crossreactivity, fentanyl binds to the μ receptor with high selectivity but its derivatives lofentanil and sufentanil were less selective, interacting with both δ and κ receptors, albeit with lower affinity than with the μ receptor. Similar cross-reactivity was found with the compound naloxonazine, which has been suggested to discriminate between subtypes of μ receptors, having high affinity for the μ1 receptor (Pasternack and Wood, 1986). The high affinity of the cloned it receptor for naloxonazine, a compound possessing subtype selectivity (Pasternack and Wood, 1986), suggests that the cloned μ receptor corresponds to the endogenously expressed μ$_1$ receptor subtype.

Results with the κ$^−$ selective ligands U-50,488, U-69,593, ICI 204488 and spiradoline (Table 3) confirmed previous results showing their κ selectively (Lutz and Pfister, 1992; Goldstein and Naidu, 1989; Schiller, 1993; Portoghese, 1993; and Corbett et al., 1993). The κ antagonist norBNI was also selective for the κ receptor, but less so than the agonists tested. These results indicate that the cloned κ receptor corresponds pharmacologically to the κ$_1$ receptor previously characterized in heterogenous tissues (Clark et al., 1989).

Various peptide and non-peptide agonists and antagonists at the δ receptor (Lutz and Pfister, 1992; Goldstein and Naidu, 1989; Schiller, 1993; Portoghese, 1993; and Corbett et al., 1993) were tested and results confirmed the δ-selectivity of these compounds (Table 3). Thus, the peptide agonists DPDPE and D-Ala$^2$-deltorphin II are highly selective for the δ receptor, whereas DSLET and DADL are less selective. The recently developed nonpeptide agonists BW3734 (Lee et al., 1992) and SIOM (Portoghese et al., 1993) were also examined. BW3734 is highly δ-selective. We also tested compounds which have been proposed to distinguish between δ$_1$ and δ$_2$ receptor subtypes. These agents bound to the cloned δ receptor with differing affinities. The agonists DSLET and D-Ala$^2$ deltorphin II, which have been proposed as δ$_2$ ligands, were found to be more potent than DPDPE, which is δ$_1$-selective. Furthermore, the antagonists naltrindole and NTB were more potent than BNTX at binding to the cloned δ receptor. The pharmacological profile of the cloned δ opioid receptor differs from δ opioid receptors previously characterized in diverse tissues. The existence of subtypes of δ receptors has been suggested based on behavioral data employing compounds such as DPDPE and BNTX, which interact with $\delta_1$ receptors, and DSLET, D-Ala$^2$-deltorphin II, and NTB which interact with $\delta_2$ receptors (Sofuglu et al., 1991; Portoghese et al, 1992; and Sofuglu et al., 1991). The demonstration of the existence of δ receptor subtypes based on results of radioligand binding studies has been more ambiguous, perhaps due to the lack of sufficiently selective radioligands. These results suggest that the pharmacological profile of the cloned δ opioid receptor matches that of the $\delta_2$ receptor subtype.

Figure 6A:
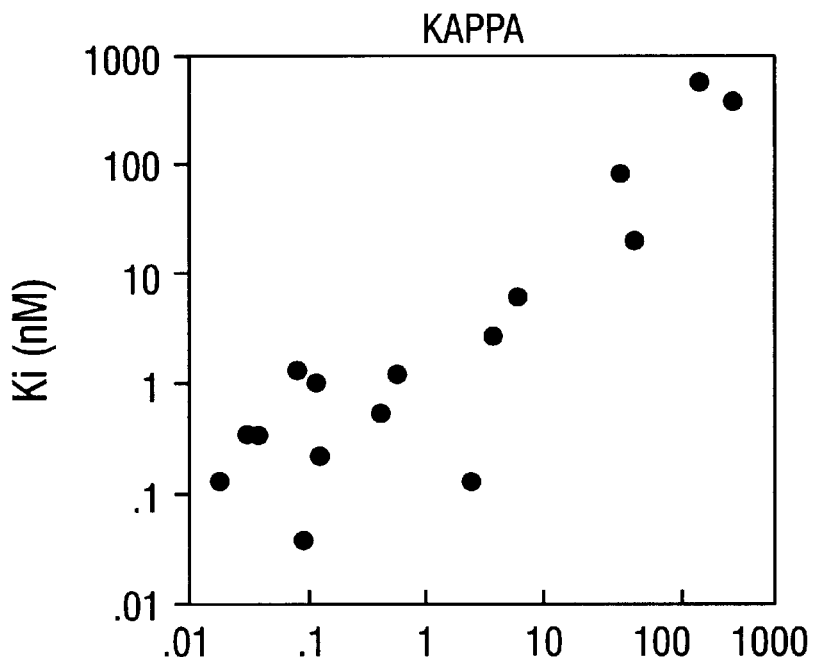
FIG. 6A and FIG. 6B show the correlation of the potencies of opioid ligands to inhibit radioligand binding to the cloned κ, δ, and $\mu$ opioid receptors with opioid receptors characterized in heterogenous tissues. Correlation analyses were performed by plotting the logarithm of the affinities of opioid ligands for the cloned κ (FIG. 6A) and cloned $\mu$ (FIG. 6B) receptors vs. the logrithm of the potencies of these compounds to inhibit subtype-selective radioligand binding to these opioid receptor types in heterogenous tissues. The affinities of ligands for the κ and $\mu$ receptors were highly correlated with literature values, with r values of 0.954 and 0.879, respectively. The correlation of potencies at the δ receptor was much poorer (r=0.185) (not plotted).
Figure 6B:
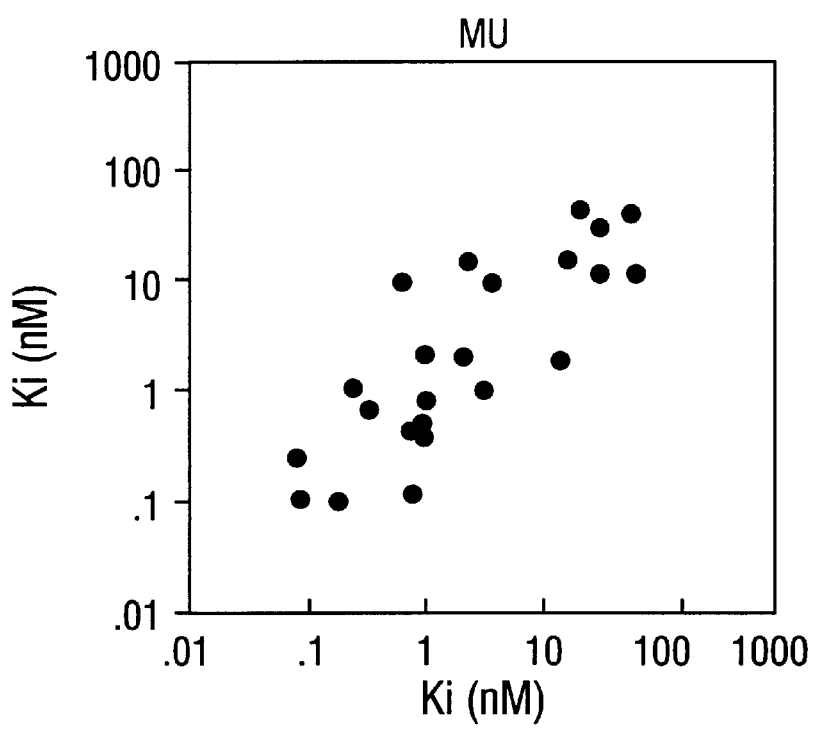

We performed correlational analyses comparing the $K_i$ values obtained in this study with those reported in the literature (Goldstein and Naidu, 1989; Schiller, 1993; Portoghese, 1993; and Corbett et al., 1993). To determine whether the pharmacological profiles of the cloned opioid receptors were similar to those previously reported for receptors expressed in vivo in biological tissues containing multiple opioid receptor subtypes. Compounds for which literature values were not available or which did not bind to a given receptor are not included in the analysis. The correlation coefficients obtained for both the μ (FIG. 6A) and κ (FIG. 6B) receptors are very high with r values of 0.954 (n=25) and 0.879 (n=16), respectively. In contrast, the correlation for the δ receptor is low, with an r value of 0.185 (n=17), indicating that the cloned δ receptor differs pharmacologically from those characterized in diverse tissues.

Interestingly, the endogenous opioid peptides β-endorphin, Leu- and Met-enkephalin were selective for the μ and δ receptors vs. the κ receptor. In fact, the $K_i$ values for these peptides were comparable at the μ and δ receptors. Becaused the potencies of the enkephalins to bind to the μ and δ receptors are within the physiological concentrations, these peptides may be endogenous ligands for both these receptor subtypes.

Our results indicate that opioid agents with abuse liabilities possess high affinities for the μ receptor. Thus, the addictive compounds morphine, fentanyl, and methadone have high affinities for the cloned μ receptor, but little or no affinity for the δ or κ receptors. Furthermore, etorphine, sufentanil, levorphanol, nalbuphine, and codeine, which have been shown to possess abuse liability (Jaffe and Martin, 1990) have in common relatively high affinity for the it receptor. Development of analgesic agents which are κ- or δ-selective may obviate this limitation of μ-selective analgesics.

The ability to individually study the pharmacological properties of the cloned opioid receptor subtypes will allow for identification of structural features of ligands which permit selective interactions. Identification of the pharmacological interactions of drugs which the individual opioid receptors could lead to the identification of therapeutic agents less burdened with the potential to produce undesirable side effects.

Example 7
Chimeric Opioid Receptors

Opioids such as morphine are used for the management of chronic pain (Jaffe and Martin, 1990). However, the use of opioids has undesirable side effects including respiratory depression, decreased gastrointestinal motility, sedation, nausea, and mood changes. Other major limitations include abuse potential, tolerance, and dependence. Morphine and the endogenous opioid peptides, the enkephalins, endorphins, and dynorphins, exert their physiological effects through membrane-bound receptors expressed in the central and peripheral nervous systems and target tissues.

Figure 7A:
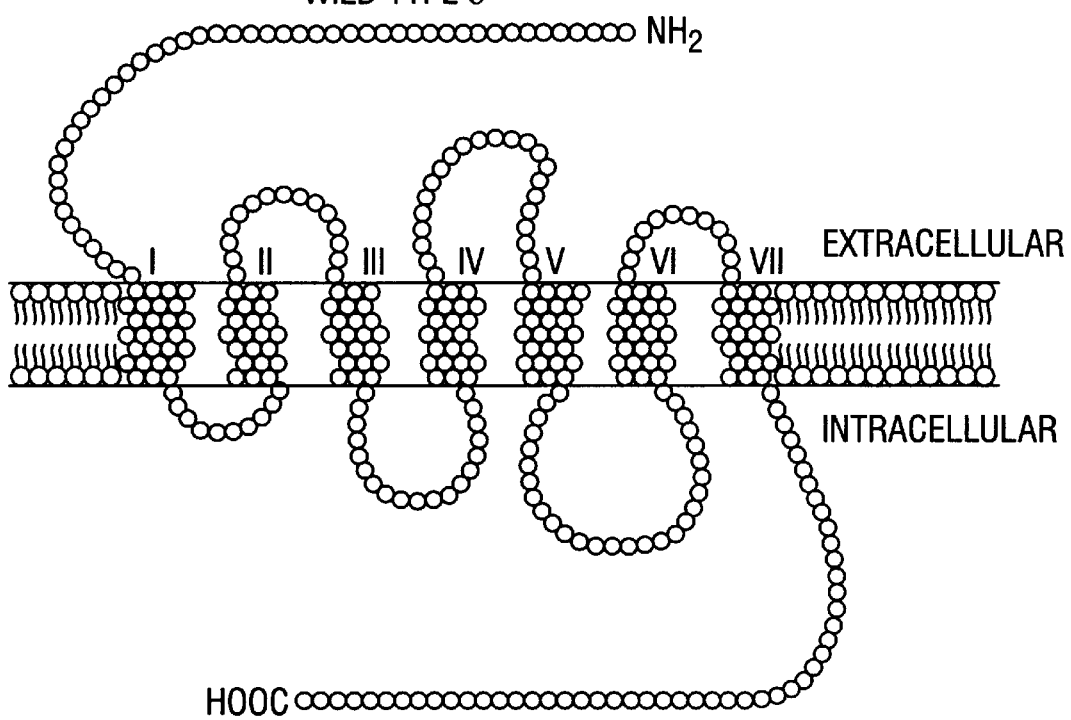
FIG. 7A, FIG. 7B, FIG. 7C, and FIG. 7D show a schematic of wild-type δ receptor (FIG. 7A); a schematic of wild-type κ receptor (FIG. 7B); a schematic of $\kappa_{1-78}/\delta_{70-372}$ chimeric receptor (FIG. 7C); and a schematic of $\delta_{1-69}/\kappa_{79-380}$ chimeric receptor (FIG. 7D).
Figure 7B:
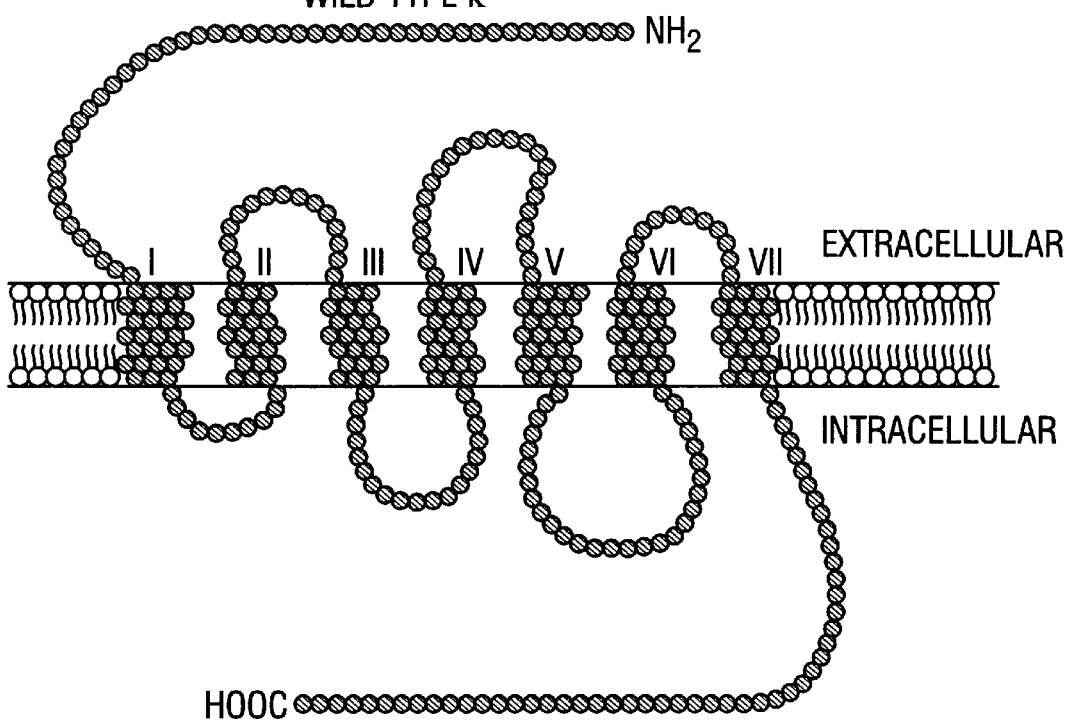
Figure 7C:
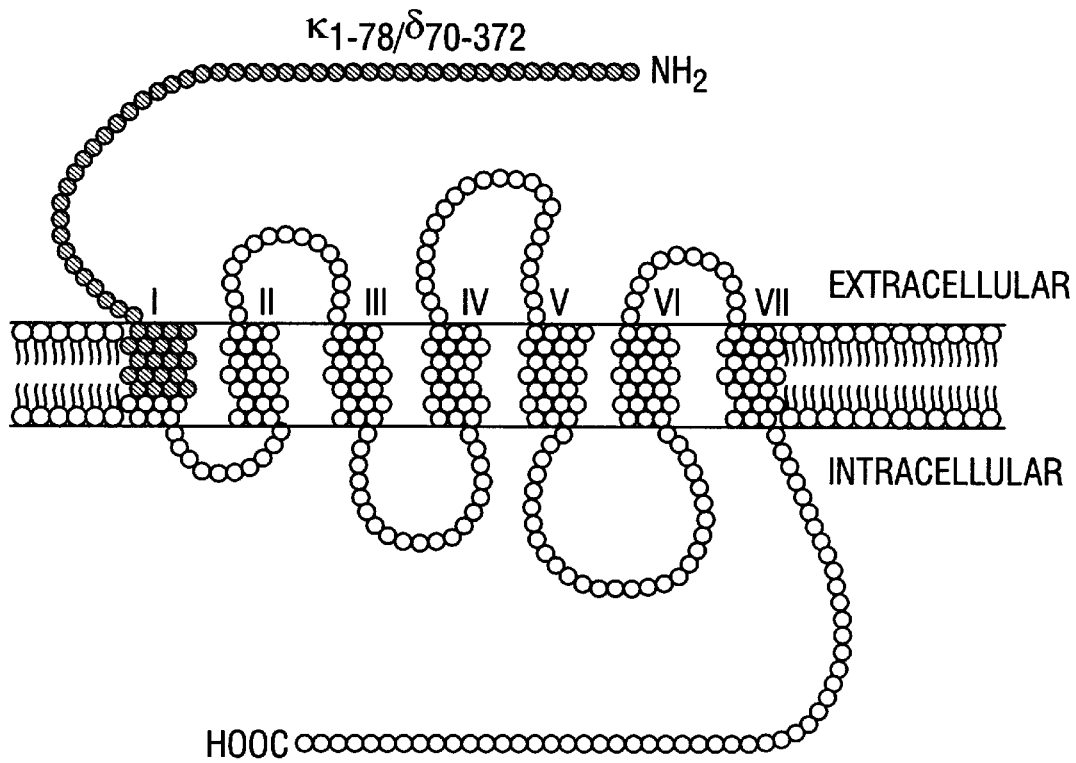
Figure 7D:
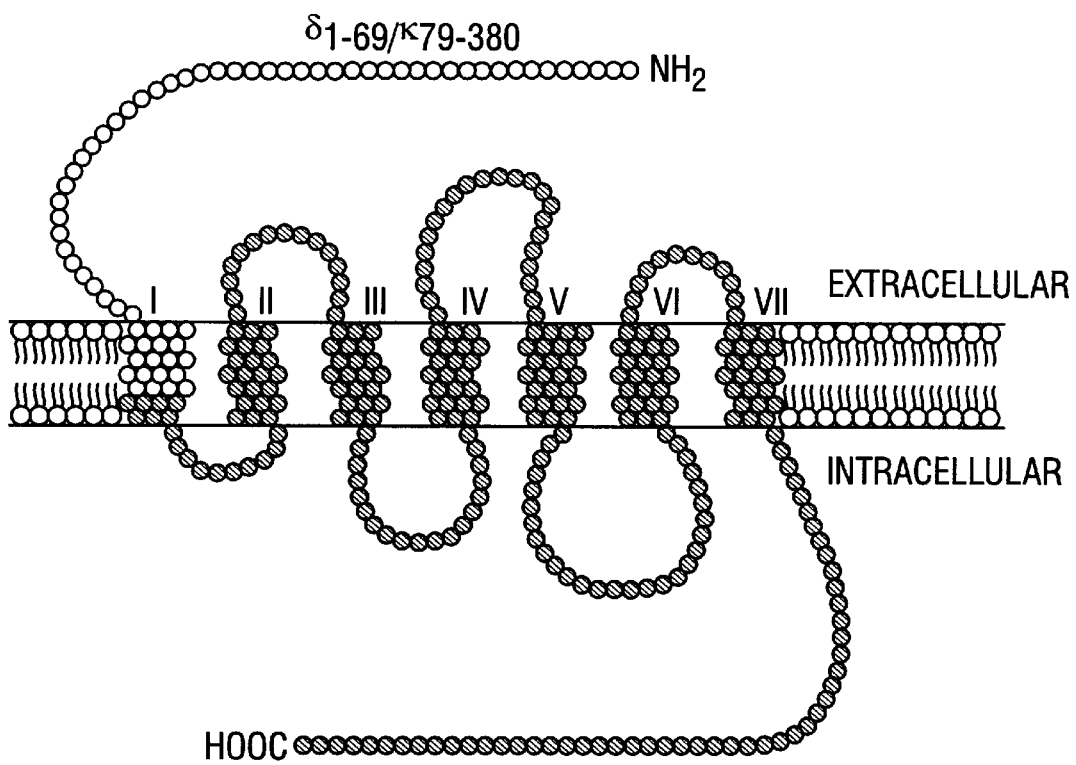

The three major-types of opioid receptors, δ, κ and μ, that have been cloned and functionally characterized (Evans et al., 1993; Kieffer et al., 1992; Yasuda et al., 1993; and Chen et al., 1993) belong to the DRY-containing subfamily of seven transmembrane-spanning receptors. There is ~60% amino acid identity among the sequences of the δ, κ and μ opioid receptors. The sequences of the putative membrane-spanning segments (TM I–VII) and the three intracellular loops connecting these segments are highly conserved whereas the sequences of the extracellular $NH_2$-termini segments, second and third extracellular loops and the intracellular COOH-termini are divergent. These divergent extracellular regions are likely to be responsible for the distinct ligand binding profiles of the δ, κ and μ receptors. The present invention describes the preparation and characterization of chimeric opioid receptors. The chimeric receptors include $\kappa_{1-78}/\delta_{70-372}$, $\delta_{1-69}/\kappa_{79-380}$, $\kappa_{1-74}/\delta_{65-372}$ and $\delta_{1-64}/\kappa_{75-380}$. In the notation for chimeric receptors, the amino terminus is designated first and the carboxy terminus is designated second. Thus for $\kappa_{1-78}/\delta_{70-372}$, the amino terminus of the chimera is composed of amino acid residues 1–78 of the kappa receptor and the carboxy terminus is composed of amino residues 70–372 of the delta receptor. FIG. 7C and FIG. 7D show a pictorial representation of chimeras $\kappa_{1-78}/\delta_{70-372}$ and $\delta_{1-69}/\kappa_{79-380}$, respectively. The agonist and antagonist binding properties of these chimeras as well as the chimera's ability to mediate inhibition of adenylyl cyclase activity are also described.

Generation of Chimeras

To exchange $NH_2$-termini between the mouse δ and κ opioid receptors, a common restriction site. SpeI, was generated at an equivalent position in the cDNAs in the region encoding the first transmembrane domain without otherwise altering the amino acid sequence of either receptor. Site-directed mutagenesis was carried out using the Altered Sites™ In vitro Mutagenesis System (Promega, Madison, Wis.) and 27-mer oligonucleotides containing the SpeI site, δ receptor oligonucleotide - CTGGGCAACGTACTAGTCATGTTTGGC (SEQ ID NO:42) and κ receptor oligonucleotide - GTGGGCAAT-TCACTAGTCATGTTTGTC (SEQ ID NO:43). After digestion with SpeI and the appropriate 5' and/or 3' enzymes, the cDNA fragments encoding the $NH_2$- and COOH-termini of δ and κ were isolated from a 1.2% low melting point agarose gel. Fragments encoding the $NH_2$-terminus of δ receptor and the COOH-terminus of κ receptor and vice versa were ligated together and cloned into the mammalian expression vector pCMV-6c. Truncated δ and κ receptors were generated by ligating the fragments encoding the COOH-termini directly into the expression vector; translation of the receptor sequences in these constructs was predicted to begin at a conserved ATG just distal to the SpeI site.

Figure 8:
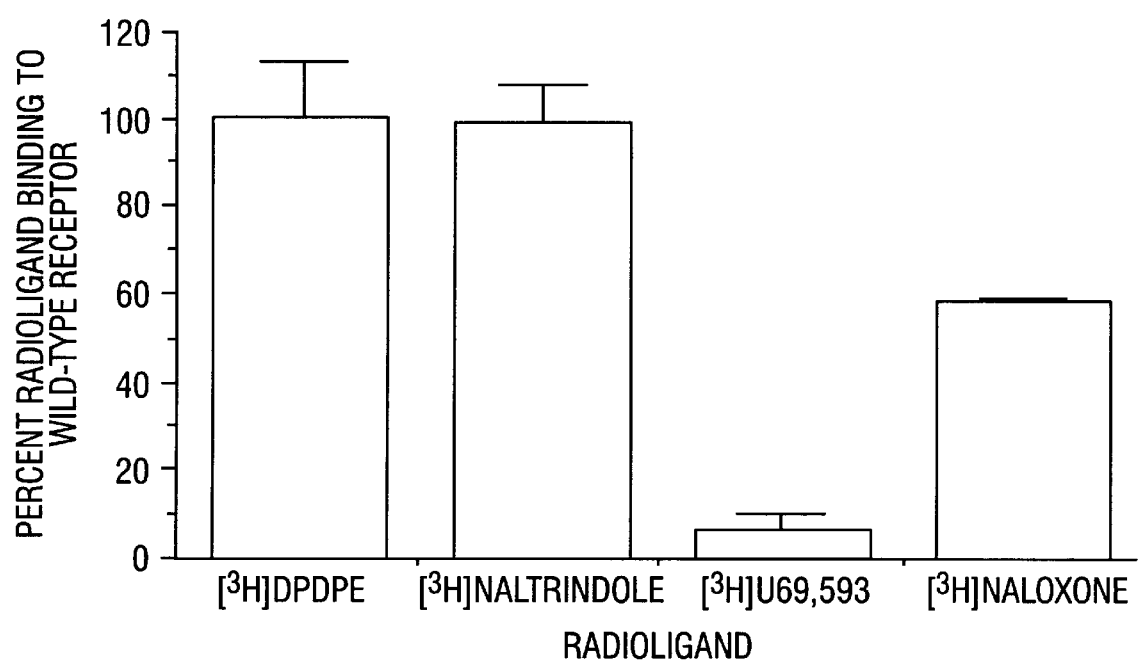
FIG. 8 shows the binding properties of the chimeric $\kappa_{1-78}/\delta_{70-372}$ receptor. Binding if δ- and κ-selective agonists and antagonists to the chimeric $\kappa_{1-78}/\delta_{70-372}$ receptor. COS-7 cells were transfected by the calcium phosphate precipitation method with the wild-type δ or κ or $\kappa_{1-78}/\delta_{70-372}$ receptor cDNAs. δ- and κ-selective agonists ([$^3$H] DPDPE and [$^3$H]U-69,593, respectively) and antagonists ([$^3$H]naltrindole and [$^3$H]naloxone, respectively) were tested for their abilities to bind to the $\kappa_{1-78}/\delta_{70-372}$ receptor. Values are express as percent [$^3$H]DPDPE and [$^3$H] naltrindole binding to wild-type δ and [$^3$H]U-69,593 and [$^3$H]naloxone binding to wild-type κ receptors. The average binding of [$^3$H]DPDPE and [$^3$H]naltrindole to wild-type δ receptor was 1987 fmol/mg protein and 2404 fmol/mg protein, respectively; the average binding of [$^3$H]U-69,593 and [$^3$H]naloxone to wild-type κ receptor was 998 fmol/mg protein and 2085 fmol/mg protein, respectively. These are the average results of 3–4 different experiments.

As shown previously (Evans et al., 1993; Kieffer et al., 1992; Yasuda et al., 1993; and Chen et al., 1993), the wild-type κ receptor can be labeled with the κ-selective agonist [$^3$H]U-69,593 and the antagonist [$^3$H]naloxone, and the wild-type δ receptor can be labeled with the δ-selective agonist, [$^3$H][D-Pen$^2$, D-Pen$^5$]-enkephalin (DPDPE) and with the antagonist, [$^3$H]naltrindole. The κ-selective and δ-selective ligands have minimal cross reactivity. The $\kappa_{1-78}/\delta_{70-372}$ and $\delta_{1-69}/\kappa_{79-380}$ chimeric opioid receptors show unique agonist and antagonist binding properties. The $\kappa_{1-78}/\delta_{70-372}$ receptor binds the antagonist, [$^3$H]naloxone (which poorly labels the wild-type δ receptor), and the δ-selective agonist and antagonist, [$^3$H]DPDPE and [$^3$H]naltrindole, respectively (FIG. 8). In contrast, the $\delta_{1-69}/\kappa_{79-380}$ receptor binds only the κ-selective agonist [$^3$H]U-69,593, although at lower levels when compared to the wild-type κ-receptor which binds at 46 fmol/mg protein. These results show that agonist and antagonist binding domains of the κ receptor are separable and located in different regions of the protein. The antagonist binding domain of κ is localized to the region of amino acids 1–78 which includes the NH$_2$-terminal extracellular domain. In contrast, the antagonist binding domain of the δ receptor is not located in the corresponding region of this receptor.

Radioligand Binding Assay

For receptor binding studies, COS-7 cells expressing the receptors are harvested 72 hours after transfection in 50 nM Tris-HCI (pH 7.8) containing 1 mM EGTA, 5 mM MgCl$_2$, 10 μg/ml leupeptin, 10 μg/ml pepstatin, 200 μg/ml bacitracin, and 0.5 μg/ml aprotinin (Buffer 1) and centrifuged at 24,000×g for 7 min at 4° C. and the pellet resuspended in Buffer 1 using a polytron. The homogenate is centrifuged at 48,000×g for 20 min at 4° C. and the pellet resuspended in Buffer 1 and used in the radioligand binding assay. Cell membranes (10–20 μg of protein) were incubated with [$^3$H]U69,593 (2 nM, specific activity 47.4 Ci/mmol), [$^3$H]naloxone (6 nM, specific activity 72.1 Ci/mmol), [$^3$H]DPDPE (2 nM, specific activity 34.3 Ci/mmol), or [$^3$H]naltrindole (1 nM, specific activity 31.2 Ci/mmol) in a final volume of 200 μl for 40 min at 25° C. in the presence or absence of competing agents. All radioligands were obtained from NEN/Dupont (Boston, Mass.). Nonspecific binding is defined as radioactivity remaining bound in the presence of 1 μM naltrindole or naloxone for δ- and κ-selective ligands, respectively. The binding reaction is terminated by the addition of ice-cold 50 mM Tris-HCI (pH 7.8) and rapid filtration over Whatman GF/B glass fiber filters that were pretreated with 0.5% polyethleneimine and 0.1% bovine serum albumin. The filters were washed with 12 ml of ice-cold buffer and soaked overnight in scintillation fluid. The bound radioactivity was determined using a scintillation counter. IC$_{50}$ values were obtained using the curve-fitting program FITCOMP on the NIH-based Prophet system (H. Perry and P. McGonigle in PHOPHET *Public Procedure Notebook*. (Bolt, Berabek, and Newman, Inc., Cambridge, Mass., 1988), pp. 187–197.

Figure 9A:
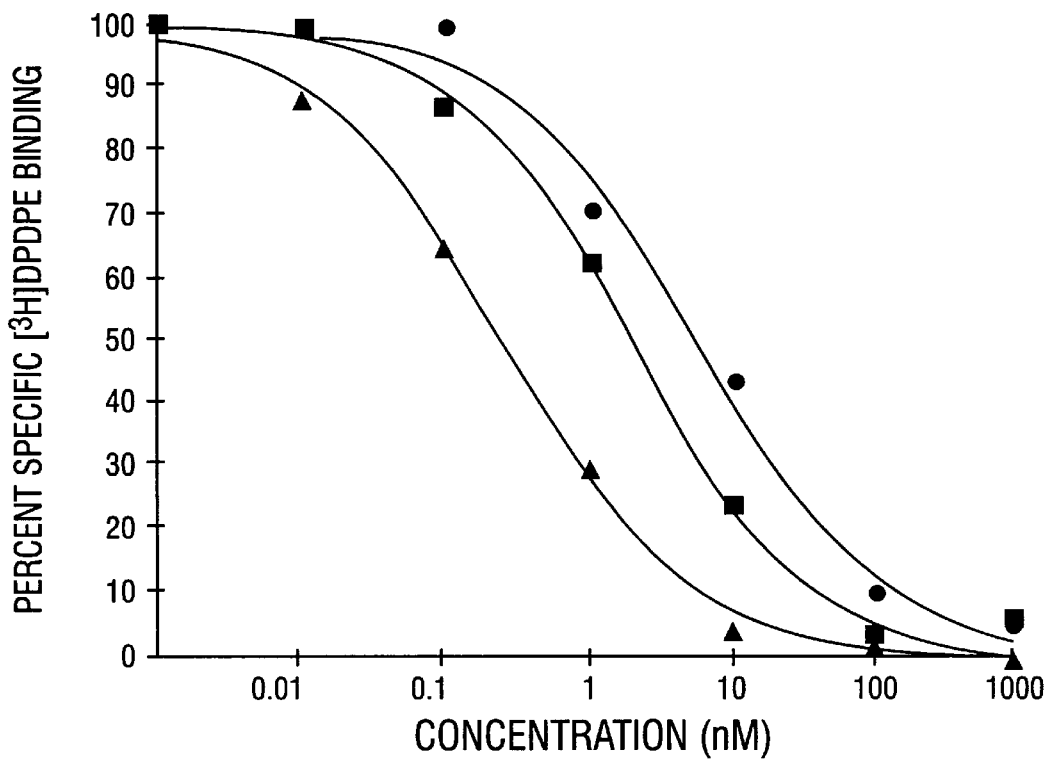
FIG. 9A and FIG. 9B show the inhibition of [$^3$H]DPDPE (FIG. 9A) and [$^3$H]naloxone (FIG. 9B) binding to the $\kappa_{1-78}/\delta_{70-372}$ chimera by κ- and δ-selective agents. The δ-selective agonists DSLET (■) and DPDPE (●) and the δ-selective antagonist naltrindole (▲) were tested for their abilities to inhibit [$^3$H]DPDPE binding to this chimera (top). $IC_{50}$ values for inhibition of [$^3$H]DPDPE binding were 5.8, 2.0 and 0.25 nM for DPDPE, DSLET and naltrindole, respectively. The $IC_{50}$ value for inhibition of [$^3$H]naloxone binding was 14 nM for naloxone (♦), but the κ-selective agonist U-50,488 (★) did not inhibit [$^3$H]naloxone binding to the $κ_{1-78}/δ_{70-372}$ chimera (bottom).
Figure 9B:
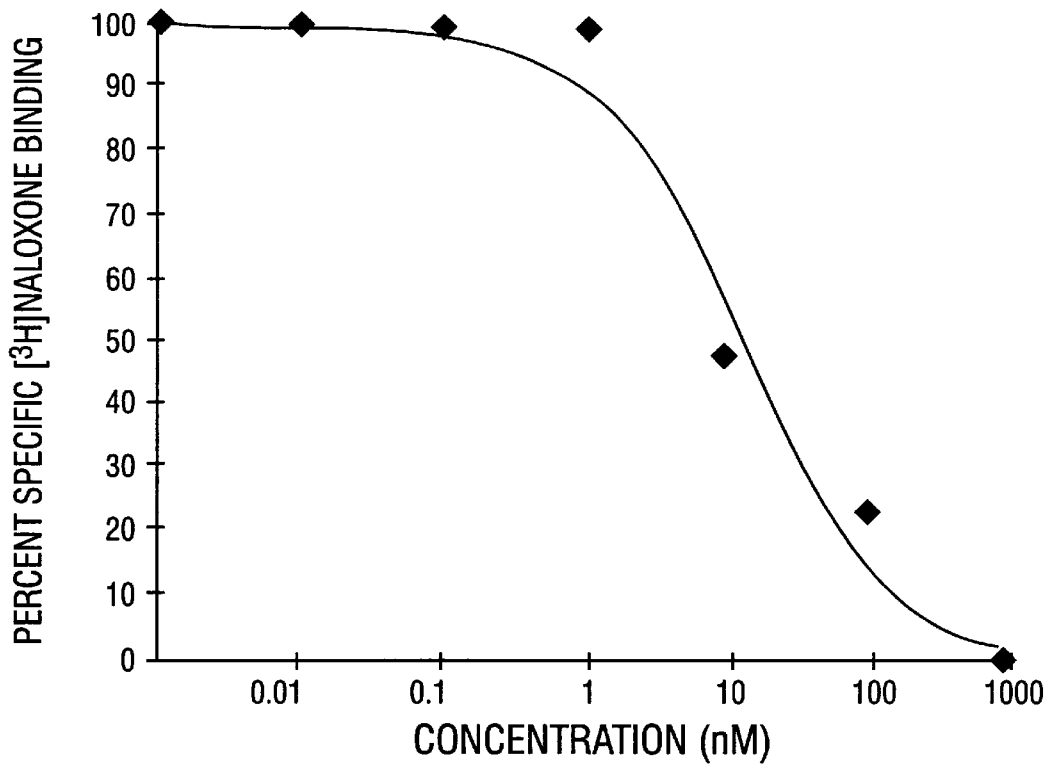

The binding properties of the $\kappa_{1-78}/\delta_{70-372}$ chimera were further examined by inhibition studies. As shown in FIG. 9A and FIG. 9B [$^3$H]naloxone binding to the $\kappa_{1-78}/\delta_{70-372}$ chimera was not inhibited by the δ-selective agonist U-50, 488. Dynorphin, the endogenous ligand for the κ receptor, inhibited [$^3$H]naloxone binding to the $\kappa_{1-78}/\delta_{70-372}$ chimera with an IC$_{50}$ value of 40 nM, which is approximately 500-fold less potent than the binding observed for wild-type κ receptor (2). [$^3$H]naloxone binding was dose-dependent and was potently inhibited by the antagonist naloxone with an IC$_{50}$ value of 14 nM (FIG. 9A and FIG. 9B) and was also inhibited by the κ-selective antagonist nor-binaltorphimine (norBNI) with an IC$_{50}$ value of 0.14 nM. [$^3$H]Naltrindole binding to this chimera was inhibited in a dose-dependent manner by the potent δ-selective agonists [D-Ser$^2$]-Leu-enkephalin-Thr (DSLET) and DPDPE and the δ-selective antagonist naltrindole. This results show that the agonist and antagonist binding sites in the δ receptor are contained within residues 70–372.

Cyclic AMP Accumulation Assays cAMP accumulation in COS-7 cells expressing the wild-type or mutant receptors is measured as previously described (Yasuda et al., 1992). Briefly, COS-7 cells were subcultured in 12-well culture plates. The cells were transfected 72 hours prior to the cAMP experiments. Culture medium was removed from the wells and replaced with 500 μl of fresh medium containing 0.5 mM isobutylmethylxanthine (IBMX). Cells were incubated for 20 min at 37° C. Medium was removed and replaced with fresh medium containing 0.5 mM IBMX, with or without 10 μM forskolin and various opioid agonists and antagonists. The cells were incubated for 30 min at 37° C. Medium was removed and cells sonicated in the wells in 500 μl of 1 N HCl. HCl was removed under vacuum and the cAMP quantified using a radioimmunoassay kit from DuPont-New England Nuclear.

Figure 10A:
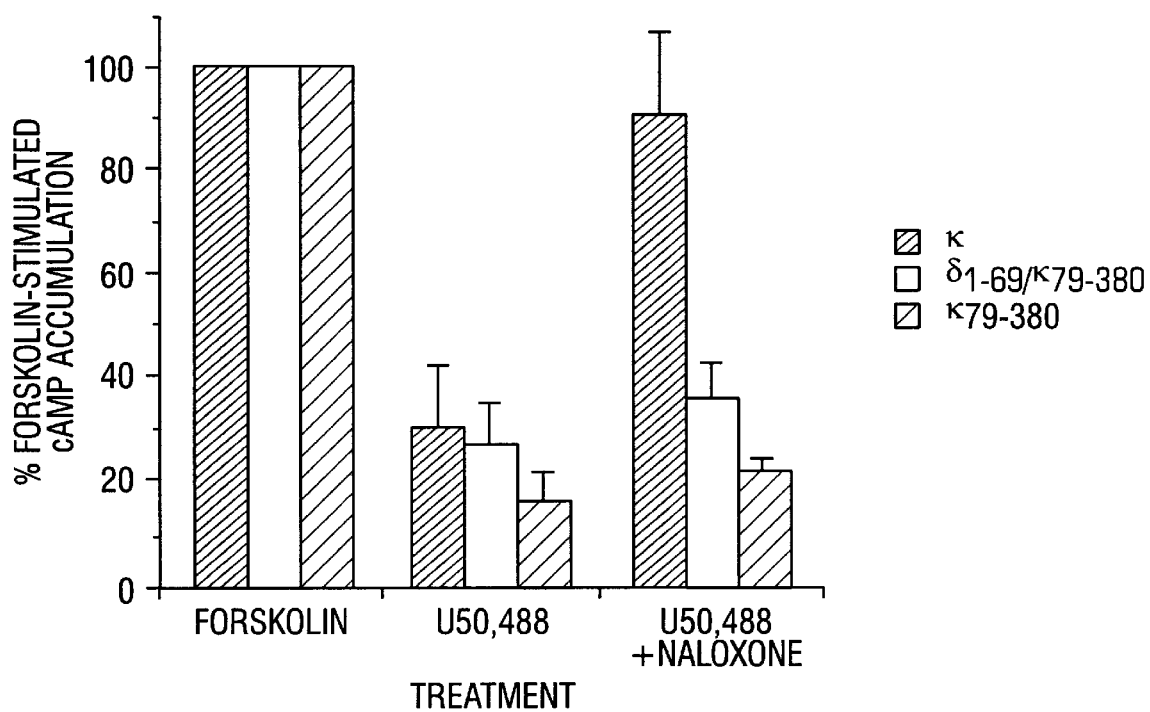
FIG. 10A and FIG. 10B show the inhibition of forskolin-stimulated cAMP accumulation. COS-7 cells were transfected by the calcium phosphate precipitation method with wild-type (solid bars), chimeric (open bars) or truncated (hatched bars) receptor cDNA. κ- and δ-selective agonists (1 μM U-50,488 and DSLET, respectively) were tested for their abilities to inhibit 10 μM forskolin-stimulated cAMP accumulation. The abilities of κ- and δ-selective antagonists (1 μM naloxone and naltrindole, respectively) to block the effects of agonists were also examined. Results were calculated as a percent of forskolin-stimulated cAMP accumulation (173 pmol/well for wild-type δ receptor, 244 pmol/well for wild-type κ receptor, 172 pmol/well for $δ_{1-69}/κ_{79-380}$ receptor, 205 pmol/well for $κ_{1-78}/δ_{70-372}$ receptor, 100 pmol/well for $δ_{70-372}$ receptor, and 51 pmol/well for $κ_{79-380}$ receptor). Basal cAMP levels, which were <5% of forskolin-stimulated cAMP levels, were subtracted for all values. The results are the means±S.E.M. of 3 different experiments.
Figure 10B:
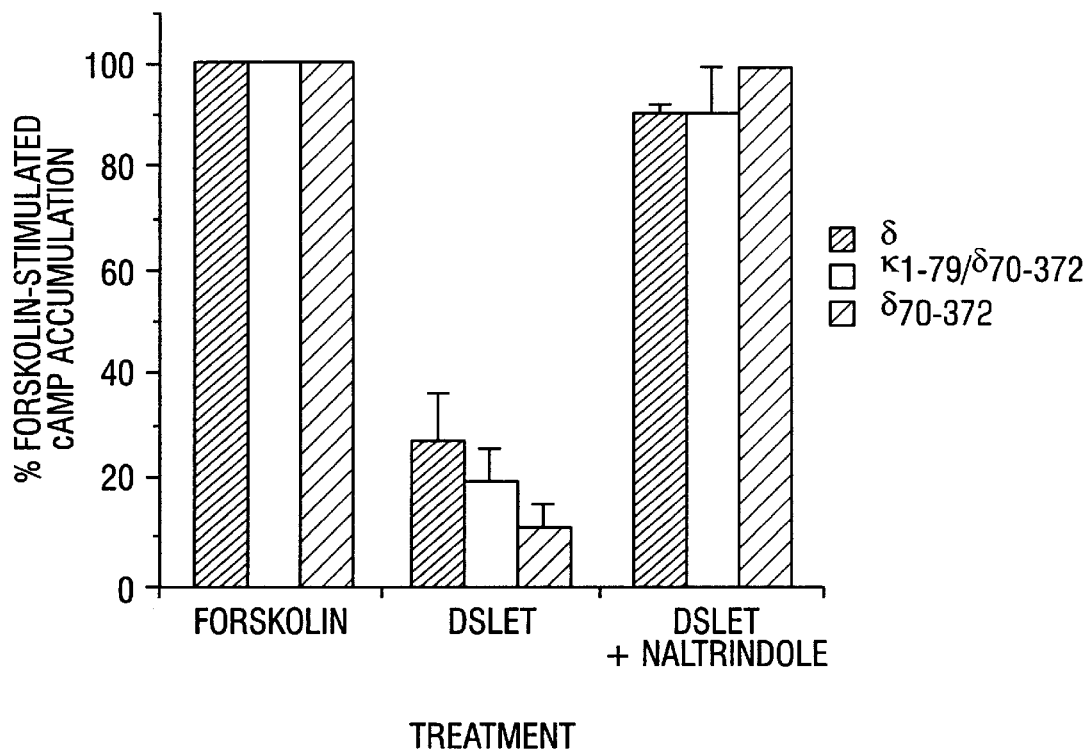

As shown in FIG. 10A and FIG. 10B, $\kappa_{1-78}/\delta_{70-372}$ and $\delta_{1-69}/\kappa_{79-380}$ chimeras were functionally active and can mediate selective agonist inhibition of forskolin-stimulated cyclic AMP (cAMP) accumulation (Yasuda et al., 1992). Inhibition of cAMP accumulation by U-50,488 via the $\delta_{1-69}/\kappa_{79-380}$ chimera was not blocked by naloxone. The potency of U-50,488 to inhibit cAMP formation was approximately 1 nM which is similar to its potency at interacting with wild-type κ receptor. Furthermore, dynorphin was able to inhibit cAMP formation via the $\delta_{1-69}/\kappa_{79-380}$ chimera and its effects were not blocked by naloxone. Thus it is likely that the naloxone binding site resides in the NH$_2$-terminus of the κ receptor. Expression of a truncated version of the κ receptor, $\kappa_{79-380}$, in which the extracellular NH$_2$-terminal domain is missing also shows that the naloxone binding site resides in the amino terminus. Cells transfected with a construct encoding this truncated κ receptor showed little specific [$^3$H]-U69,593 binding but were able to mediate U-50,488 inhibition of forskolin-stimulated cAMP formation (FIG. 10A). This effect was not blocked by the κ-selective antagonist naloxone, consistent with residues 1–78 not being involved in agonist recognition but necessary for antagonism by naloxone. Furthermore, the δ-selective agonist DSLET had no effect on cAMP formation in cells expressing the truncated κ receptor, as with the $\delta_{1-69}/\kappa_{79-380}$ chimera.

Expression in COS-7 cells of the chimeric $\kappa_{1-78}/\delta_{70-372}$ or the truncated δ receptor, $\delta_{70-372}$, conferred functional properties indistinguishable from the wild-type δ receptor (FIG. 9B). FIG. 10A and 10B shows that the δ-selective agonist DSLET was inhibited forskolin-stimulated cAMP formation which was blocked by naltrindole. This result demonstrates that the agonist and antagonist binding domains of the δ receptor is localized to residues 70–372. The κ-selective agonist U-50,488 did not have any effect on the functional properties of the $\kappa_{1-78}/\delta_{70-372}$ receptor or the truncated δ receptor, $\delta_{70-372}$.

The present invention demonstrates an unexpected difference between the κ and δ receptors with respect to the locations of agonist and antagonist binding domains and the important role played by the NH$_2$-terminal 78 residues of the κ receptor in antagonist binding. The demonstration that agonists and antagonists bind to different regions of the κ receptor should facilitate development of more selective κ ligands. This is an area of considerable interest Because κ receptor-selective agents have limited abuse potential and respiratory depressant effects development of κ selective ligans is of considerable interest. The structural analysis of the ligand binding domains of the opioid receptors will provide the basis for the rational design of a new generation of therapeutically useful analgesics with limited side effects.

REFERENCES CITED

The references listed below as well as all references cited in the specification are incorporated herein by reference to the extent that they supplement, explain, provide a background for or teach methodology, techniques and/or compositions employed herein.

Adelman et al. (1983) *DNA* 2:183.
Akil, H. et al. (1984) *Annu. Rev. Neurosci.* 7:223.
Attali, B. et al. (1989) *J. Neurochem.* 52:360.
Benovic et al. (1989) *Science* 246:235.
Bertin, B. et al. (1992) *J. Biol. Chem.* 267(12):8200.
Bero, et al. (1988) *Mol. Pharmacol.* 34:614.
Bertolucci, M. et al. *Neurosci, Abstr.* 18L1368.
Bolivar et al., (1977) *Gene,* 2:95.
Boshart et al. (1985) *Cell* 41:521.
Bouvier, M. et al. (1988) *Mol. Pharmacol.* 33:133.
Bradbury, A. F. et al. (1976) *Nature* 260:165.
Breder, C. D. et al. (1992). *J. Neurosci* 12:3920.
Chang et al., (1978) *Nature,* 375:615.
Chen et al. (1993) *Mol. pharmacol.* 44:8.
Cheng and Prusoff, (1973) *Biodchem. Pharmacol.* 22:3099.
Chesselet et al. (1987) *J. Comp. Neurol.* 262:125.
Childers, S. (1991) *Life Sci.* 48:991.
Clark, J. A. et al. (1989) *J. Pharmacol. Expt. Therapeut.* 251:461.
Corbett et al. (1993) *Opioids I* 104:645.
Cotecchia et al. (1988) *Proc. Nail. Acad. Sci. USA* 85:7159.
Cowan, A. and Murray, C. (1990) *Prog. Clin. Biol. Res.* 328:303.
Crea et al., (1978) *Proc. Natl. Acad. Sci. U.S.A,* 75:5765.
Danboldt, N. C. et al. (1990) *Biochemistry* 29(28):6734.
Di Chiara, G. et al. (1992) *Trends Pharmacol. Sci.* 13:185.
Dohlman (1987) *Biochemistry* 26:2657.
Dohlman, H. G. (1991) *Annu. Rev. Biochem.* 60:166–170; 174–s176; 653–688.
Evans et al., (1992) *Science* 258:1952.
Ferruti, P. and Tanzi, M. C., (1986) *Cris. Rev. Ther. Drug Carrier Syst.* 2:117–136.
Fiers et al., (1978) *Nature* 273:113.
Frielle, T. et al. (1988) *Proc. Natl. Acad. Sci. USA* 85:9484.
Gabizon, A. et al., (1990) *Cancer Res.* 50:6371–6378
Gioannini, T. L. et al. (1989) *J. Mol. Recogn.* 2:44.
Goeddel et al., (1979) *Nature,* 281:544.
Goeddel et al., (1980) *Nucleic Acids Res.,* 8:4057.
Goldstein and Naidu, (1989) *Mol. Pharmacol.* 36:265.
Gransch, C. et al. (1988) *J. Biol. Chem.* 263:5853.
Hausdorff, et al. (1990) *FASEB J* 4:2881.
Hess et al., (1968) *J. Adv. Enzyme Reg.* 7:149.
Heyman et al. (1988) *TIPS* 9:134.
Hitzeman et al., (1980) *J. Biol. Chem.* 255:2073.
Holland et al., (1978) *Biochemistry* 17:4900.
Horstman, D. A. et al. (1990) *J. Biol. Chem.* 265:21590.
Hsia, J. A. et al. (1984) *J. Biol. Chem.* 259:1086.
Hughes, J. et al. (1975) *Nature* 258:577.
Itakura et al., (1977) *Science,* 198:1056.
Jaffe and W. R. Martin in *The Pharmacological Basis of Therapeutics,* 8th Ed., A. Gilman, J. Rall, A. Nies, P. Taylor, Eds. (Pergamon Press, New York, 1990), pp. 485–573.
Jones, (1977) *Genetics* 85:12.
Kanaho et al. (1984) *J. Biol. Chem.* 259:7378.
Kennelly, P. J. et al. (1991) *J. Biol. Chem.* 266:15555.
Kieffer et al., (1992) *Proc. Natl. Acad. Sci. U.S.A.* 89:12048.
King et al. (1990) *Science* 250:121.
Kingsman et al., (1979) *Gene* 7:141.
Kobilka, B. K. et al. (1987) *J. Biol. Chem.* 262:7321.
Kobilka, B. K. et al. (1988) *Science* 240:1310.
Koob, G. F. et al. (1992) *Trends Neurosci.* 15:186.
Koob, G. and Bloom, F. (1992) *Science* 242:715.
Kozasa et al. (1988) *Proc. Natl. Acad. Sci USA* 85:2081.
Kruse and Patterson, eds. (1973) *Tissue Culture,* Academic Press.
Kyte, J., and R. F. Doolittle (1982) *J. Mol. Biol.* 157:105.
Law, et al. (1983) *Mol. Pharmacol.* 23:26.
Law, S. F. and Reisine, T. (1992) *Mol. Pharmacol.* 42:398.
Law, S. et al. (1991) *J. Biol. Chem.* 266:17885.
Law, S. F. et al. (1993) *J. Biol. Chem.* 268:10721.
Lee et al. (1992) *Int'l Narcotic Research Conference,* Abstract 34.
Loh, H. H. et al., (1990) *Annu. Rev. Pharmacol. Toxicol.* 30:123.
Loh, H. and Smith, A. (1990) *Annu. Rev. Pharmacol.* 30:123.
Lomasney et al. (1990) *Proc. Natl. Acad. Sci. USA* 87:5094.
Lutz, R. A. et al. (1992) *J. Receptor Res.* 12:267.
Mansour, A. et al. (1987) *J. Neurosci.* 7:2445.
Marullo et al. (1988) *Proc. Natl. Acad. Sci. USA* 85:7551.
McGonigle et al. (1988) *PROPHET Public Procedures Notebook* 215.
Messing et al., *Third Cleveland Symposium on Macromolecules and Recombinant DNA,* Editor A. Walton, Elsevier, Amsterdam (1981).
Muller et al. (1990) *DNA and Cell Biol.* 9:221.
Nathans et al. (1986 A) *Science* 232:193.
Nathans et al. (1986 B) *Science* 232:203
Nestler, E. (1993) *Crit. Rev. in Neurobiol.* 7:23.
Nock, B. et al. (1988) *Eur. J. Pharmacol.* 154:27.
Okayama et al. (1983) *Mol. Cell Biol.* 3:280.
Okuma, Y. and Reisine, T. (1992) *J. Biol. Chem.* 267:14826.
Olson, G. A. et al. (1989) *Peptides* 10:1253.
Ott, S. et al. (1988) *J. Biol. Chem.* 263:10524.
Pasternack (1993) *Clin. Neuropharmacology* 16:1.
Pasternack and Wood (1986) *Life Sci.* 38:1889.
Payette et al. (1990) *FEBS Lett.* 266:21.
Perry and McGonigle in *PHOPHET Public Procedure Notebook.* (Bolt, Berabek, and Newman, Inc., Cambrige, Mass., 1988), pp. 187–197.
Pert, C. G. et al. (1973) *Science* 179: 1011.
Pert, C. B. et al. (1974) *Mol. Pharmacol.* 10:868.
Pfeiffer, A. et al. (1986) *Science* 223:774.
Portoghese (1993) *Opioids I* 104:276.
Portoghese et al. (1993) *J. Med. Chem.* 36:2572.
Portoghese et al. (1992) *Eur J. Pharmacol.* 218:195.
Puttfarcken, P. S. et al. (1988) *Mol. Pharmacol.* 33:520.
Ranade, V. V. (1989) *J. Clin. Pharmacol.* 29:685–694
Raynor, K. and Reisine, T. (1989) *J. Pharmacol Expt. Therap.* 251:510.
Regan et al. (1988) *Proc. Natl. Acad. Sci. USA* 85:6301.
Rens-Domiano et al. (1992) *Mol. Pharmacol.* 42:28.
Sambrook, J. et al. (1989) *Molecular Cloning: A Laboratory Manual* (Cold Spring Harbor Laboratory Press, Cold Spring Harbor, N.Y.).
Schiller, (1993) *Opioids I* 104:681.
Seeburg (1982) *DNA* 1:239.
Shook, J. E. et al. (1990) *Am. Rev. Respir. Dis.* 142:895.
Siebwenlist et al., (1980) *Cell,* 20:269.
Simon, E. J. (1991) *Medicinal Res. Rev.* 11:357.
Sofuglu et al. (1991) *J. Pharmacol. Exp. Ther.* 257:676.
Sofuglu et al. (1991) *Life Sci.* 49:153.
Soghomonian et al. (1992) *Brain Res.* 576:68.
Stinchcomb et al., (1979) *Nature,* 282:39.
Stratford-Perricaudet et al. (1992).
Strotchman and Simon (1991).
Tallarida, R. and Murray, R. (1987) *Manual of Pharmacological calculations with computer programs,* 2nd ed.
Thomsen et al. (1984) *PNAS* 81:659.
Tortella, R. et al. (1981) *Life Sci.* 10:1039.
Tschemper et al., (1980) *Gene* 10:157.
Unterwald, E. M. et al. (1991) *Brain Res.* 562:57.

Unterwald, E. M. et al. (1987) *Eur. J. Pharmacol.* 133:275.
Weiss-Wunder, L. and Chesselet, M. F. (1991) *J. Comp. Neurol.* 303:478.
Xie, G-X., et al. (1992) *Proc. Natl. Acad. Sci. USA* 89:4124.
Yamada, Y. et al. (1992) *Proc. Natl. Acad. Sci. USA* 89:251.
Yasuda, K. et al. (1992) *J. Biol Chem.* 267:20422.
Yasuda et al., (1993), *Proc. Natl. Acad. Sci. U.S.A.* 90:6736.
Yokota, Y. et al. (1992) *EMBO J.* 11:3585.
Zukin, R. S. et al. (1988) *Proc. Natl. Acad. Sci. USA* 85:4061.

---

What is claimed is:

1. An isolated and purified polynucleotide that encodes a mammalian kappa opioid receptor polypeptide wherein said polynucleotide encodes a mammalian kappa opioid receptor polypeptide comprising an amino acid residue sequence of SEQ ID NO:2 or SEQ ID NO:12.

2. The polynucleotide of claim 1, wherein said polynucleotide is a DNA molecule.

3. The polynucleotide of claim 1, wherein said polynucleotide is a RNA molecule.

4. The polynucleotide of claim 1, wherein said polynucleotide encodes a mammalian kappa opioid receptor polypeptide comprising the amino acid residue sequence of SEQ ID NO:2.

5. The polynucleotide of claim 4, wherein said polynucleotide comprises the nucleotide base sequence of SEQ ID NO:1.

6. The polynucleotide of claim 1, wherein said polynucleotide encodes a mammalian kappa opioid receptor polypeptide comprising the amino acid residue sequence of SEQ ID NO:12.

7. The polynucleotide of claim 6, wherein said polynucleotide comprises the nucleotide base sequence of SEQ ID NO:11.

8. An isolated and purified polynucleotide comprising a base sequence that is identical or complementary to a segment of at least 40 contiguous bases of SEQ ID NO:1, wherein said polynucleotide hybridizes under hybridization conditions employing between 0.02M and 0.15MNaCl at a temperature of between 50° C. to 70° C. to a polynucleotide that encodes a mammalian kappa opioid receptor polypeptide or to the complement of such a sequence.

9. The polynucleotide of claim 8, wherein said polynucleotide hybridizes to a polynucleotide that encodes mammalian kappa opioid receptor polypeptide comprising the amino acid residue sequence of SEQ ID NO:2 or to the complement of such a sequence.

10. The polynucleotide of claim 8, wherein said polynucleotide comprises a base sequence that is identical or complementary to a segment of at least 55 contiguous bases of SEQ ID NO:1.

11. The polynucleotide of claim 10, wherein said polynucleotide comprises a base sequence that is identical or complementary to a segment of at least 70 contiguous bases of SEQ ID NO:1.

12. The polynucleotide of claim 8, wherein said polynucleotide comprises a base sequence that is identical or complementary to a segment of at least 40 contiguous bases of SEQ ID NO:1.

13. An expression vector comprising a polynucleotide that encodes a mammalian kappa opioid receptor polypeptide comprising an amino acid residue sequence of SEQ ID NO:2 or SEQ ID NO:12.

14. The expression vector of claim 13, wherein said polynucleotide encodes a mammalian kappa opioid receptor polypeptide comprising the amino acid residue sequence of SEQ ID NO:2.

15. The expression vector of claim 14, wherein said polynucleotide comprises the nucleotide base sequence of SEQ ID NO:1.

16. The expression vector of claim 13, wherein said polynucleotide encodes a mammalian kappa opioid receptor polypeptide comprising the amino acid residue sequence of SEQ ID NO:12.

17. The expression vector of claim 16, wherein said polynucleotide comprises the nucleotide base sequence of SEQ ID NO:11.

18. The expression vector of claim 13, wherein said polynucleotide is operatively linked to an enhancer-promoter.

19. A recombinant host cell comprising a polynucleotide that encodes a mammalian kappa opioid receptor polypeptide comprising an amino acid residue sequence of SEQ ID NO:2 or SEQ ID NO:12.

20. The recombinant host cell of claim 19, comprising a polynucleotide that encodes a mammalian kappa opioid receptor polypeptide comprising the amino acid residue sequence of SEQ ID NO:2.

21. The recombinant host cell of claim 26, wherein said polynucleotide comprises the nucleotide base sequence of SEQ ID NO:1.

22. The recombinant host cell of claim 19, comprising a polynucleotide that encodes a mammalian kappa opioid receptor polypeptide comprising the amino acid residue sequence of SEQ ID NO:12.

23. The recombinant host cell of claim 22, wherein said polynucleotide comprises the nucleotide base sequence of SEQ ID NO:11.

24. The recombinant host cell of claim 19, wherein said polynucleotide is introduced into said cell by transformation of said cell with a vector comprising said polynucleotide.

25. The recombinant host cell of claim 19, wherein said host cell expresses said polynucleotide to produce the encoded mammalian kappa opioid receptor polypeptide.

26. The recombinant cell of claim 19, wherein said cell is a PC12 cell, a CHO cell or a COS cell.

27. The recombinant cell of claim 19, wherein said cell is an *E. coli* cell.

28. The recombinant cell of claim 19, wherein said cell is a yeast cell.

29. A process for preparing a cell expressing a mammalian kappa opioid receptor polypeptide comprising the steps of transfecting a cell with a polynucleotide that encodes a mammalian kappa opioid receptor polypeptide comprising an amino acid residue sequence of SEQ ID NO:2 or SEQ ID NO:12 to produce a transformed host cell; and (b) maintaining the transformed host cell under biological conditions sufficient for expression of said mammalian kappa opioid receptor polypeptide in the host cell.

30. The process of claim 29, further defined as a process for preparing cell expressing a mammalian kappa opioid receptor polypeptide comprising the amino acid residue sequence of SEQ ID NO:2.

31. The process of claim 29, further defined as a process for preparing cell expressing a mammalian kappa opioid receptor polypeptide comprising the amino acid residue sequence of SEQ ID NO:12.

* * * * *

UNITED STATES PATENT AND TRADEMARK OFFICE
CERTIFICATE OF CORRECTION

PATENT NO. : 6,096,513
DATED : August 1, 2000
INVENTOR(S) : Bell et al.

Page 1 of 1

It is certified that error appears in the above-identified patent and that said Letters Patent is hereby corrected as shown below:

Item [54],
Please delete "opiod" and insert -- opioid -- therefor.

Column 110, claim 21,
Line 12, please delete "claim 26" and insert -- claim 20 -- therefor.

Column 110, claim 29,
Line 38, please insert -- (a) -- before the phrase 'encoding a mammalian kappa opioid receptor'

Signed and Sealed this

Fifth Day of February, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,096,513
DATED         : August 1, 2000
INVENTOR(S)   : Bell et al.

It is certified that error appears in the above-identified patent and that said Letters Patent is hereby corrected as shown below:

<u>Title page, Item [54] and Column 1, line 2,</u>
Please delete "OPIOD" and insert -- OPIOID -- therefor.

<u>Column 110, claim 21,</u>
Line 12, please delete "claim 26" and insert -- claim 20 -- therefor.

<u>Column 110, claim 29,</u>
Line 38, please insert -- (a) -- before the phrase 'encodes a mammalian kappa opioid receptor'

This certificate supersedes Certificate of Correction issued February 5, 2002.

Signed and Sealed this

Twenty-second Day of April, 2003

JAMES E. ROGAN
*Director of the United States Patent and Trademark Office*

SEQUENCE LISTING (1) GENERAL INFORMATION:

(iii) NUMBER OF SEQUENCES:43

(2) INFORMATION FOR SEQ ID NO:1:

(i) SEQUENCE CHARACTERISTICS:
        (A) LENGTH: 1410 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 186..1325

(xi) SEQUENCE DESCRIPTION: SEQ ID NO:1:

```
GCGCACCTTG CTGATCCCAA ACAGGCAGAG CTTCTTCCAG TCTTGGAAGG CACAAATTGA      60

GCATCAGGAA CGTGGACCCA TCAGGGCTGA ACAGCTACTC AGGATCTAAA GTGGTGACTT     120

GGAAAGCTGA CGGTGACTTG GGAAGGGAGG TCGCCAATCA GCGATCTGGA GCTGCAGCGC     180

TCACC ATG GAG TCC CCC ATT CAG ATC TTC CGA GGA GAT CCA GGC CCT        227
      Met Glu Ser Pro Ile Gln Ile Phe Arg Gly Asp Pro Gly Pro
        1               5                  10

ACC TGC TCT CCC AGT GCT TGC CTT CTC CCC AAC AGC AGC TCT TGG TTC     275
Thr Cys Ser Pro Ser Ala Cys Leu Leu Pro Asn Ser Ser Ser Trp Phe
 15                  20                  25                  30

CCC AAC TGG GCA GAA TCC GAC AGT AAT GGC AGT GTG GGC TCA GAG GAT     323
Pro Asn Trp Ala Glu Ser Asp Ser Asn Gly Ser Val Gly Ser Glu Asp
                 35                  40                  45

CAG CAG CTG GAG TCC GCG CAC ATC TCT CCG GCC ATC CCT GTT ATC ATC     371
Gln Gln Leu Glu Ser Ala His Ile Ser Pro Ala Ile Pro Val Ile Ile
             50                  55                  60

ACC GCT GTC TAC TCT GTG GTA TTT GTG GTG GGC TTA GTG GGC AAT TCT     419
Thr Ala Val Tyr Ser Val Val Phe Val Val Gly Leu Val Gly Asn Ser
         65                  70                  75

CTG GTC ATG TTT GTC ATC ATC CGA TAC ACG AAG ATG AAG ACC GCA ACC     467
Leu Val Met Phe Val Ile Ile Arg Tyr Thr Lys Met Lys Thr Ala Thr
     80                  85                  90

AAC ATC TAC ATA TTT AAC CTG GCT TTG GCA GAT GCT TTG GTT ACT ACC     515
Asn Ile Tyr Ile Phe Asn Leu Ala Leu Ala Asp Ala Leu Val Thr Thr
 95                 100                 105                 110

ACT ATG CCC TTT CAG AGT GCT GTC TAC TTG ATG AAT TCT TGG CCT TTT     563
Thr Met Pro Phe Gln Ser Ala Val Tyr Leu Met Asn Ser Trp Pro Phe
                115                 120                 125

GGA GAT GTG CTA TGC AAG ATT GTC ATT TCC ATT GAC TAC TAC AAC ATG     611
Gly Asp Val Leu Cys Lys Ile Val Ile Ser Ile Asp Tyr Tyr Asn Met
            130                 135                 140

TTT ACC AGC ATA TTC ACC TTG ACC ATG ATG AGT GTG GAC CGC TAC ATT     659
Phe Thr Ser Ile Phe Thr Leu Thr Met Met Ser Val Asp Arg Tyr Ile
        145                 150                 155

GCT GTG TGC CAC CCT GTG AAA GCT TTG GAC TTC CGA ACA CCT TTG AAA     707
Ala Val Cys His Pro Val Lys Ala Leu Asp Phe Arg Thr Pro Leu Lys
```

```
      160                 165                 170
GCA AAG ATC ATC AAC ATC TGC ATT TGG CTC CTG GCA TCA TCT GTT GGT     755
Ala Lys Ile Ile Asn Ile Cys Ile Trp Leu Leu Ala Ser Ser Val Gly
175                 180                 185                 190

ATA TCA GCG ATA GTC CTT GGA GGC ACC AAA GTC AGG GAA GAT GTG GAT     803
Ile Ser Ala Ile Val Leu Gly Gly Thr Lys Val Arg Glu Asp Val Asp
                195                 200                 205

GTC ATT GAA TGC TCC TTG CAG TTT CCT GAT GAT GAA TAT TCC TGG TGG     851
Val Ile Glu Cys Ser Leu Gln Phe Pro Asp Asp Glu Tyr Ser Trp Trp
            210                 215                 220

GAT CTC TTC ATG AAG ATC TGT GTC TTC GTC TTT GCC TTT GTG ATC CCA     899
Asp Leu Phe Met Lys Ile Cys Val Phe Val Phe Ala Phe Val Ile Pro
        225                 230                 235

GTC CTC ATC ATC ATT GTC TGC TAC ACC CTG ATG ATC CTG CGC CTG AAG     947
Val Leu Ile Ile Ile Val Cys Tyr Thr Leu Met Ile Leu Arg Leu Lys
    240                 245                 250

AGT GTC CGG CTC CTG TCT GGC TCC CGA GAG AAG GAC CGA AAT CTC CGC     995
Ser Val Arg Leu Leu Ser Gly Ser Arg Glu Lys Asp Arg Asn Leu Arg
255                 260                 265                 270

CGC ATC ACC AAG CTG GTG CTG GTA GTA GTT GCA GTC TTC ATC ATC TGT    1043
Arg Ile Thr Lys Leu Val Leu Val Val Val Ala Val Phe Ile Ile Cys
                275                 280                 285

TGG ACC CCC ATT CAC ATC TTT ATC CTG GTG GAG GCT CTG GGA AGC ACC    1091
Trp Thr Pro Ile His Ile Phe Ile Leu Val Glu Ala Leu Gly Ser Thr
            290                 295                 300

TCC CAC AGC ACA GCT GCC CTC TCC AGC TAT TAT TTC TGT ATT GCC TTG    1139
Ser His Ser Thr Ala Ala Leu Ser Ser Tyr Tyr Phe Cys Ile Ala Leu
        305                 310                 315

GGT TAT ACC AAC AGC AGC CTG AAT CCT GTT CTC TAT GCC TTT CTG GAT    1187
Gly Tyr Thr Asn Ser Ser Leu Asn Pro Val Leu Tyr Ala Phe Leu Asp
    320                 325                 330

GAA AAC TTC AAG CGG TGT TTT AGG GAC TTC TGC TTC CCT ATT AAG ATG    1235
Glu Asn Phe Lys Arg Cys Phe Arg Asp Phe Cys Phe Pro Ile Lys Met
335                 340                 345                 350

CGA ATG GAG CGC CAG AGC ACC AAT AGA GTT AGA AAC ACA GTT CAG GAT    1283
Arg Met Glu Arg Gln Ser Thr Asn Arg Val Arg Asn Thr Val Gln Asp
                355                 360                 365

CCT GCT TCC ATG AGA GAT GTG GGA GGG ATG AAT AAG CCA GTA            1325
Pro Ala Ser Met Arg Asp Val Gly Gly Met Asn Lys Pro Val
            370                 375                 380

TGACTAGTCG TGGAAATGTC TTCTTATTGT TCTCCAGGTA GAGAAGAGTT CAATGATCTT  1385

GGTTTAACCC AGATTACAAC TGCAG                                        1410

(2) INFORMATION FOR SEQ ID NO:2:

(i) SEQUENCE CHARACTERISTICS:
        (A) LENGTH: 380 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Ser Pro Ile Gln Ile Phe Arg Gly Asp Pro Gly Pro Thr Cys
1               5                   10                  15

Ser Pro Ser Ala Cys Leu Leu Pro Asn Ser Ser Trp Phe Pro Asn
            20                  25                  30

Trp Ala Glu Ser Asp Ser Asn Gly Ser Val Gly Ser Glu Asp Gln Gln
            35                  40                  45
```

```
Leu Glu Ser Ala His Ile Ser Pro Ala Ile Pro Val Ile Ile Thr Ala
     50                  55                  60

Val Tyr Ser Val Val Phe Val Gly Leu Val Gly Asn Ser Leu Val
 65                  70                  75                  80

Met Phe Val Ile Ile Arg Tyr Thr Lys Met Lys Thr Ala Thr Asn Ile
                 85                  90                  95

Tyr Ile Phe Asn Leu Ala Leu Ala Asp Ala Leu Val Thr Thr Thr Met
            100                 105                 110

Pro Phe Gln Ser Ala Val Tyr Leu Met Asn Ser Trp Pro Phe Gly Asp
            115                 120                 125

Val Leu Cys Lys Ile Val Ile Ser Ile Asp Tyr Tyr Asn Met Phe Thr
            130                 135                 140

Ser Ile Phe Thr Leu Thr Met Met Ser Val Asp Arg Tyr Ile Ala Val
145                 150                 155                 160

Cys His Pro Val Lys Ala Leu Asp Phe Arg Thr Pro Leu Lys Ala Lys
                165                 170                 175

Ile Ile Asn Ile Cys Ile Trp Leu Leu Ala Ser Ser Val Gly Ile Ser
            180                 185                 190

Ala Ile Val Leu Gly Gly Thr Lys Val Arg Glu Asp Val Asp Val Ile
            195                 200                 205

Glu Cys Ser Leu Gln Phe Pro Asp Asp Glu Tyr Ser Trp Trp Asp Leu
            210                 215                 220

Phe Met Lys Ile Cys Val Phe Val Phe Ala Phe Val Ile Pro Val Leu
225                 230                 235                 240

Ile Ile Ile Val Cys Tyr Thr Leu Met Ile Leu Arg Leu Lys Ser Val
                245                 250                 255

Arg Leu Leu Ser Gly Ser Arg Glu Lys Asp Arg Asn Leu Arg Arg Ile
            260                 265                 270

Thr Lys Leu Val Leu Val Val Val Ala Val Phe Ile Ile Cys Trp Thr
            275                 280                 285

Pro Ile His Ile Phe Ile Leu Val Glu Ala Leu Gly Ser Thr Ser His
            290                 295                 300

Ser Thr Ala Ala Leu Ser Ser Tyr Tyr Phe Cys Ile Ala Leu Gly Tyr
305                 310                 315                 320

Thr Asn Ser Ser Leu Asn Pro Val Leu Tyr Ala Phe Leu Asp Glu Asn
                325                 330                 335

Phe Lys Arg Cys Phe Arg Asp Phe Cys Phe Pro Ile Lys Met Arg Met
            340                 345                 350

Glu Arg Gln Ser Thr Asn Arg Val Arg Asn Thr Val Gln Asp Pro Ala
            355                 360                 365

Ser Met Arg Asp Val Gly Gly Met Asn Lys Pro Val
            370                 375                 380

(2) INFORMATION FOR SEQ ID NO:3:

(i) SEQUENCE CHARACTERISTICS:
        (A) LENGTH: 2272 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 12..1127

(xi) SEQUENCE DESCRIPTION: SEQ ID NO:3:
```

```
CACGCGGCGC C ATG GAG CTG GTG CCC TCT GCC CGT GCG GAG CTG CAG TCC     50
            Met Glu Leu Val Pro Ser Ala Arg Ala Glu Leu Gln Ser
             1               5                  10

TCG CCC CTC GTC AAC CTC TCG GAC GCC TTT CCC AGC GCC TTC CCC AGC     98
Ser Pro Leu Val Asn Leu Ser Asp Ala Phe Pro Ser Ala Phe Pro Ser
     15              20                  25

GCG GGC GCC AAT GCG TCG GGG TCG CCG GGA GCC CGT AGT GCC TCG TCC    146
Ala Gly Ala Asn Ala Ser Gly Ser Pro Gly Ala Arg Ser Ala Ser Ser
 30              35                  40                      45

CTC GCC CTA GCC ATC GCC ATC ACC GCG CTC TAC TCG GCT GTG TGC GCA    194
Leu Ala Leu Ala Ile Ala Ile Thr Ala Leu Tyr Ser Ala Val Cys Ala
                 50                  55                  60

GTG GGG CTT CTG GGC AAC GTG CTC GTC ATG TTT GGC ATC GTC CGG TAC    242
Val Gly Leu Leu Gly Asn Val Leu Val Met Phe Gly Ile Val Arg Tyr
             65                  70                  75

ACC AAA TTG AAG ACC GCC ACC AAC ATC TAC ATC TTC AAT CTG GCT TTG    290
Thr Lys Leu Lys Thr Ala Thr Asn Ile Tyr Ile Phe Asn Leu Ala Leu
         80                  85                  90

GCT GAT GCG CTG GCC ACC AGC ACG CTG CCC TTC CAG AGC GCC AAG TAC    338
Ala Asp Ala Leu Ala Thr Ser Thr Leu Pro Phe Gln Ser Ala Lys Tyr
     95                  100                 105

TTG ATG GAA ACG TGG CCG TTT GGC GAG CTG CTG TGC AAG GCT GTG CTC    386
Leu Met Glu Thr Trp Pro Phe Gly Glu Leu Leu Cys Lys Ala Val Leu
110             115                 120                     125

TCC ATT GAC TAC TAC AAC ATG TTC ACT AGC ATC TTC ACC CTC ACC ATG    434
Ser Ile Asp Tyr Tyr Asn Met Phe Thr Ser Ile Phe Thr Leu Thr Met
                 130                 135                 140

ATG AGC GTG GAC CGC TAC ATT GCT GTC TGC CAT CCT GTC AAA GCC CTG    482
Met Ser Val Asp Arg Tyr Ile Ala Val Cys His Pro Val Lys Ala Leu
             145                 150                 155

GAC TTC CGG ACA CCA GCC AAG GCC AAG CTG ATC AAT ATA TGC ATC TGG    530
Asp Phe Arg Thr Pro Ala Lys Ala Lys Leu Ile Asn Ile Cys Ile Trp
         160                 165                 170

GTC TTG GCT TCA GGT GTC GGG GTC CCC ATC ATG GTC ATG GCA GTG ACC    578
Val Leu Ala Ser Gly Val Gly Val Pro Ile Met Val Met Ala Val Thr
     175                 180                 185

CAA CCC CGG GAT GGT GCA GTG GTA TGC ATG CTC CAG TTC CCC AGT CCC    626
Gln Pro Arg Asp Gly Ala Val Val Cys Met Leu Gln Phe Pro Ser Pro
190             195                 200                     205

AGC TGG TAC TGG GAC ACT GTG ACC AAG ATC TGC GTG TTC CTC TTT GCC    674
Ser Trp Tyr Trp Asp Thr Val Thr Lys Ile Cys Val Phe Leu Phe Ala
                 210                 215                 220

TTC GTG GTG CCG ATC CTC ATC ATC ACG GTG TGC TAT GGC CTC ATG CTA    722
Phe Val Val Pro Ile Leu Ile Ile Thr Val Cys Tyr Gly Leu Met Leu
             225                 230                 235

CTG CGC CTG CGC AGC GTG CGT CTG CTG TCC GGT TCC AAG GAG AAG GAC    770
Leu Arg Leu Arg Ser Val Arg Leu Leu Ser Gly Ser Lys Glu Lys Asp
         240                 245                 250

CGC AGC CTG CGG CGC ATC ACG CGC ATG GTG CTG GTG GTG GTG GGC GCC    818
Arg Ser Leu Arg Arg Ile Thr Arg Met Val Leu Val Val Val Gly Ala
     255                 260                 265

TTC GTG GTG TGC TGG GCG CCC ATC CAC ATC TTC GTC ATC GTC TGG ACG    866
Phe Val Val Cys Trp Ala Pro Ile His Ile Phe Val Ile Val Trp Thr
270             275                 280                     285

CTG GTG GAC ATC AAT CGG CGC GAC CCA CTT GTG GTG GCC GCA CTG CAC    914
Leu Val Asp Ile Asn Arg Arg Asp Pro Leu Val Val Ala Ala Leu His
                 290                 295                 300

CTG TGC ATT GCG CTG GGC TAC GCC AAC AGC AGC CTC AAC CCG GTT CTC    962
Leu Cys Ile Ala Leu Gly Tyr Ala Asn Ser Ser Leu Asn Pro Val Leu
```

-continued

```
                   305                 310                 315
TAC GCC TTC CTG GAC GAG AAC TTC AAG CGC TGC TTC CGC CAG CTC TGT      1010
Tyr Ala Phe Leu Asp Glu Asn Phe Lys Arg Cys Phe Arg Gln Leu Cys
            320                 325                 330

CGC ACG CCC TGC GGC CGC CAA GAA CCC GGC AGT CTC CGT CGT CCC CGC      1058
Arg Thr Pro Cys Gly Arg Gln Glu Pro Gly Ser Leu Arg Arg Pro Arg
            335                 340                 345

CAG GCC ACC ACG CGT GAG CGT GTC ACT GCC TGC ACC CCC TCC GAC GGC      1106
Gln Ala Thr Thr Arg Glu Arg Val Thr Ala Cys Thr Pro Ser Asp Gly
350                 355                 360                 365

CCG GGC GGT GGC GCT GCC GCC TGACCTACCC GACCTTCCCC TTAAACGCCC          1157
Pro Gly Gly Gly Ala Ala Ala
                370

CTCCCAAGTG AAGTGATCCA GAGGCCACAC CGAGCTCCCT GGGAGGCTGT GGCCACCACC     1217

AGGACAGCTA GAATTGGGCC TGCACAGAGG GGAGGCCTCC TGTGGGGACG GGGCCTGAGG     1277

GATCAAAGGC TCCAGGTTGG AACGGTGGGG GTGAGGAAGC AGAGCTGGTG ATTCCTAAAC     1337

TGTATCCATT AGTAAGGCCT CTCCAATGGG ACAGAGCCTC CGCCTTGAGA TAACATCGGG     1397

TTCTGGCCAA AAAGAACACC AGCTCCAGTC CAAGACCCAA GGATTCCAGC TCCAGGAACC     1457

AGGAGGGGTC GATGATTTGG TTTGGCTGAG AGTCCCAGCA TTTGTGTTAT GGGGAGGATC     1517

TCTCATCTTA GAGAAGATAA GGGGACAGGG CATTCAGGCA AGGCAGCTTG GGGTTTGGTC     1577

AGGAGATAAG CGCCCCCTTC CCTTGGGGGG AGGATAAGTG GGGGATGGTC AACGTTGGAG     1637

AAGAGTCAAA GTTCTCACCA CCTTTCTAAC TACTCAGCTA AACTCGTTGA GGCTAGGGCA     1697

ACGTGACTTC TCTGTAGAGA GGATACAAGC CGGGCCTGAT GGGGCAGGCT GTGTAATCCC     1757

AGTCATAGTG GAGGCTGAGG CTGGAAAATT AAGGACCAAC AGCCTGGGCA ATTTAGTGTC     1817

TCAAAATAAA ATGTAAAGAG GGCTGGGAAT GTAGCTCAGT GGTAGGGTGT TTGTGTGAGG     1877

CTCTGGGATC AATAAGACAA AACAACCAAC CAACCAAAAA CCTTCCAAAC AACAAAACCA     1937

ACCCTCAAAC CAAAAAACTA TGTGGGTGTC TCTGAGTCTG GTTTGAAGAG AACCCGCAGC     1997

CCTGTATCCC TGTGGGGCTG TGGACAGTGG GCAGAAGCAG AGGCTCCCTG GATCCTGAAC     2057

AAGGGCCCCA AAAGCAAGTT CTAAAGGGAC CCCTGAAACC GAGTAAGCCT TTGTGTCAAG     2117

AAGTGGGAGT AGAACCAGAA AGGTGGCTGA GTGATTAAGG GCACGTGACT CTCTTGCAGA     2177

GGACATAGGT TCGATTCCCA GCACCCACAT AGTGGCTCAC AGCCATCTGT AACCCCAGTC     2237

GCAGTCAATC TAATGCTTTC CAACAACTGT GGGCA                                2272

(2) INFORMATION FOR SEQ ID NO:4:

(i) SEQUENCE CHARACTERISTICS:
        (A) LENGTH: 372 amino acids
        (B) TYPE: amino acid
        (D) TOPOLOGY: linear (ii) MOLECULE TYPE: protein (xi) SEQUENCE DESCRIPTION: SEQ ID NO:4:

Met Glu Leu Val Pro Ser Ala Arg Ala Glu Leu Gln Ser Ser Pro Leu
 1               5                  10                  15

Val Asn Leu Ser Asp Ala Phe Pro Ser Ala Phe Pro Ser Ala Gly Ala
            20                  25                  30

Asn Ala Ser Gly Ser Pro Gly Ala Arg Ser Ala Ser Ser Leu Ala Leu
        35                  40                  45

Ala Ile Ala Ile Thr Ala Leu Tyr Ser Ala Val Cys Ala Val Gly Leu
    50                  55                  60
```

```
Leu Gly Asn Val Leu Val Met Phe Gly Ile Val Arg Tyr Thr Lys Leu
 65                  70                  75                  80

Lys Thr Ala Thr Asn Ile Tyr Ile Phe Asn Leu Ala Leu Ala Asp Ala
                 85                  90                  95

Leu Ala Thr Ser Thr Leu Pro Phe Gln Ser Ala Lys Tyr Leu Met Glu
            100                 105                 110

Thr Trp Pro Phe Gly Glu Leu Leu Cys Lys Ala Val Leu Ser Ile Asp
        115                 120                 125

Tyr Tyr Asn Met Phe Thr Ser Ile Phe Thr Leu Thr Met Met Ser Val
130                 135                 140

Asp Arg Tyr Ile Ala Val Cys His Pro Val Lys Ala Leu Asp Phe Arg
145                 150                 155                 160

Thr Pro Ala Lys Ala Lys Leu Ile Asn Ile Cys Ile Trp Val Leu Ala
                165                 170                 175

Ser Gly Val Gly Val Pro Ile Met Val Met Ala Val Thr Gln Pro Arg
            180                 185                 190

Asp Gly Ala Val Val Cys Met Leu Gln Phe Pro Ser Pro Ser Trp Tyr
        195                 200                 205

Trp Asp Thr Val Thr Lys Ile Cys Val Phe Leu Phe Ala Phe Val Val
210                 215                 220

Pro Ile Leu Ile Ile Thr Val Cys Tyr Gly Leu Met Leu Leu Arg Leu
225                 230                 235                 240

Arg Ser Val Arg Leu Leu Ser Gly Ser Lys Glu Lys Asp Arg Ser Leu
                245                 250                 255

Arg Arg Ile Thr Arg Met Val Leu Val Val Gly Ala Phe Val Val
            260                 265                 270

Cys Trp Ala Pro Ile His Ile Phe Val Ile Val Trp Thr Leu Val Asp
        275                 280                 285

Ile Asn Arg Arg Asp Pro Leu Val Val Ala Ala Leu His Leu Cys Ile
290                 295                 300

Ala Leu Gly Tyr Ala Asn Ser Ser Leu Asn Pro Val Leu Tyr Ala Phe
305                 310                 315                 320

Leu Asp Glu Asn Phe Lys Arg Cys Phe Arg Gln Leu Cys Arg Thr Pro
                325                 330                 335

Cys Gly Arg Gln Glu Pro Gly Ser Leu Arg Arg Pro Arg Gln Ala Thr
            340                 345                 350

Thr Arg Glu Arg Val Thr Ala Cys Thr Pro Ser Asp Gly Pro Gly Gly
        355                 360                 365

Gly Ala Ala Ala
370

(2) INFORMATION FOR SEQ ID NO:5:

(i) SEQUENCE CHARACTERISTICS:
        (A) LENGTH: 1330 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 161..1261

(xi) SEQUENCE DESCRIPTION: SEQ ID NO:5:

AGCCGGAGCA GACCCCAAGC TAGAGTGAGA AGCATTACTC AGTTCATTGT GCTCCTGCCT      60
```

-continued

```
GCCTTTCTGC TAAGCATTAG GGTCTGTTTT GGCCCAGCTT CTGAAGAGGT TGTGTGTGCT       120

GTTGGAGGAA CTGTACTGAG TGGCTTTGCA GGGTGACAGC ATG GAG TCC CTC TTT         175
                                            Met Glu Ser Leu Phe
                                            1                 5

CCT GCC CCA TTC TGG GAG GTC TTG TAT GGC AGC CAC TTT CAA GGG AAC         223
Pro Ala Pro Phe Trp Glu Val Leu Tyr Gly Ser His Phe Gln Gly Asn
            10              15                  20

CTG TCT CTC CTA AAT GAG ACC GTA CCC CAT CAC CTG CTC CTC AAT GCT         271
Leu Ser Leu Leu Asn Glu Thr Val Pro His His Leu Leu Leu Asn Ala
            25              30                  35

AGC CAC AGT GCC TTC CTG CCC CTT GGA CTC AAG GTC ACC ATC GTG GGG         319
Ser His Ser Ala Phe Leu Pro Leu Gly Leu Lys Val Thr Ile Val Gly
            40              45                  50

CTC TAC TTG GCT GTG TGC ATC GGG GGG CTC CTG GGG AAC TGC CTC GTC         367
Leu Tyr Leu Ala Val Cys Ile Gly Gly Leu Leu Gly Asn Cys Leu Val
            55              60                  65

ATG TAT GTC ATC CTC AGG CAC ACC AAG ATG AAG ACT GCT ACC AAC ATT         415
Met Tyr Val Ile Leu Arg His Thr Lys Met Lys Thr Ala Thr Asn Ile
70              75              80                  85

TAC ATA TTT AAT CTG GCA CTG GCT GAT ACC CTG GTC TTG CTG ACA CTG         463
Tyr Ile Phe Asn Leu Ala Leu Ala Asp Thr Leu Val Leu Leu Thr Leu
            90              95                  100

CCC TTC CAG GGC ACA GAC ATC CTT CTG GGC TTC TGG CCA TTT GGG AAT         511
Pro Phe Gln Gly Thr Asp Ile Leu Leu Gly Phe Trp Pro Phe Gly Asn
            105             110                 115

GCA CTG TGC AAG ACG GTC ATT GCT ATC GAC TAC TAC AAC ATG TTT ACC         559
Ala Leu Cys Lys Thr Val Ile Ala Ile Asp Tyr Tyr Asn Met Phe Thr
            120             125                 130

AGC ACT TTC ACT TTG ACT GCC ATG AGT GTA GAC CGT TAT GTA GCT ATC         607
Ser Thr Phe Thr Leu Thr Ala Met Ser Val Asp Arg Tyr Val Ala Ile
135             140                 145

TGC CAC CCT ATC CGT GCC CTT GAT GTT CGG ACA TCC AGT AAA GCC CAG         655
Cys His Pro Ile Arg Ala Leu Asp Val Arg Thr Ser Ser Lys Ala Gln
150             155             160                 165

GCC GTT AAT GTG GCC ATA TGG GCC CTG GCT TCG GTG GTT GGT GTT CCT         703
Ala Val Asn Val Ala Ile Trp Ala Leu Ala Ser Val Val Gly Val Pro
            170             175                 180

GTT GCC ATC ATG GGC TCA GCA CAA GTG GAG GAT GAA GAG ATC GAG TGC         751
Val Ala Ile Met Gly Ser Ala Gln Val Glu Asp Glu Glu Ile Glu Cys
            185             190                 195

CTG GTG GAG ATC CCC GCC CCT CAG GAC TAT TGG GGC CCT GTA TTT GCC         799
Leu Val Glu Ile Pro Ala Pro Gln Asp Tyr Trp Gly Pro Val Phe Ala
            200             205                 210

ATC TGC ATC TTC CTT TTT TCC TTC ATC ATC CCG GTT CTG ATC ATC TCT         847
Ile Cys Ile Phe Leu Phe Ser Phe Ile Ile Pro Val Leu Ile Ile Ser
215             220                 225

GTC TGC TAC AGC CTC ATG ATT CGA CGA CTT CGT GGT GTC CGG CTG CTT         895
Val Cys Tyr Ser Leu Met Ile Arg Arg Leu Arg Gly Val Arg Leu Leu
230             235             240                 245

TCA GGC TCC CGA GAG AAG GAC CGG AAC CTG CGA CGC ATC ACA CGG CTG         943
Ser Gly Ser Arg Glu Lys Asp Arg Asn Leu Arg Arg Ile Thr Arg Leu
            250             255                 260

GTA CTG GTA GTT GTG GCT GTG TTT GTG GGC TGC TGG ACA CCT GTG CAG         991
Val Leu Val Val Val Ala Val Phe Val Gly Cys Trp Thr Pro Val Gln
            265             270                 275

GTC TTT GTC CTG GTT CAA GGA CTG GGT GTT CAG CCA GGT AGT GAG ACT         1039
Val Phe Val Leu Val Gln Gly Leu Gly Val Gln Pro Gly Ser Glu Thr
            280             285                 290
```

```
GCA GTA GCC ATT CTG CGC TTC TGC ACA GCC CTG GGC TAT GTC AAC AGT       1087
Ala Val Ala Ile Leu Arg Phe Cys Thr Ala Leu Gly Tyr Val Asn Ser
    295                 300                 305

TGT CTC AAT CCC ATT CTC TAT GCT TTC TTG GAT GAG AAC TTC AAG GCC       1135
Cys Leu Asn Pro Ile Leu Tyr Ala Phe Leu Asp Glu Asn Phe Lys Ala
310                 315                 320                 325

TGC TTT AGA AAG TTC TGC TGT GCT TCT GCC CTG CAC CGG GAG ATG CAG       1183
Cys Phe Arg Lys Phe Cys Cys Ala Ser Ala Leu His Arg Glu Met Gln
            330                 335                 340

GTT TCT GAT CGT GTG CGC AGC ATT GCC AAG GAT GTA GGC CTT GGT TGC       1231
Val Ser Asp Arg Val Arg Ser Ile Ala Lys Asp Val Gly Leu Gly Cys
                345                 350                 355

AAG ACC TCT GAG ACA GTA CCA CGG CCG GCA TGACTAGGCG TGGACCTGCC         1281
Lys Thr Ser Glu Thr Val Pro Arg Pro Ala
                360                 365

CATGGTGCCT GTCAGTCCAC AGAGCCCATC TACACCCAAC ACGGAGCTC                 1330

(2) INFORMATION FOR SEQ ID NO:6:

(i) SEQUENCE CHARACTERISTICS:
        (A) LENGTH: 367 amino acids
        (B) TYPE: amino acid
        (D) TOPOLOGY: linear (ii) MOLECULE TYPE: protein (xi) SEQUENCE DESCRIPTION: SEQ ID NO:6:

Met Glu Ser Leu Phe Pro Ala Pro Phe Trp Glu Val Leu Tyr Gly Ser
 1               5                  10                  15

His Phe Gln Gly Asn Leu Ser Leu Leu Asn Glu Thr Val Pro His His
                20                  25                  30

Leu Leu Leu Asn Ala Ser His Ser Ala Phe Leu Pro Leu Gly Leu Lys
            35                  40                  45

Val Thr Ile Val Gly Leu Tyr Leu Ala Val Cys Ile Gly Gly Leu Leu
        50                  55                  60

Gly Asn Cys Leu Val Met Tyr Val Ile Leu Arg His Thr Lys Met Lys
65                  70                  75                  80

Thr Ala Thr Asn Ile Tyr Ile Phe Asn Leu Ala Leu Ala Asp Thr Leu
                85                  90                  95

Val Leu Leu Thr Leu Pro Phe Gln Gly Thr Asp Ile Leu Leu Gly Phe
            100                 105                 110

Trp Pro Phe Gly Asn Ala Leu Cys Lys Thr Val Ile Ala Ile Asp Tyr
        115                 120                 125

Tyr Asn Met Phe Thr Ser Thr Phe Thr Leu Thr Ala Met Ser Val Asp
    130                 135                 140

Arg Tyr Val Ala Ile Cys His Pro Ile Arg Ala Leu Asp Val Arg Thr
145                 150                 155                 160

Ser Ser Lys Ala Gln Ala Val Asn Val Ala Ile Trp Ala Leu Ala Ser
                165                 170                 175

Val Val Gly Val Pro Val Ala Ile Met Gly Ser Ala Gln Val Glu Asp
            180                 185                 190

Glu Glu Ile Glu Cys Leu Val Glu Ile Pro Ala Pro Gln Asp Tyr Trp
        195                 200                 205

Gly Pro Val Phe Ala Ile Cys Ile Phe Leu Phe Ser Phe Ile Ile Pro
    210                 215                 220

Val Leu Ile Ile Ser Val Cys Tyr Ser Leu Met Ile Arg Arg Leu Arg
225                 230                 235                 240
```

```
Gly Val Arg Leu Leu Ser Gly Ser Arg Glu Lys Asp Arg Asn Leu Arg
                245                 250                 255

Arg Ile Thr Arg Leu Val Leu Val Val Ala Val Phe Val Gly Cys
            260                 265                 270

Trp Thr Pro Val Gln Val Phe Val Leu Val Gln Gly Leu Gly Val Gln
            275                 280                 285

Pro Gly Ser Glu Thr Ala Val Ala Ile Leu Arg Phe Cys Thr Ala Leu
            290                 295                 300

Gly Tyr Val Asn Ser Cys Leu Asn Pro Ile Leu Tyr Ala Phe Leu Asp
305                 310                 315                 320

Glu Asn Phe Lys Ala Cys Phe Arg Lys Phe Cys Cys Ala Ser Ala Leu
                325                 330                 335

His Arg Glu Met Gln Val Ser Asp Arg Val Arg Ser Ile Ala Lys Asp
                340                 345                 350

Val Gly Leu Gly Cys Lys Thr Ser Glu Thr Val Pro Arg Pro Ala
            355                 360                 365
```

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

GTGGGCAATT CACTAGTCAT GTTT                                      24

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

CTGGGCAACG TACTAGTCAT GTTT                                      24

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Y
        (B) LOCATION: 6, 12, 15, and 18
        (C) IDENTIFICATION METHOD: Y = T or C (ix) FEATURE:
        (A) NAME/KEY: R
        (B) LOCATION: 7
        (C) IDENTIFICATION METHOD: R = G or A (ix) FEATURE:
        (A) NAME/KEY: N
        (B) LOCATION: 21
        (C) IDENTIFICATION METHOD: N = Inosine (xi) SEQUENCE DESCRIPTION: SEQ ID NO:9:

ACCAAYRTCT AYATYATYCT NAACCTGGC                                                29

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY:  N
        (B) LOCATION:  3
        (C) IDENTIFICATION METHOD:  N  =  Inosine (ix) FEATURE:
        (A) NAME/KEY:  R
        (B) LOCATION:  9 and 18
        (C) IDENTIFICATION METHOD:  R  =  G or A (ix) FEATURE:
        (A) NAME/KEY:  W
        (B) LOCATION:  13
        (C) IDENTIFICATION METHOD:  W  =  A or T (ix) FEATURE:
        (A) NAME/KEY:  K
        (B) LOCATION:  15
        (C) IDENTIFICATION METHOD:  K  =  G or T (xi) SEQUENCE DESCRIPTION: SEQ ID NO:10:

ACNGTCAGRC AGWAKATRCT GGTGAA                                                   26

(2) INFORMATION FOR SEQ ID NO:11:

(i) SEQUENCE CHARACTERISTICS:
        (A) LENGTH:  1000 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY:  N
        (B) LOCATION:  607-608, 642-643, 896, 906
        (C) IDENTIFICATION METHOD:  N = A, C, G or T (ix) FEATURE:
        (A) NAME/KEY: CDS
        (B) LOCATION: 102..986

(ix) FEATURE:
        (A) NAME/KEY: Xaa
        (B) LOCATION: 169, 181, 265, 269
        (C) IDENTIFICATION METHOD: Xaa = unknown (xi) SEQUENCE DESCRIPTION: SEQ ID NO:11:

AAGAAGCAAA ATCAGTAATC CAAAGGCTAT CACAAACACA TTCACCTTAT GGGGTTTGAC        60

TTGAAAATGG AGGGAAATGC TATTGTTTCT TTTCTTTTAG A TAC ACA AAG ATG AAG       116
                                             Tyr Thr Lys Met Lys
                                                                 5

ACA GCA ACC AAC ATT TAC ATA TTT AAC CTG GCT TTG GCA GAT GCT TTA         164
Thr Ala Thr Asn Ile Tyr Ile Phe Asn Leu Ala Leu Ala Asp Ala Leu
             10                  15                  20

GTT ACT ACA ACC ATG CCC TTT CAG AGT ACG GTC TAC TTG ATG AAT TCC         212
Val Thr Thr Thr Met Pro Phe Gln Ser Thr Val Tyr Leu Met Asn Ser

|  |  |  |  |  |  |  |  |  |  |  |  |  |
|---|---|---|---|---|---|---|---|---|---|---|---|---|
|  |  | 25 |  |  |  | 30 |  |  |  | 35 |  |  |

```
TGG CCT TTT GGG GAT GTG CTG TGC AAG ATA GTA ATT TCC ATT GAT TAC      260
Trp Pro Phe Gly Asp Val Leu Cys Lys Ile Val Ile Ser Ile Asp Tyr
        40                  45                  50

TAC AAC ATG TTC ACC AGC ATC TTC ACC TTG ACC ATG ATG AGC GTG GAC      308
Tyr Asn Met Phe Thr Ser Ile Phe Thr Leu Thr Met Met Ser Val Asp
    55                  60                  65

CGC TAC ATT GCC GTG TGC CAC CCC GTG AAG GCT TTG GAC TTC CGC ACA      356
Arg Tyr Ile Ala Val Cys His Pro Val Lys Ala Leu Asp Phe Arg Thr
70                  75                  80                  85

CCC TTG AAG GCA AAG ATC ATC AAT ATC TGC ATC TGG CTG CTG TCG TCA      404
Pro Leu Lys Ala Lys Ile Ile Asn Ile Cys Ile Trp Leu Leu Ser Ser
            90                  95                  100

TCT GTT GGC ATC TCT GCA ATA GTC CTT GGA GGC ACC AAA GTC AGG GAA      452
Ser Val Gly Ile Ser Ala Ile Val Leu Gly Gly Thr Lys Val Arg Glu
                105                 110                 115

GGT GTC GAT GTC ATT GAG TGC TGC TTG CAG TTC CCA GAT GAT GAC TAC      500
Gly Val Asp Val Ile Glu Cys Cys Leu Gln Phe Pro Asp Asp Asp Tyr
        120                 125                 130

TCC TGG TGG GAC CTC TTC ATG AAG ATC TGC GTC TTC ATC TTT GCC TTC      548
Ser Trp Trp Asp Leu Phe Met Lys Ile Cys Val Phe Ile Phe Ala Phe
    135                 140                 145

GTG ATC CCT GTC CTC ATC ATC GTC TGC TAC ACC CTG ATG ATC CTG           596
Val Ile Pro Val Leu Ile Ile Val Cys Tyr Thr Leu Met Ile Leu
150                 155                 160                 165

CGT CTC AAG ANN GTC CGG CTC CTT TCT GGC TCC CGA GAG AAA GAT NNC      644
Arg Leu Lys Xaa Val Arg Leu Leu Ser Gly Ser Arg Glu Lys Asp Xaa
            170                 175                 180

AAC CTG CGT AGG ATC ACC AGA CTG GTC CTG GTG GTG GTG GCA GTC TTC      692
Asn Leu Arg Arg Ile Thr Arg Leu Val Leu Val Val Val Ala Val Phe
                185                 190                 195

GTC GTC TGC TGG ACT CCC ATT CAC ATA TTC ATC CTG GTG GAG GCT CTG      740
Val Val Cys Trp Thr Pro Ile His Ile Phe Ile Leu Val Glu Ala Leu
        200                 205                 210

GGG AGC ACC TCC CAC AGC ACA GCT GCT CTC TCC AGC TAT TAC TTC TGC      788
Gly Ser Thr Ser His Ser Thr Ala Ala Leu Ser Ser Tyr Tyr Phe Cys
    215                 220                 225

ATC GCC TTA GGC TAT ACC AAC AGT AGC CTG AAT CCC ATT CTC TAC GCC      836
Ile Ala Leu Gly Tyr Thr Asn Ser Ser Leu Asn Pro Ile Leu Tyr Ala
230                 235                 240                 245

TTT CTT GAT GAA AAC TTC AAG CGG TGT TTC CGG GAC TTC TGC TTT CCA      884
Phe Leu Asp Glu Asn Phe Lys Arg Cys Phe Arg Asp Phe Cys Phe Pro
                250                 255                 260

CTG AAG ATG AGN ATG GAG CGC NAG AGC ACT AGC AGA GTC CGA AAT ACA      932
Leu Lys Met Xaa Met Glu Arg Xaa Ser Thr Ser Arg Val Arg Asn Thr
            265                 270                 275

GTT CAG GAT CCT GCT TAC CTG AGG GAG ATC GAT GGG ATG ATG AAT AAA      980
Val Gln Asp Pro Ala Tyr Leu Arg Glu Ile Asp Gly Met Met Asn Lys
                280                 285                 290

CCA GTA TGACTAGTCG TGGA                                             1000
Pro Val
    295
```

(2) INFORMATION FOR SEQ ID NO:12:

(i) SEQUENCE CHARACTERISTICS:
        (A) LENGTH: 295 amino acids
        (B) TYPE: amino acid
        (D) TOPOLOGY: linear (ii) MOLECULE TYPE: protein (ix) FEATURE:
    (A) NAME/KEY: Xaa
    (B) LOCATION: 169, 181, 265, 269
    (C) IDENTIFICATION METHOD: Xaa = unknown (xi) SEQUENCE DESCRIPTION: SEQ ID NO:12:

```
Tyr Thr Lys Met Lys Thr Ala Thr Asn Ile Tyr Ile Phe Asn Leu Ala
                 5                  10                  15

Leu Ala Asp Ala Leu Val Thr Thr Thr Met Pro Phe Gln Ser Thr Val
             20                  25                  30

Tyr Leu Met Asn Ser Trp Pro Phe Gly Asp Val Leu Cys Lys Ile Val
         35                  40                  45

Ile Ser Ile Asp Tyr Tyr Asn Met Phe Thr Ser Ile Phe Thr Leu Thr
     50                  55                  60

Met Met Ser Val Asp Arg Tyr Ile Ala Val Cys His Pro Val Lys Ala
 65                  70                  75                  80

Leu Asp Phe Arg Thr Pro Leu Lys Ala Lys Ile Ile Asn Ile Cys Ile
                 85                  90                  95

Trp Leu Leu Ser Ser Ser Val Gly Ile Ser Ala Ile Val Leu Gly Gly
            100                 105                 110

Thr Lys Val Arg Glu Asp Val Asp Val Ile Glu Cys Cys Leu Gln Phe
        115                 120                 125

Pro Asp Asp Asp Tyr Ser Trp Trp Asp Leu Phe Met Lys Ile Cys Val
130                 135                 140

Phe Ile Phe Ala Phe Val Ile Pro Val Leu Ile Ile Val Cys Tyr
145                 150                 155                 160

Thr Leu Met Ile Leu Arg Leu Lys Xaa Val Arg Leu Leu Ser Gly Ser
            165                 170                 175

Arg Glu Lys Asp Xaa Asn Leu Arg Arg Ile Thr Arg Leu Val Leu Val
            180                 185                 190

Val Val Ala Val Phe Val Val Cys Trp Thr Pro Ile His Ile Phe Ile
        195                 200                 205

Leu Val Glu Ala Leu Gly Ser Thr Ser His Ser Thr Ala Ala Leu Ser
210                 215                 220

Ser Tyr Tyr Phe Cys Ile Ala Leu Gly Tyr Thr Asn Ser Ser Leu Asn
225                 230                 235                 240

Pro Ile Leu Tyr Ala Phe Leu Asp Glu Asn Phe Lys Arg Cys Phe Arg
            245                 250                 255

Asp Phe Cys Phe Pro Leu Lys Met Xaa Met Glu Arg Xaa Ser Thr Ser
            260                 265                 270

Arg Val Arg Asn Thr Val Gln Asp Pro Ala Tyr Leu Arg Glu Ile Asp
        275                 280                 285

Gly Met Met Asn Lys Pro Val
290                 295
```

(2) INFORMATION FOR SEQ ID NO:13:

(i) SEQUENCE CHARACTERISTICS:
        (A) LENGTH: 28 amino acids
        (B) TYPE: amino acid
        (D) TOPOLOGY: linear (ii) MOLECULE TYPE: protein (xi) SEQUENCE DESCRIPTION: SEQ ID NO:13:

```
Leu Ile Ile Ala Lys Met Arg Met Val Ala Leu Lys Ala Gly Trp Gln
                 5                  10                  15
```

```
Gln Arg Lys Arg Ser Glu Arg Lys Ile Thr Leu Met
            20                  25
```

(2) INFORMATION FOR SEQ ID NO:14:

(i) SEQUENCE CHARACTERISTICS:
        (A) LENGTH: 28 amino acids
        (B) TYPE: amino acid
        (D) TOPOLOGY: linear (ii) MOLECULE TYPE: protein (xi) SEQUENCE DESCRIPTION: SEQ ID NO:14:

```
Leu Met Ile Leu Arg Leu Lys Ser Val Arg Leu Leu Ser Gly Ser Arg
                5                  10                  15
Glu Lys Asp Arg Asn Leu Arg Arg Ile Thr Lys Leu
            20                  25
```

(2) INFORMATION FOR SEQ ID NO:15:

(i) SEQUENCE CHARACTERISTICS:
        (A) LENGTH: 28 amino acids
        (B) TYPE: amino acid
        (D) TOPOLOGY: linear (ii) MOLECULE TYPE: protein (xi) SEQUENCE DESCRIPTION: SEQ ID NO:15:

```
Leu Met Leu Leu Arg Leu Arg Ser Val Arg Leu Leu Ser Gly Ser Lys
                5                  10                  15
Glu Lys Asp Arg Ser Leu Arg Arg Ile Thr Arg Met
            20                  25
```

(2) INFORMATION FOR SEQ ID NO:16:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:16:

```
Asp Arg Tyr Val Ala Val Val His Pro Ile Lys Ala Ala Arg Tyr Arg
                5                  10                  15
Arg Pro
```

(2) INFORMATION FOR SEQ ID NO:17:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:17:

```
Asp Arg Tyr Ile Ala Val Cys His Pro Val Lys Ala Leu Asp Phe Arg
                5                  10                  15
Thr Pro
```

(2) INFORMATION FOR SEQ ID NO:18:

(i) SEQUENCE CHARACTERISTICS:
        (A) LENGTH: 15 base pairs

```
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

TATCTAGGTC GACGG                                                    15

(2) INFORMATION FOR SEQ ID NO:19:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

CATCTTAGCA ATGAT                                                    15

(2) INFORMATION FOR SEQ ID NO:20:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

GTCGAGAATT CCCCG                                                    15

(2) INFORMATION FOR SEQ ID NO:21:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

CAGGCGCAGT AGCAT                                                    15

(2) INFORMATION FOR SEQ ID NO:22:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

TAGGTCGACG GTATC                                                    15

(2) INFORMATION FOR SEQ ID NO:23:

(i) SEQUENCE CHARACTERISTICS:
        (A) LENGTH: 15 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO:23:

CAGGCGCAGG ATCAT                                                    15

(2) INFORMATION FOR SEQ ID NO:24:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:24:

CGCATGGTGG CCCTC                                                    15

(2) INFORMATION FOR SEQ ID NO:25:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:25:

GGTGATCTTG CGCTC                                                    15

(2) INFORMATION FOR SEQ ID NO:26:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:26:

CGCAGCGTGC GTCTG                                                    15

(2) INFORMATION FOR SEQ ID NO:27:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:27:

CGTGATCCGC CGCAG                                                    15

(2) INFORMATION FOR SEQ ID NO:28:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:28:

```
AAGAGTGTCC GGCTC                                                         15

(2) INFORMATION FOR SEQ ID NO:29:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:29:

GGTGATCCGG CGGAG                                                         15

(2) INFORMATION FOR SEQ ID NO:30:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:30:

GAGCGCAAGA TCACC                                                         15

(2) INFORMATION FOR SEQ ID NO:31:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:31:

TCGAGAATTC CCCGG                                                         15

(2) INFORMATION FOR SEQ ID NO:32:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:32:

CTGCGGCGCG ATCAC                                                         15

(2) INFORMATION FOR SEQ ID NO:33:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:33:

TAGGTCGACG GTGTGG                                                        16

(2) INFORMATION FOR SEQ ID NO:34:
```

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:34:

CTCCGGCGGA TCACC                                               15

(2) INFORMATION FOR SEQ ID NO:35:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

GGGTCGAGAA CTAGT                                               15

(2) INFORMATION FOR SEQ ID NO:36:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:36:

Glu Tyr Pro Gly Ser Asn Thr Tyr Glu Asp
                5                  10

(2) INFORMATION FOR SEQ ID NO:37:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:37:

Glu Tyr Thr Gly Pro Ser Ala Phe Thr Glu
                5                  10

(2) INFORMATION FOR SEQ ID NO:38:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:38:

Thr Val Gln Asp Pro Ala Ser Met Arg Asp Val Gly
                5                  10

(2) INFORMATION FOR SEQ ID NO:39:

(i) SEQUENCE CHARACTERISTICS:

```
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:39:

Ser Pro Ile Gln Ile Phe Arg Gly Asp Pro Gly Pro Thr Cys Ser
                 5                  10                  15

(2) INFORMATION FOR SEQ ID NO:40:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO:40:

Ser Asp Ala Phe Pro Ser Ala Phe Pro Ser Ala Gly Ala
                 5                  10

(2) INFORMATION FOR SEQ ID NO:41:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO:41:

Ala Thr Thr Arg Glu Arg Val Thr Ala Cys Thr Pro Ser
                 5                  10

(2) INFORMATION FOR SEQ ID NO:42:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:42:

CTGGGCAACG TACTAGTCAT GTTTGGC                                          27

(2) INFORMATION FOR SEQ ID NO:43:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:43:

GTGGGCAATT CACTAGTCAT GTTTGTC                                          27
```